US012534468B2

(12) United States Patent
Chen et al.

(10) Patent No.: US 12,534,468 B2
(45) Date of Patent: *Jan. 27, 2026

(54) NANOMATERIAL COMPOSITIONS, SYNTHESIS, AND ASSEMBLY

(71) Applicant: RHODE ISLAND HOSPITAL, Providence, RI (US)

(72) Inventors: Qian Chen, Barrington, RI (US); Hongchuan Yu, Mansfield, MA (US); Yupeng Chen, Mansfield, MA (US)

(73) Assignee: Rhode Island Hospital, Providence, RI (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/156,306

(22) Filed: Jan. 18, 2023

(65) Prior Publication Data

US 2023/0183253 A1 Jun. 15, 2023

Related U.S. Application Data

(63) Continuation of application No. 15/527,283, filed as application No. PCT/US2015/061193 on Nov. 17, 2015, now Pat. No. 11,608,340.

(60) Provisional application No. 62/080,685, filed on Nov. 17, 2014.

(51) Int. Cl.

| | |
|---|---|
| ***C07D 487/04*** | (2006.01) |
| ***A61F 2/30*** | (2006.01) |
| ***A61K 45/06*** | (2006.01) |
| ***A61K 47/54*** | (2017.01) |
| ***A61K 47/69*** | (2017.01) |
| ***A61L 27/20*** | (2006.01) |
| ***A61L 27/22*** | (2006.01) |
| ***A61L 27/50*** | (2006.01) |
| ***A61L 27/52*** | (2006.01) |
| ***A61L 27/54*** | (2006.01) |
| ***C07D 471/04*** | (2006.01) |
| ***C07D 519/00*** | (2006.01) |

(52) U.S. Cl.

CPC ............ *C07D 487/04* (2013.01); *A61K 45/06* (2013.01); *A61K 47/542* (2017.08); *A61K 47/545* (2017.08); *A61K 47/6925* (2017.08); *A61L 27/20* (2013.01); *A61L 27/227* (2013.01); *A61L 27/50* (2013.01); *A61L 27/52* (2013.01); *A61L 27/54* (2013.01); *C07D 471/04* (2013.01); *C07D 519/00* (2013.01); *A61F 2/30756* (2013.01); *A61L 2300/252* (2013.01); *A61L 2300/406* (2013.01); *A61L 2300/414* (2013.01); *A61L 2400/12* (2013.01)

(58) Field of Classification Search

None

See application file for complete search history.

(56) References Cited

U.S. PATENT DOCUMENTS

| | | | | |
|---|---|---|---|---|
| 9,775,842 | B2 | 10/2017 | Chen et al. | |
| 10,344,300 | B2 | 7/2019 | Chen et al. | |
| 10,364,440 | B2 | 7/2019 | Webster et al. | |
| 11,608,340 | B2 * | 3/2023 | Chen | A61K 47/545 |
| 2010/0075904 | A1 | 3/2010 | Laurencin et al. | |
| 2011/0027339 | A1 | 2/2011 | Mao | |
| 2011/0136838 | A1 | 6/2011 | Atkinson et al. | |
| 2012/0171121 | A1 | 7/2012 | Webster | |
| 2012/0258094 | A1 | 10/2012 | Cohen et al. | |
| 2013/0059359 | A1 | 3/2013 | Wagner | |
| 2013/0129788 | A1 | 5/2013 | Webster et al. | |
| 2013/0288972 | A1 | 10/2013 | Chen et al. | |
| 2014/0171482 | A1 | 6/2014 | Webster et al. | |
| 2015/0258094 | A1 | 9/2015 | Chen et al. | |
| 2015/0258213 | A1 | 9/2015 | Chen et al. | |

FOREIGN PATENT DOCUMENTS

| | | | |
|---|---|---|---|
| JP | 2012-500204 | A | 1/2012 |
| JP | 2013-528405 | A | 7/2013 |
| JP | 6836989 | B2 | 2/2021 |
| WO | 2011/116085 | A1 | 9/2011 |

(Continued)

OTHER PUBLICATIONS

Extended European Search Report received for European Patent Application No. 15861300.0, mailed on Oct. 8, 2018, 10 pages.
Extended European Search Report received for European Patent Application No. 20193864.4, mailed on Jun. 9, 2021, 11 pages.
GenBank Accession No. NM_002379.3.
GenBank Accession No. NM_002380.3.
GenBank Accession No. NM_002381.4.
GenBank Accession No. NM_003833.3.
GenBank Accession No. NM_030583.2.
GenBank Accession No. NM_030590.2.
GenBank Accession No. NM_030592.2.

(Continued)

*Primary Examiner* — Erin E Hirt

(74) *Attorney, Agent, or Firm* — Adler Pollock & Sheehan P.C.

(57) ABSTRACT

Compositions or an assembly of a series of biomimetic compounds include chemical structures that mimic or structurally resemble a nucleic acid base pair. Complexes of nanotubes and agents are useful to deliver agents into the cells or bodily tissues of individuals for therapeutic and diagnostic purposes. Exemplary compounds include those of Formula (I), (III), (V) or (VII), or of Formula (II), (IV), (VI) or (VIII).

(I)

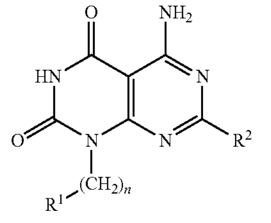

15 Claims, 8 Drawing Sheets

(56) References Cited

FOREIGN PATENT DOCUMENTS

| | | | |
|---|---|---|---|
| WO | 2012/094304 | A1 | 7/2012 |
| WO | 20120/94511 | A2 | 7/2012 |
| WO | 2012/153576 | A1 | 11/2012 |
| WO | 2013/142382 | A1 | 9/2013 |

OTHER PUBLICATIONS

GenBank Accession No. NP_002372.1.
International Search Report and Written Opinion received for PCT Patent Application No. PCT/US2015/061193, mailed on Mar. 28, 2016, 16 pages.
Partial Search Report received for European Patent Application No. 20193864.4, mailed on Mar. 4, 2021, 12 pages.
Partial Supplementary European Search Report received for European Patent Application No. 15861300.0, mailed on Jul. 4, 2018, 10 pages.
PubChem-CID-11974489, Jan. 3, 2007.
PubChem-CID-16103534, Jun. 18, 2007.
Asadi, et al., Janus-AT Bases: Synthesis, Self-Assembly, and Solid State Structures, The Journal of Organic Chemistry, vol. 72, 2007, pp. 466-475.
Fenniri, et al., “Helical Rosette Nanotubes: Design, Self-Assembly, and Characterization”, Journal of Am Chem Society, vol. 123, No. 16, 2001, pp. 3854-3855.
Mascal, et al., “Synthesis of the G-C DNA Base Hybrid with a Functional Tail”, The Journal of Organic Chemistry, vol. 71, No. 21, 2006, pp. 8146-8150.
Moralez, et al., “Helical Rosette Nanotubes With Tunable Stability and Hierarchy”, Journal of American Chemical Society, vol. 127, No. 23, Jun. 15, 2005, pp. 8307-8309.
Song, et al., “Self-Assembled Rosette Nanotubes for Incorporating Hydrophobic Drugs in Physiological Environments”, International Journal of Nanomedicine, Issue 6, Jan. 10, 2011, pp. 101-107.
Zhang, et al., “Arginine-Glycine-Aspartic Acid Modified Rosette Nanotube-Hydrogel Composites for Bone Tissue Engineering”, Biomaterials, vol. 30, No. 7, Mar. 1, 2009, pp. 1309-1320.
Zhao, et al., “Micro-Flowers Changing to Nano-Bundle Aggregates by Translocation of the Sugar Moiety in Janus TA Nucleosides”, Chemical Communications, vol. 49, 2013, pp. 3742-3744.

* cited by examiner

NANOMATERIAL COMPOSITIONS, SYNTHESIS, AND ASSEMBLY

CROSS-REFERENCE TO RELATED APPLICATIONS

This application is a continuation application of U.S. patent application Ser. No. 15/527,283, filed on May 16, 2017, now U.S. Pat. No. 11,608,340, which is a national stage application filed under 35 U.S.C. § 371 of International Patent Application No. PCT/US2015/061193, filed Nov. 17, 2015, which claims the priority and benefit of U.S. Provisional Patent Application No. 62/080,685, filed Nov. 17, 2014, the contents of each of which are incorporated by reference herein in their entireties.

STATEMENT OF GOVERNMENT INTERESTS

This invention was made with government support under P20GM104937 awarded by National Institutes of Health. The Government has certain rights in the invention.

FIELD OF THE INVENTION

The invention relates to nanoparticles deliver agents into cells or bodily tissues.

BACKGROUND

Nanoparticles, e.g., a microscopic particle with at least one dimension less than 100 nanometers (nm), have been used to transport molecules to cells and t issues. Various nanostructures, including liposomes, polymers, dendrimers, silicon or carbon materials, and magnetic nanoparticles, have been used as carriers in drug delivery systems. However, clinical use of such structures has often been hampered by undesirable or toxic side effects.

SUMMARY

The invention provides a solution to many of the drawbacks of existing nanoparticle delivery systems with compositions that mimic physiologic structures. Compositions or an assembly of a series of biomimetic compounds include chemical structures that mimic or structurally resemble a nucleic acid base pair. Two parts compose chemical structures of these compounds: 1. biomimetic adenine-thymine (A^T) and guanine-cytosine (G^C) fused base and/or its analogues; 2. Amino acid, poly amino acids, amine or polyamine. The compounds are used for the purpose of generating nanomaterials that assemble into nanostructures including nanotubes and/or nanorods and/or nanopieces and/or nanosheets. Because of their structure, these nanomaterials are useful for a variety of clinical applications including bio-adhesion and drug delivery with little or no adverse side effects. For example, a nanosheet may cover an area encompassing at least a millimeter (mm), centimeter (cm), or meter (m) squared. In some applications, nanosheets are optionally stacked, e.g., 2-10, 50, 100, 500, 1000 sheets.

In embodiments, the nanomaterial compositions and methods are useful to introduce a therapeutic or diagnostic agent into a cell or tissue or tissue matrix using nanotubes or components of nanotubes, or processed nanopieces. These nanotubes or nanopieces are made from compounds of Formulae (I)-(VIII), which contain bicyclic core structures of various heteroatoms and substituents with their varied orientation in space. These biomimetic structures can now self-assemble to form nanotubes, e.g., rosette nanotubes (RNT), of various sizes and charge depending on the Formula chosen and their corresponding substituents, e.g. R groups. Coupling of compounds of Formulae (I), (III), (V) and/or (VII) to form dimeric structures as shown in Formulae (II), (IV), (VI) or (VIII) can also self-assemble to produce nanotubes and nanopieces. These nanotubes and nanopieces expand on the structural diversity of these materials and provide more opportunity to generate biomaterials with desired properties for its intended use.

Compounds of Formulae (I)-(VIII) can form modules that assemble into nanotubes. For example, the structures comprise Formulae (I), (III), (V) or (VII) or dimers thereof.

In one embodiment of the present disclosure compounds are chosen from Formula (I)

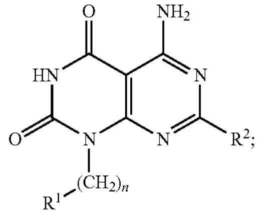

(III)

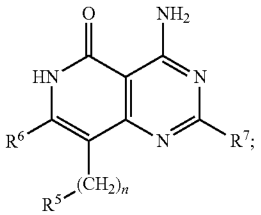

(V)

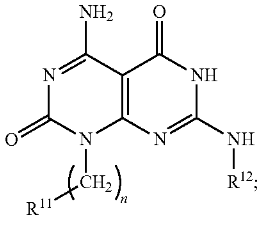

or (VII)

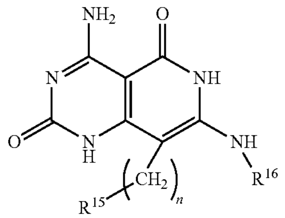

or a pharmaceutically acceptable salt, ester or amide thereof wherein, n is an integer of 1, 2, 3, 4, 5 or 6;

$R^1$, $R^5$, and $R^{15}$ are selected from α-amino acid, β-amino acid, α-polypeptide, β-polypeptide,

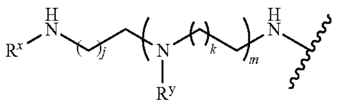

or

-continued

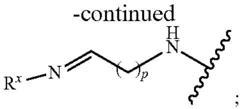

;

$R^{11}$ is selected from β-amino acid, β-polypeptide,

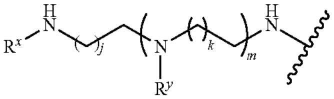

or

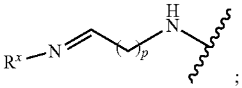

;

j, k, m and p are independently an integer of 0 to 20;

$R^x$ is aliphatic or H;

$R^y$ is H or

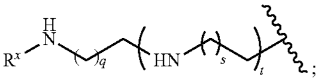

;

q, s and t are independently an integer of 0 to 20;

$R^2$, $R^6$ and $R^7$ are independently selected from H, $CH_3$, or $NHR^z$; and $R^7$, $R^{12}$ and $R^{16}$ are independently selected from H or aliphatic.

In some embodiments, $R^1$ in Formula (I) is

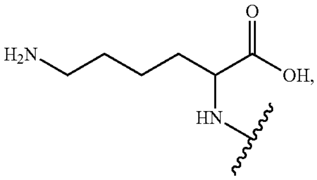

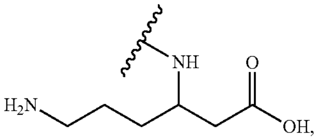

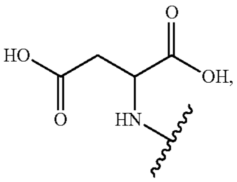

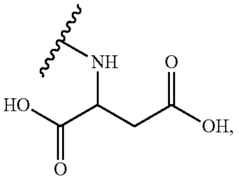

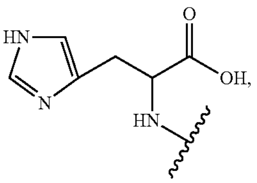

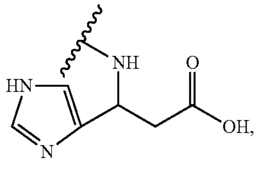

-continued

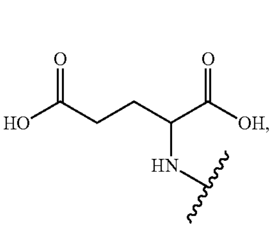

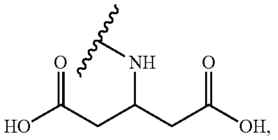

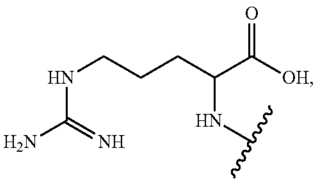

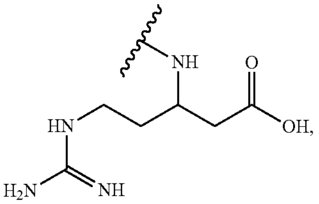

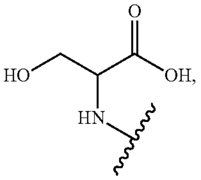

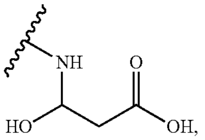

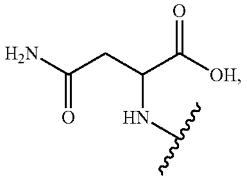

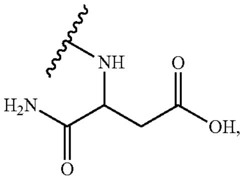

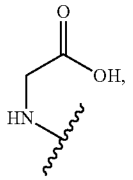

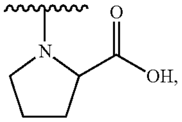

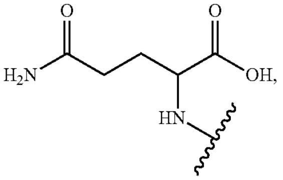

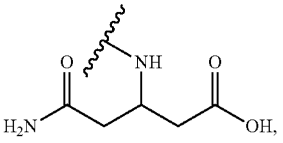

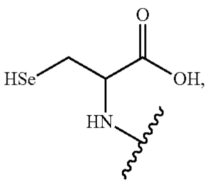

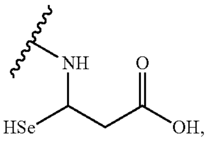

-continued
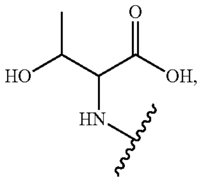
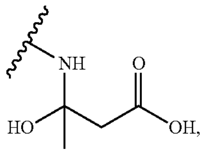
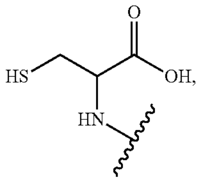
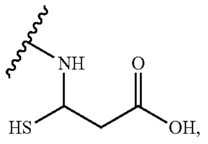
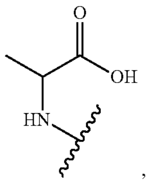
,
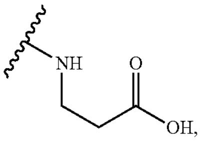
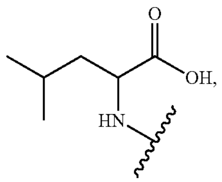
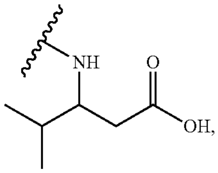
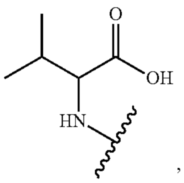
,
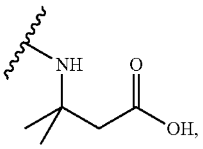
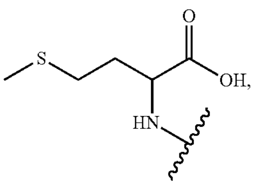
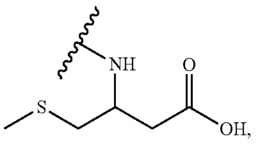
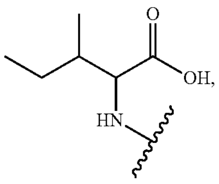
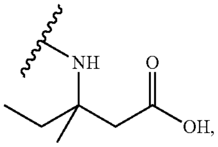
-continued
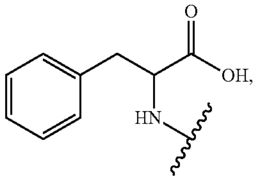
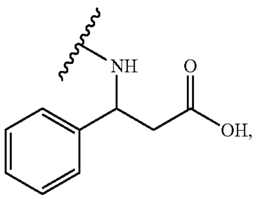
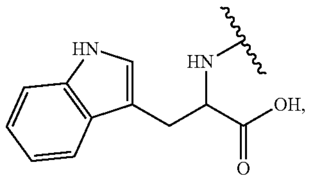
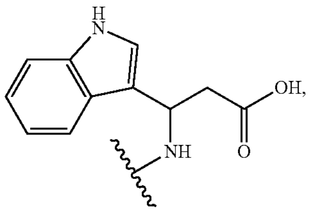
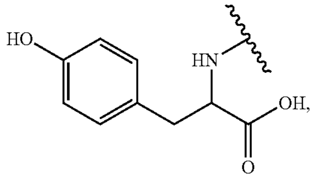
or
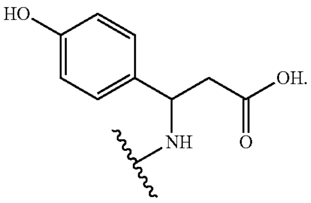
In another embodiment, $R^5$ in Formula (III) is
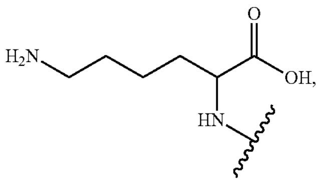
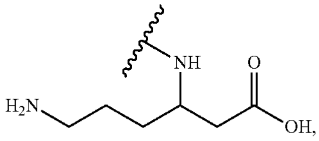
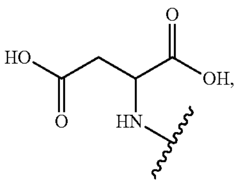
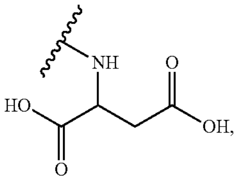

-continued
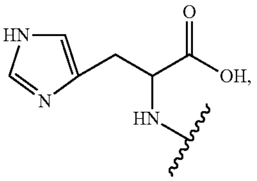
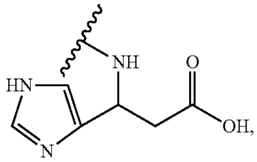
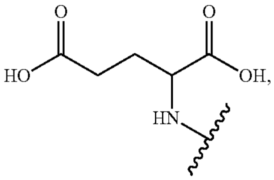
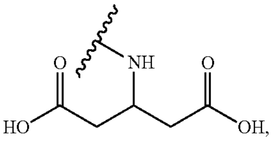
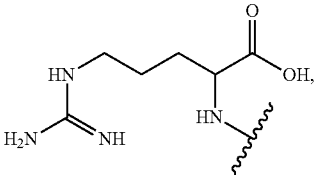
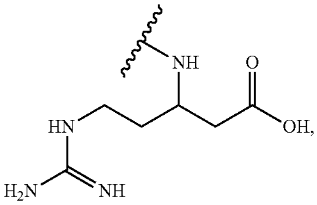
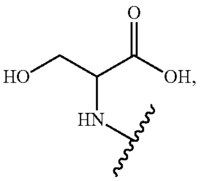
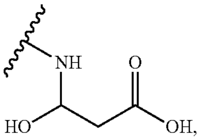
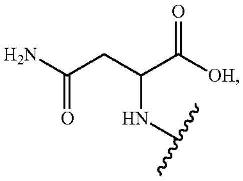
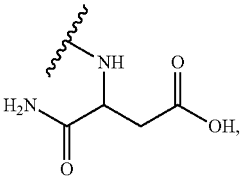
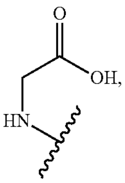
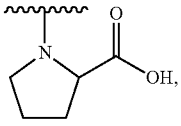
-continued
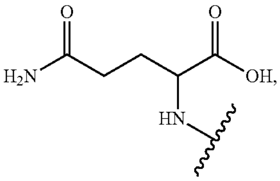
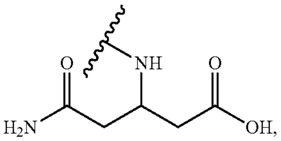
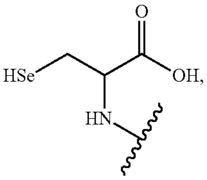
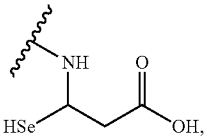
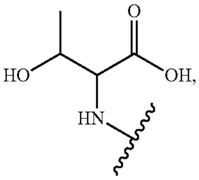
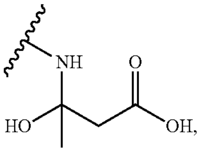
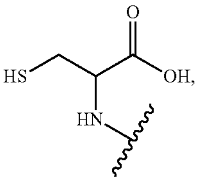
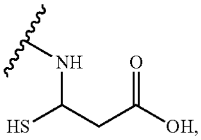
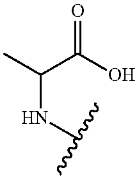
,
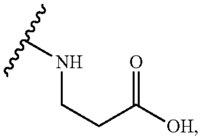
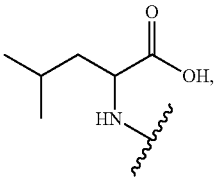
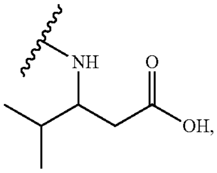
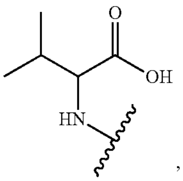
,
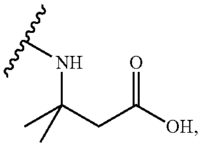

-continued
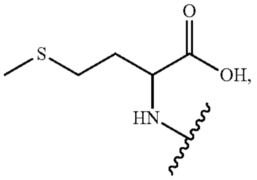
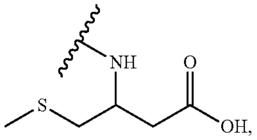
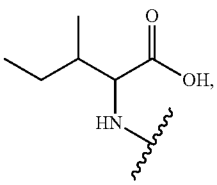
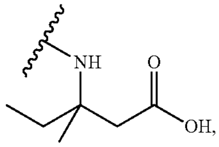
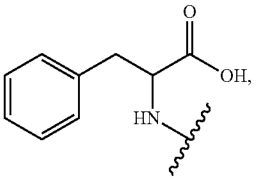
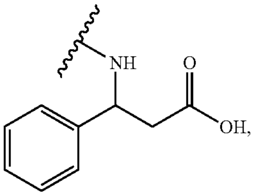
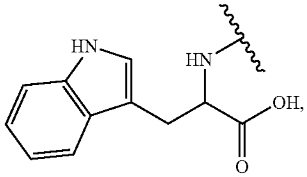
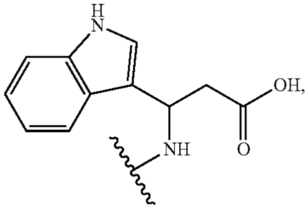
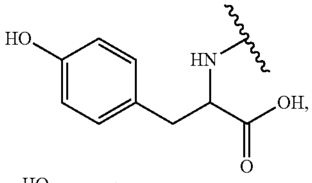
or
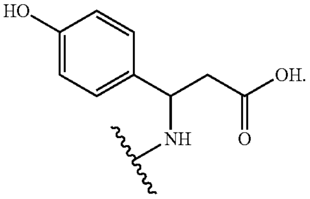
In a further embodiment, $R^{11}$ in Formula (V) is
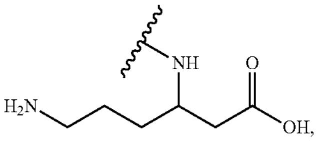
-continued
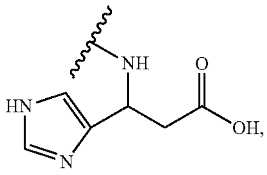
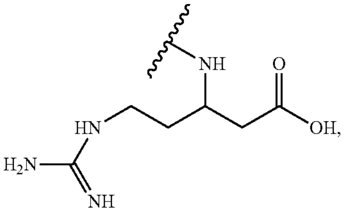
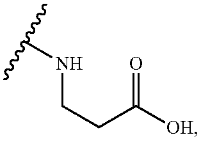
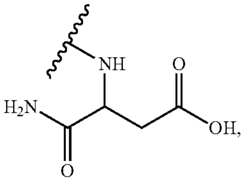
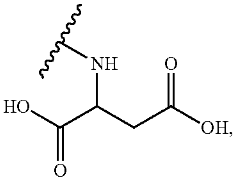
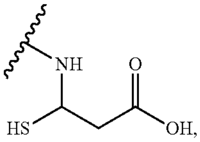
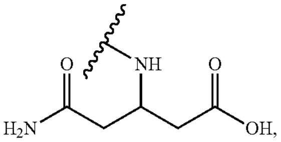
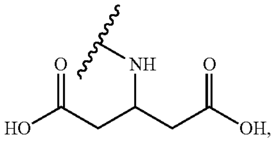
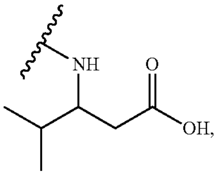
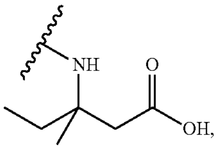
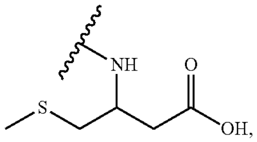
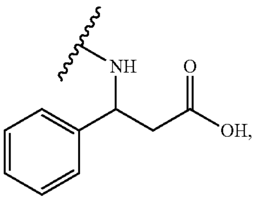
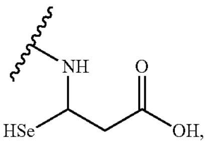
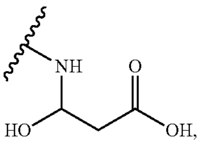
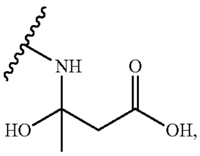
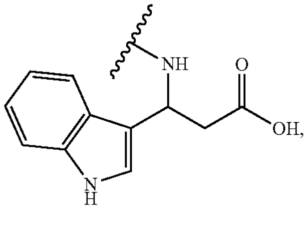

-continued
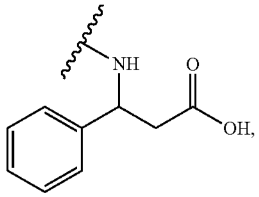
or
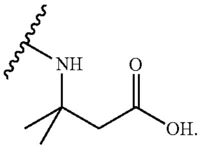
Lastly, in some embodiments $R^{15}$ in Formula (VII) is
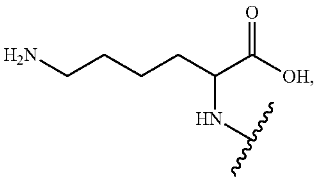
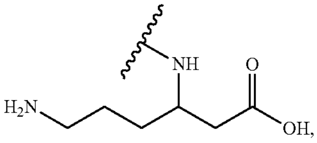
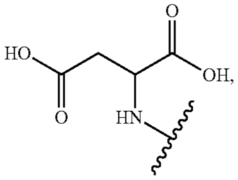
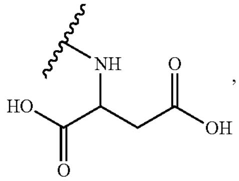
,
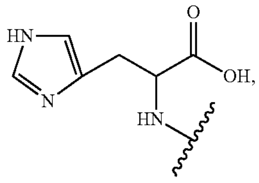
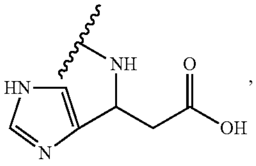
,
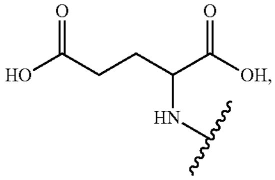
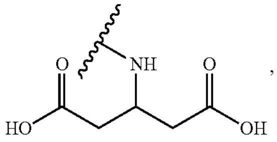
,
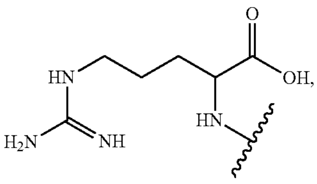
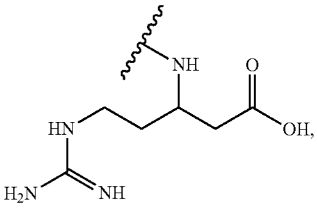
-continued
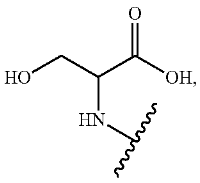
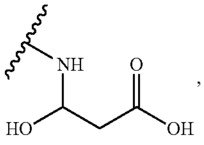
,
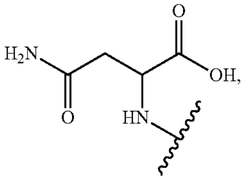
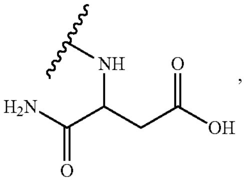
,
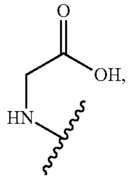
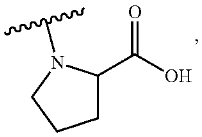
,
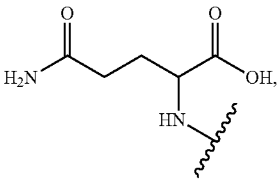
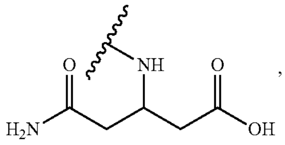
,
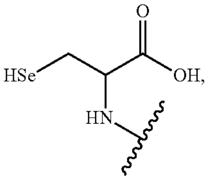
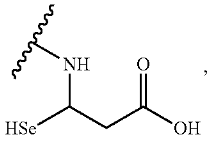
,
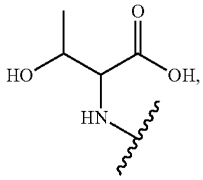
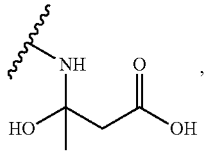
,
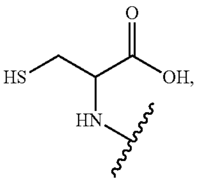
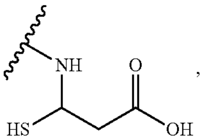
,
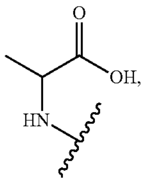
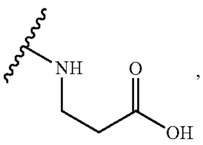
,
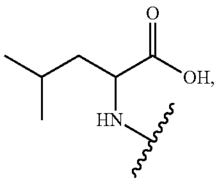
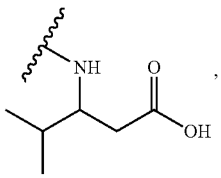
,
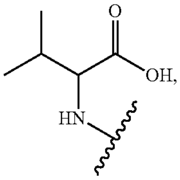

-continued
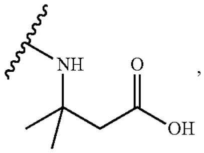
,
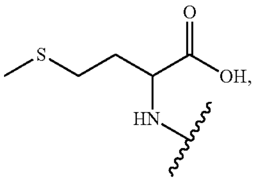
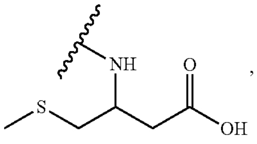
,
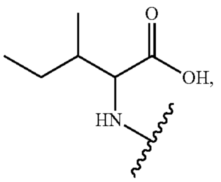
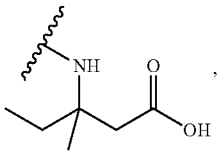
,
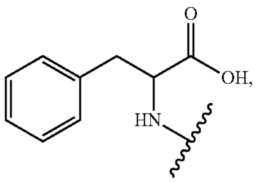
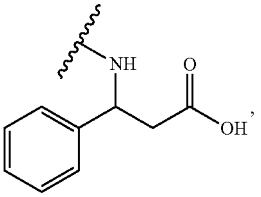
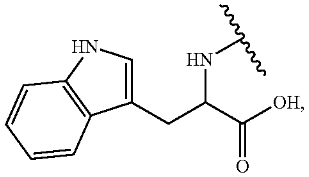
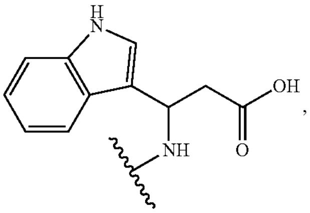
,
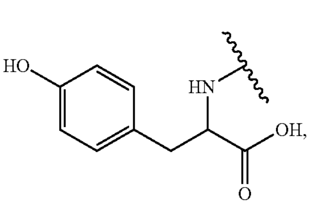
or
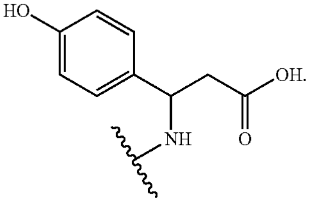
Examples of dimers of the compounds shown in Formula (I), (III), (V) or (VII) are described below. For example:
(II)
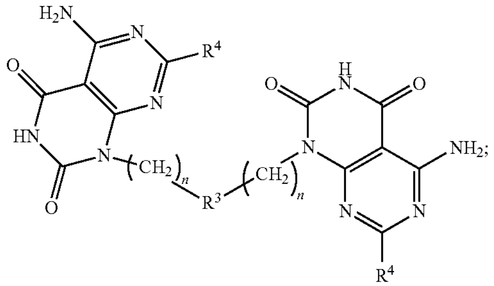
(IV)
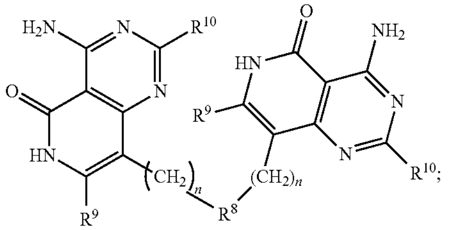
(VI)
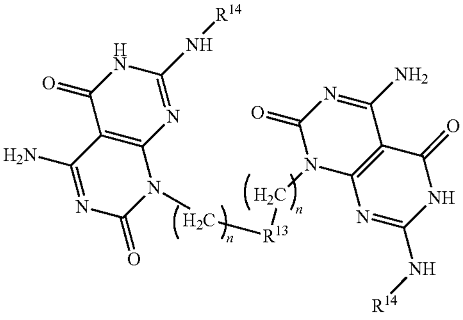
or
(VIII)
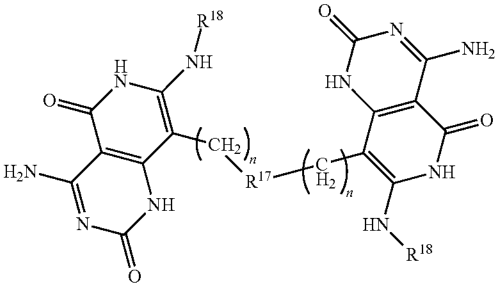
or a pharmaceutically acceptable salt, ester or amide thereof wherein,
n is 1, 2, 3, 4, 5 or 6;
$R^3$, $R^8$, and $R^{17}$ are selected from α-amino acid, β-amino acid, α-polypeptide, β-polypeptide,
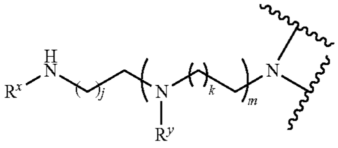
or -continued

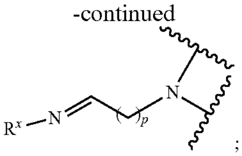

;

$R^{13}$ is selected from β-amino acid, β-polypeptide,

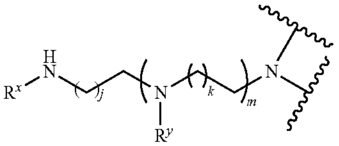

or

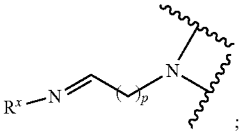

;

j, k, m and p are independently an integer of 1 to 20;

$R^x$ is aliphatic or H;

$R^y$ is H or

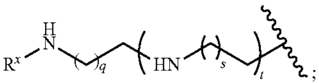

;

q, s and t are independently an integer of 1 to 20;

$R^4$, $R^9$ and $R^{10}$ are independently selected from H, $CH_3$, or $NHR_z$, and $R^z$, $R^{14}$, $R^{18}$ are independently selected from H or aliphatic.

In some embodiments $R^3$ in Formula (II) is

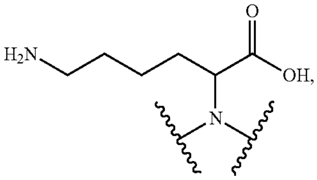

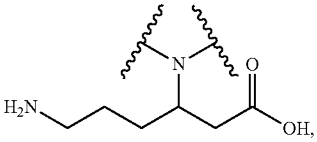

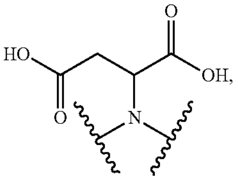

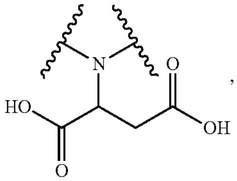

,

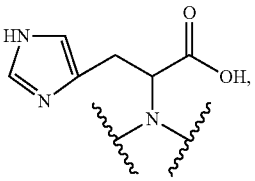

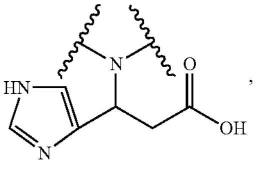

,

-continued

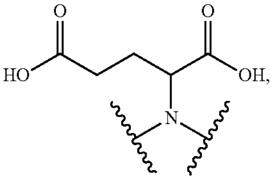

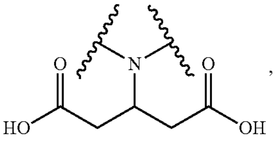

,

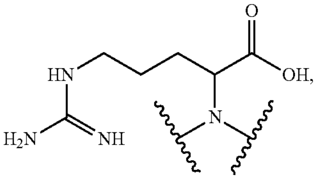

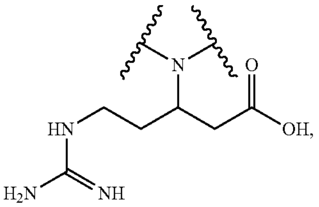

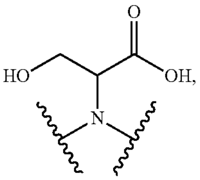

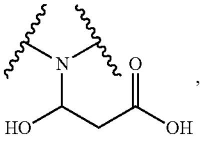

,

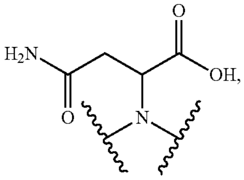

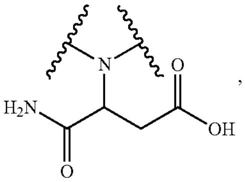

,

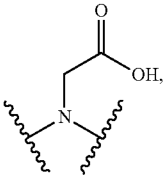

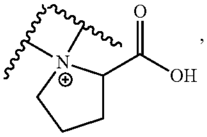

,

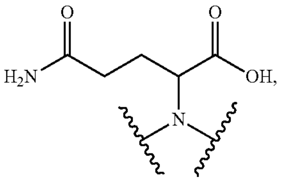

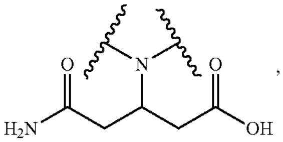

,

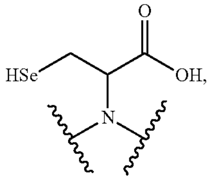

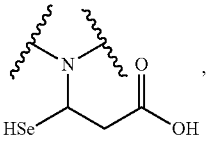

,

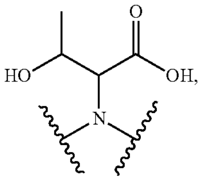

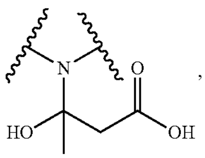

,

-continued
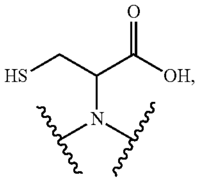
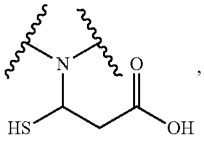
,
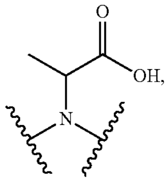
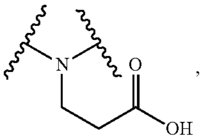
,
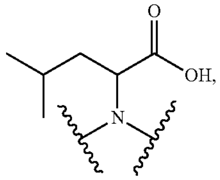
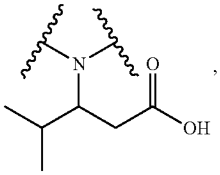
,
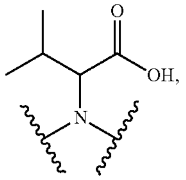
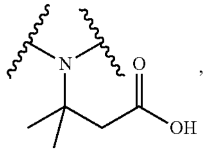
,
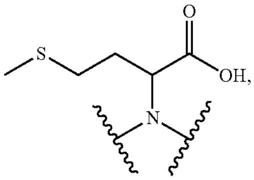
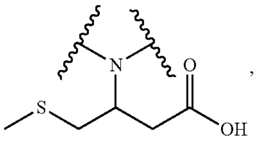
,
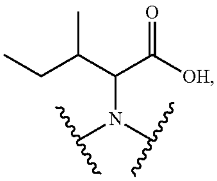
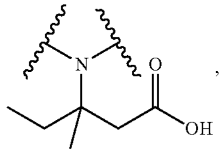
,
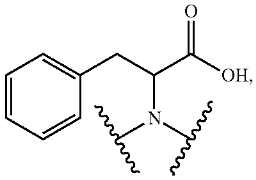
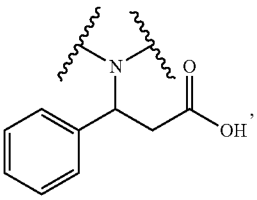
,
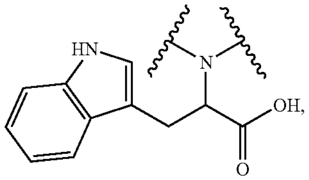
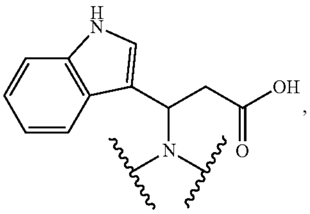
,
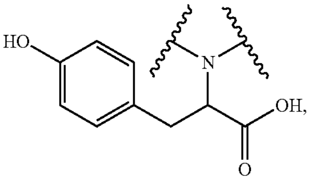
or
-continued
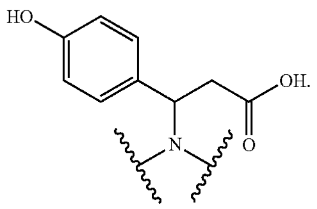
In another embodiment $R^8$ in Formula (IV) is
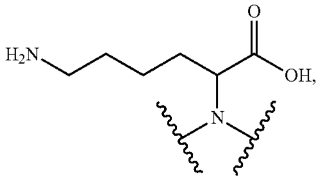
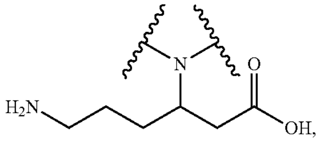
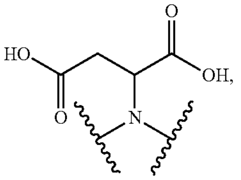
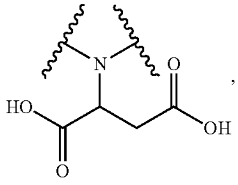
,
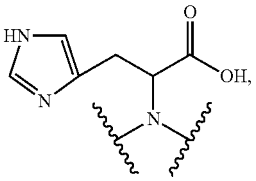
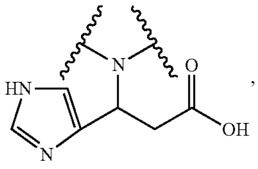
,
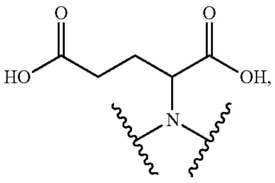
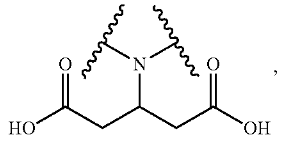
,
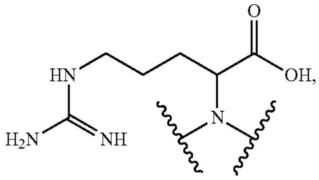
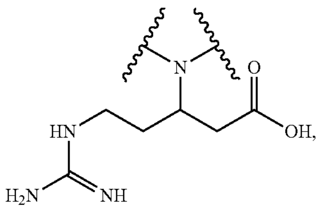

-continued
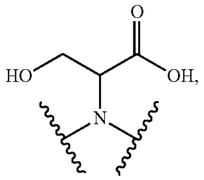
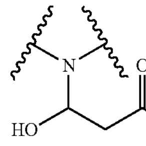
,
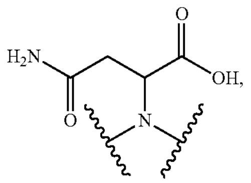
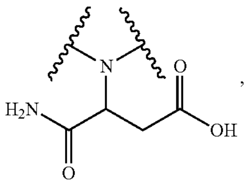
,
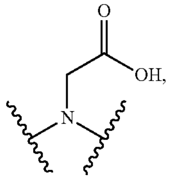
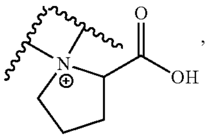
,
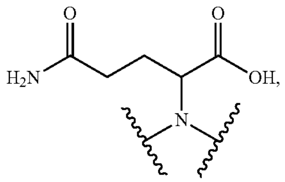
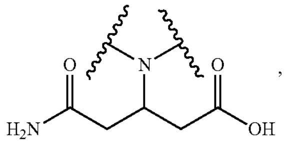
,
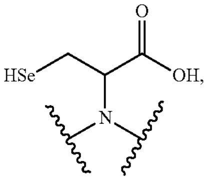
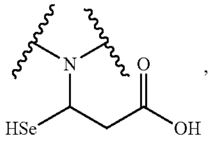
,
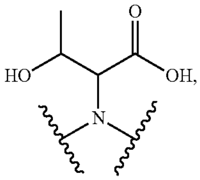
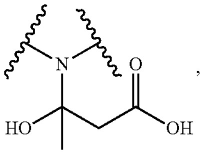
,
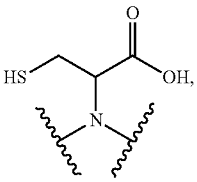
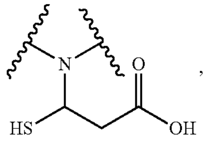
,
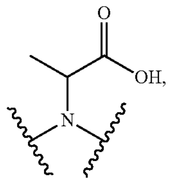
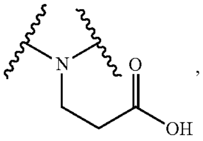
,
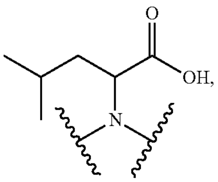
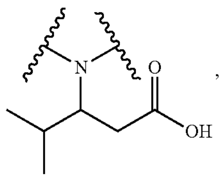
,
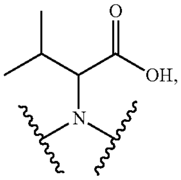
-continued
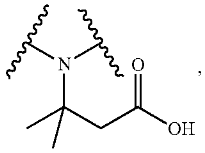
,
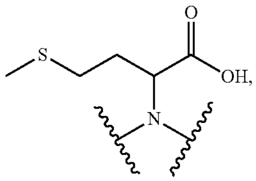
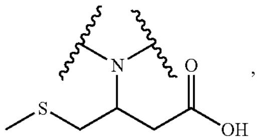
,
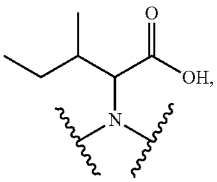
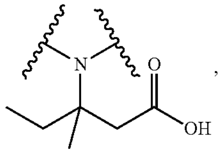
,
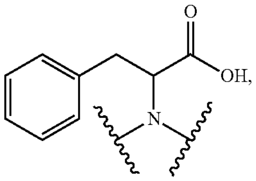
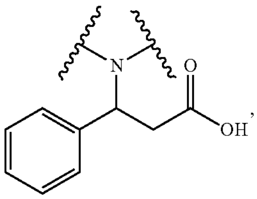
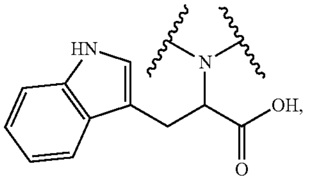
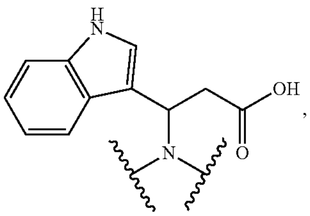
,
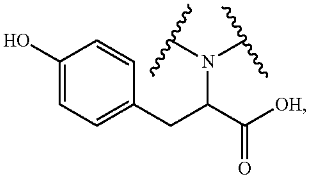
or
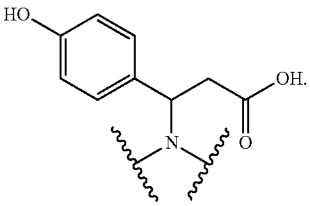
In a further embodiment $R^{13}$ in Formula (VI) is
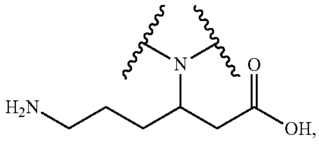

-continued
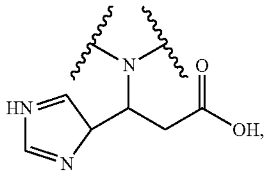
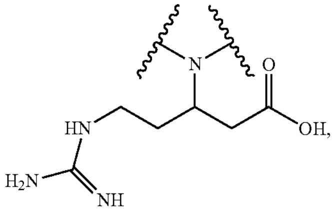
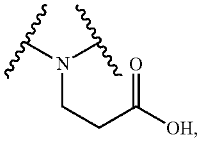
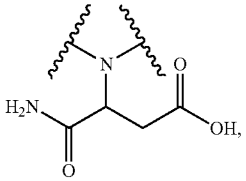
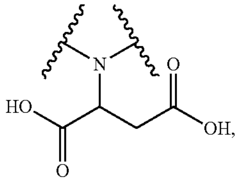
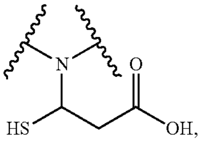
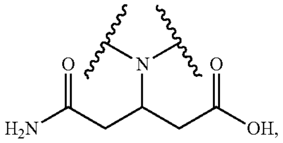
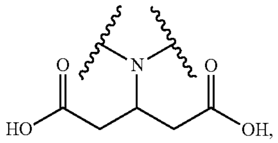
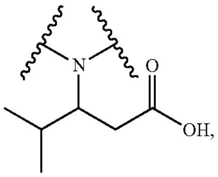
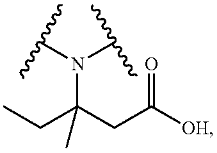
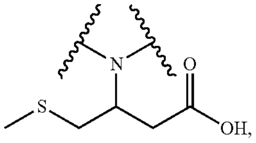
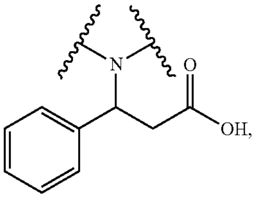
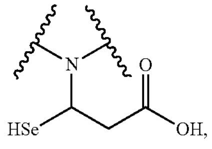
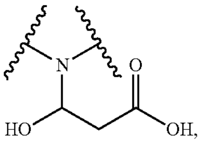
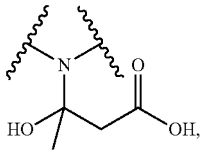
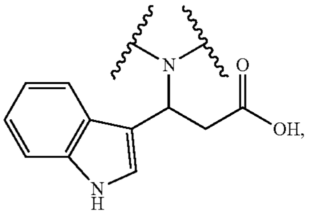
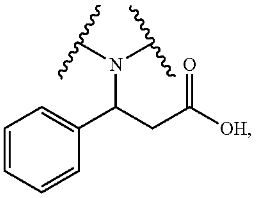
-continued
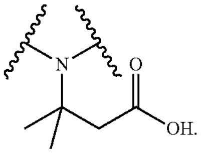
Lastly, in some embodiments $R^{17}$ in Formula (VIII) is
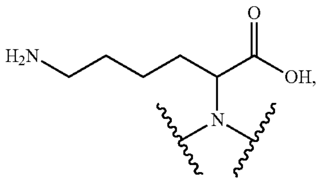
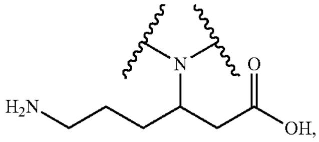
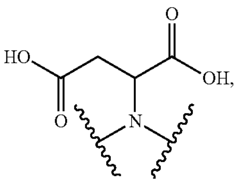
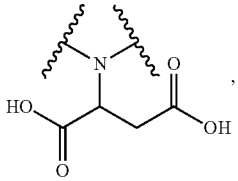
,
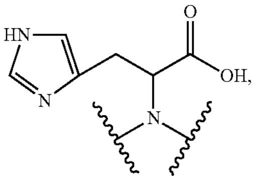
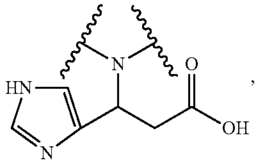
,
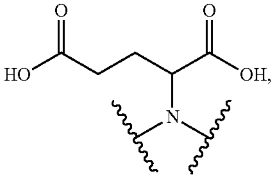
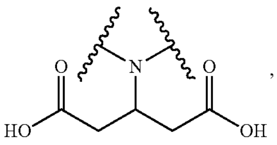
,
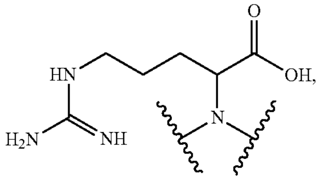
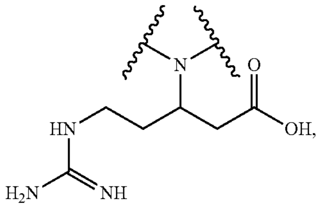
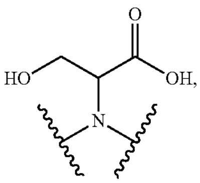
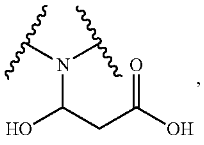
, -continued
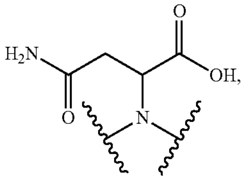
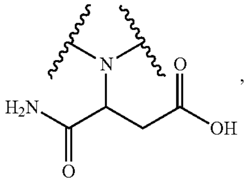
,
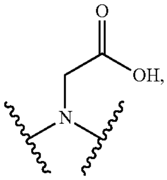
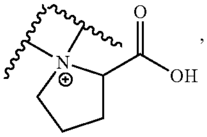
,
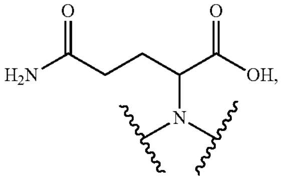
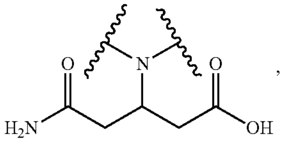
,
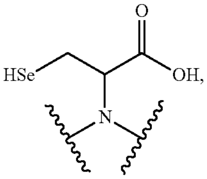
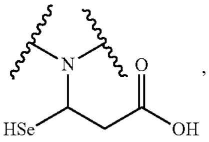
,
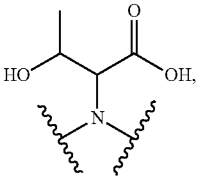
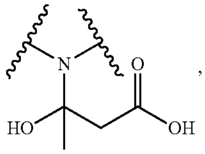
,
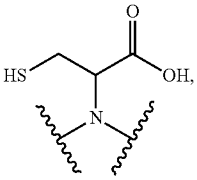
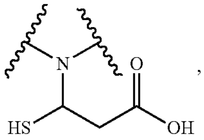
,
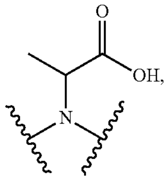
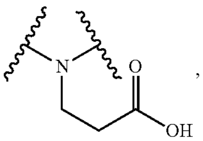
,
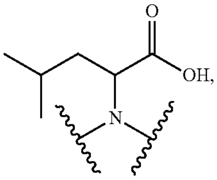
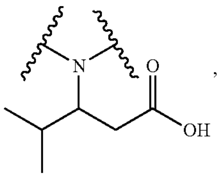
,
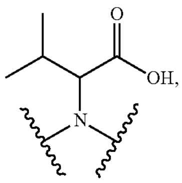
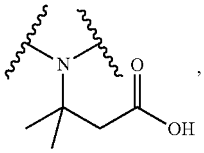
,
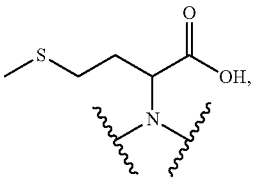
-continued
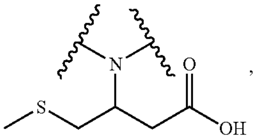
,
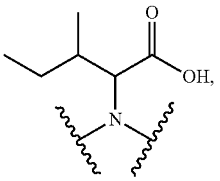
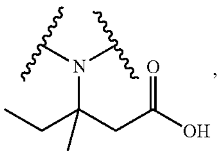
,
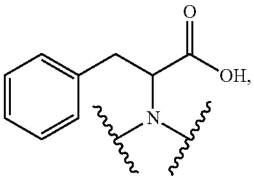
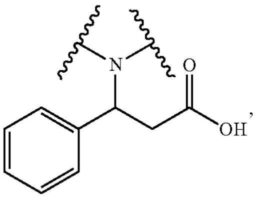
,
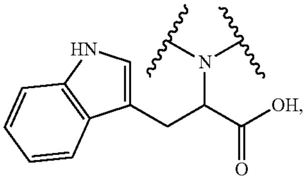
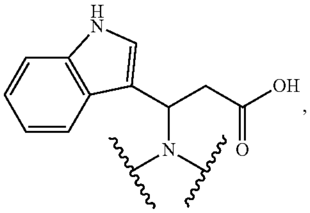
,
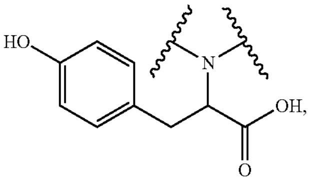
or
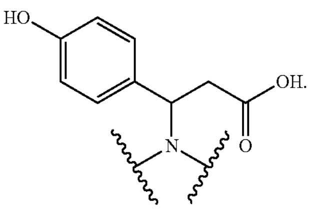
In embodiments, the compound is:
(Compound A)
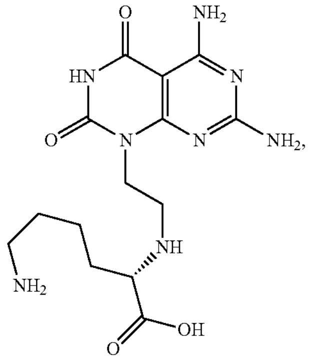

-continued (Compound B)

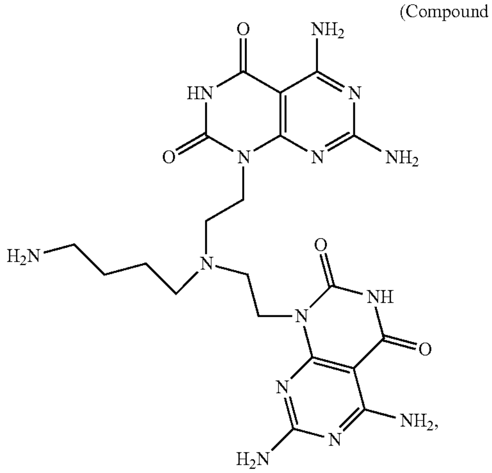

(Compound C)

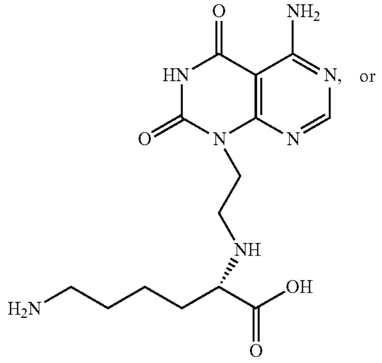

Compound (D)

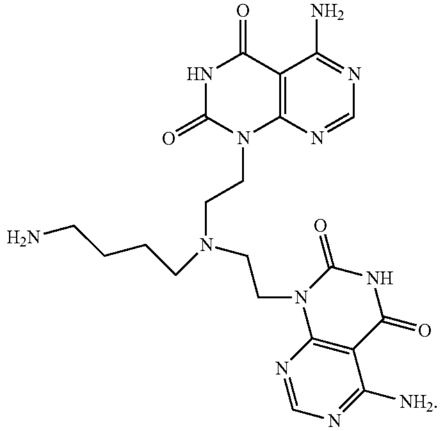

In another aspect, the invention features a nanostructure comprising any of the compositions described herein (e.g., a composition comprising a compound of Formula (I), (III), (V) or (VII); a compound of Formula (II), (IV), (VI) or (VIII); and/or Compound A, Compound B, Compound C, or Compound D as described herein). In embodiments, the nanostructure includes a nanotube. In embodiments, the nanostructure includes a nanosheet. In embodiments, the nanostructure includes a nanorod. In embodiments, the nanostructure includes a nanopiece. In embodiments, the nanostructure includes a nanostructured particle. In embodiments, the nanostructure includes a nanostructured matrix. In embodiments, the nanostructure is a nanowire. In embodiments, the nanostructure is a nanowhisker. In embodiments, the nanostructure is a nanoribbon.

In another aspect, the invention features a nanostructure formed from any of the compositions described herein (e.g., a composition comprising a compound of Formula (I), (III), (V) or (VII); a compound of Formula (II), (IV), (VI) or (VIII); and/or Compound A, Compound B, Compound C, or Compound D as described herein). In embodiments, the nanostructure comprises a nanotube. In embodiments, the nanostructure comprises a nanosheet. In embodiments, the nanostructure comprises a nanorod. In embodiments, the nanostructure comprises a nanopiece. In embodiments, the nanostructure comprises a nanostructured particle. In embodiments, the nanostructure is a nanostructured matrix. In embodiments, the nanostructure is a nanowire. In embodiments, the nanostructure is a nanowhisker. In embodiments, the nanostructure is a nanoribbon.

In another aspect, the invention features a composition comprising a nanostructure as described herein. In embodiments, the nanostructure comprises a nanotube. In embodiments, the nanostructure comprises a nanosheet. In embodiments, the nanostructure comprises a nanorod. In embodiments, the nanostructure comprises a nanopiece. In embodiments, the nanostructure comprises a nanostructured particle. In embodiments, the nanostructure comprises a nanostructured matrix. In embodiments, the nanostructure is a nanowire. In embodiments, the nanostructure is a nanowhisker. In embodiments, the nanostructure is a nanoribbon.

In another aspect, the compounds described herein (e.g., compounds of Formula (I), (III), (V) or (VII); compounds of Formula (II), (IV), (VI) or (VIII); and/or Compound A, Compound B, Compound C, or Compound D as described herein) self-assemble to form a nanostructure. In embodiments, the nanostructure comprises a nanotube. In embodiments, the nanostructure comprises a nanosheet. In embodiments, the nanostructure comprises a nanorod. In embodiments, the nanostructure comprises a nanopiece. In embodiments, the nanostructure comprises a nanostructured particle. In embodiments, the nanostructure comprises a nanostructured matrix. In embodiments, the nanostructure is a nanowire. In embodiments, the nanostructure is a nanowhisker. In embodiments, the nanostructure is a nanoribbon.

In another aspect, the invention features a nanotube formed from any of the compositions described herein (e.g., a composition comprising a compound of Formula (I), (III), (V) or (VII); a compound of Formula (II), (IV), (VI) or (VIII); and/or Compound A, Compound B, Compound C, or Compound D as described herein).

In another aspect, the invention features a composition comprising a nanostructure (e.g., a nanotube) formed from any of the compositions described herein (e.g., a composition comprising a compound of Formula (I), (III), (V) or (VII); a compound of Formula (II), (IV), (VI) or (VIII); and/or Compound A, Compound B, Compound C, or Compound D as described herein).

In embodiments, a composition as described herein further comprises one or more diagnostic agents (e.g., a molecular probe or a molecular beacon).

In embodiments, a composition as described herein further comprises one or more therapeutic agents (e.g., a therapeutic agent comprising a nucleic acid, peptide or small molecule).

In embodiments, a nanostructure as described herein further comprises one or more diagnostic agents (e.g., a molecular probe or a molecular beacon).

In embodiments, a nanostructure as described herein further comprises one or more therapeutic agents (e.g., a therapeutic agent comprising a nucleic acid, peptide or small molecule).

In some embodiments of the disclosure, compounds of Formula (I), (III), (V) or (VII) self-assemble to form a nanostructure. In another embodiment of the disclosure Formula (II), (IV), (VI) or (VIII) self-assemble to form a nanostructure. In embodiments, the nanostructure comprises a nanotube. In embodiments, the nanostructure comprises a nanosheet. In embodiments, the nanostructure comprises a nanorod. In embodiments, the nanostructure comprises a nanopiece. In embodiments, the nanostructure comprises a nanostructured particle. In embodiments, the nanostructure comprises a nanostructured matrix. In embodiments, the nanostructure is a nanowire. In embodiments, the nanostructure is a nanowhisker. In embodiments, the nanostructure is a nanoribbon.

Embodiments of the present disclosure include the formation of a composite or complex or combination of one or more agents, such as therapeutic or diagnostic agents, and a nanotube or a component of a nanotube, where the one or more agents are attached to or otherwise bound to the nanotube or component of a nanotube. These agents may be therapeutic agents or diagnostic agents such as peptides, proteins, small molecules, nucleic acids and molecular beacons. Embodiments of the present disclosure are further directed to a product made by the process of mixing together nanotubes as described herein or modules forming nanotubes as described herein and one or more agents in aqueous media under conditions which cause the nanotubes or components of nanotubes to combine with the one or more agents to form a complex or combination in aqueous media where the one or more agents are attached or otherwise bound through steric, ionic, or other forces to the nanotube a component of a nanotube. According to one aspect, the one or more agents are bound through intermolecular forces.

Also provided herein is a system for selective drug delivery to a bodily tissue or cell. The system includes a nanocarrier and a cargo molecule, where the nanocarrier includes a compound of Formula (I), (III), (V) or (VII).

Also provided herein is a composition that includes a nanocarrier and a cargo molecule, where the nanocarrier comprises a compound of Formula (I), (III), (V) or (VII).

For example, the compound of the described system or composition is selected from the group consisting of:

(Compound A)

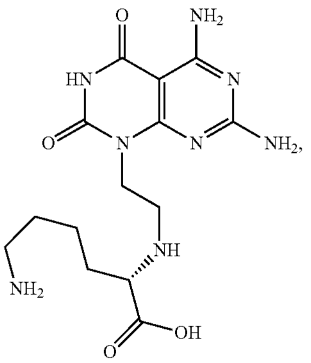

-continued (Compound B)

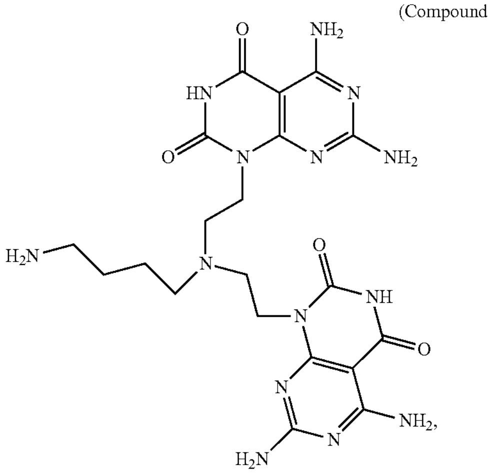

(Compound C)

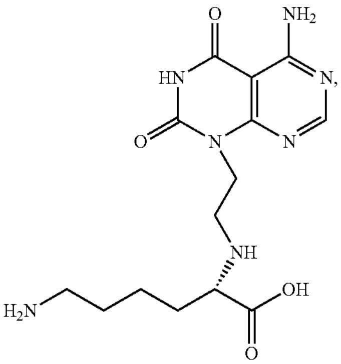

and

Compound (D)

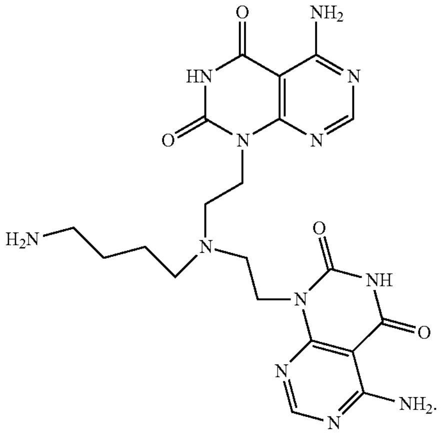

For example, the cargo molecule of the described system or composition may include a therapeutic agent or a diagnostic agent. Exemplary therapeutic agents include, but are not limited to, a nucleic acid, a peptide or a small molecule. Exemplary diagnostic agents include, but are not limited to, a molecular probe, a molecular beacon, a fluorescence dye, a fluorescently labeled protein or peptide, or MRI imaging probe.

The nanomaterial (compound) described herein can also be used for implant, such as an orthopedic device that is inserted into or replaces existing bone or cartilage tissue or other types of tissues, coating an implant/device, tissue engineering, and/or device for tissue healing, regeneration or repair.

For example, the nanomaterial (compound) described herein is used for an implant. Typically, an implant includes a composition that comprises a nanostructured matrix, where the nanostructured matrix is formed by a compound described herein.

In some embodiments, the implant also comprises matrilin. For example, the matrilin comprises Matrilin-3 or a functional domain or fragment thereof.

In some embodiments, the implant also comprises an orthopedic implant. For example, an orthopedic implant is used to contact structural bodily tissues such as bone or cartilage.

In some embodiments, the implant further includes a bioactive agent or an immunosuppressive agent, e.g., to reduce or minimize immune rejection of implanted material.

Bioactive agents are also known in the art. For example, bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FK506, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

Also provided is a method for making an implant. The method includes preparing a solution including a compound; forming in the solution a matrix suitable for implant, where the matrix includes a nanostructured matrix formed by a compound described herein.

Such implant can be used for healing a tissue, which includes steps of preparing an implant according to the method described above, and administering the implant into a tissue in need of an implant, thereby healing the tissue. Typically, the tissue (e.g., bone, cartilage) comprises a growth plate fracture or defect. Typically, the implant is placed into the fracture or defect. The compounds are optionally formulated into defect-filling compositions, e.g., bone cement or fillers, dermal fillers, and/or polymeric structures to be administered to a variety of tissues for healing or regeneration purposes.

In some embodiments, the nanomaterial (compound) described herein is used for coating a device/implant. Typically, a system for coating a device includes a composition that comprises a solution of a compound described herein.

For example, a method for coating a device/implant includes steps of applying a composition that comprises a solution of a compound described herein to the device/implant, where the solution includes nanotubes formed by a compound described herein.

In some embodiments, the coating solution further includes an immunosuppressive agent. For example, immunosuppressive agents that can be utilized include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FK506, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

In some embodiments, the nanomaterial (compound) described herein is used for tissue engineering.

In some embodiments, a composition for tissue engineering includes a nanomaterial, where the nanomaterial comprises a compound described herein.

In some embodiments, the composition for tissue engineering further includes a biodegradable polymer. Exemplary biodegradable polymer includes, but is not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), copolymers, and terpolymers.

In some embodiments, the composition for tissue engineering further includes a bioactive agent and/or an inert agent. For example, bioactive agent is bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof. For example, an inert agent is a carrier, an excipient, a sterilizing solution, and/or a labeling solution.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FK506, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

In some embodiments, the composition for tissue engineering further includes a metal or a ceramic.

In some embodiments, a method for tissue engineering includes steps of administering the composition for tissue engineering described herein to a tissue, where the nanomaterial is fabricated and solidified with blood of said tissue, thereby facilitating the tissue growth for tissue engineering.

In some embodiments, a method for making a device for tissue repair includes the steps of preparing a composition that comprises a compound of the invention and a peptide, forming a device that includes a structural element and the composition. Typically, the peptide is covalently linked to the compound. Typically, the structural element comprises a polysaccharide polymer material. For example, the polysaccharide polymer material comprises an agarose or a hydrogel. For example, agarose comprises a solution comprising 5% (w/w) agarose. Typically, the device comprises a specific shape that fits into a defect tissue or is malleable to form into a shape of a defect tissue.

In some embodiments, a method for repairing a tissue includes administering a device prepared accordingly into defect tissue. Typically, the tissue is cartilage, bone or skin.

The compositions described herein are purified. Purified compounds are at least 60% by weight (dry weight) the compound of interest. Preferably, the preparation is at least 75%, more preferably at least 90%, and most preferably at least 99% or higher by weight the compound of interest. Purity is measured by any appropriate standard method, for example, by High-performance liquid chromatography, polyacrylamide gel electrophoresis, The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The aspects, advantages and other features of the disclosure will become apparent in view of the following detailed description, which discloses various non-limiting embodiments of the disclosure. In describing embodiments of the present disclosure, specific terminology is employed for the sake of clarity. However, the disclosure is not intended to be limited to the specific terminology so selected. It is to be understood that each specific element includes all technical equivalents that operate in a similar manner to accomplish a similar purpose. Additionally, all of the citations herein are incorporated by reference in their entirety.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations.

DETAILED DESCRIPTION

Figure 1:
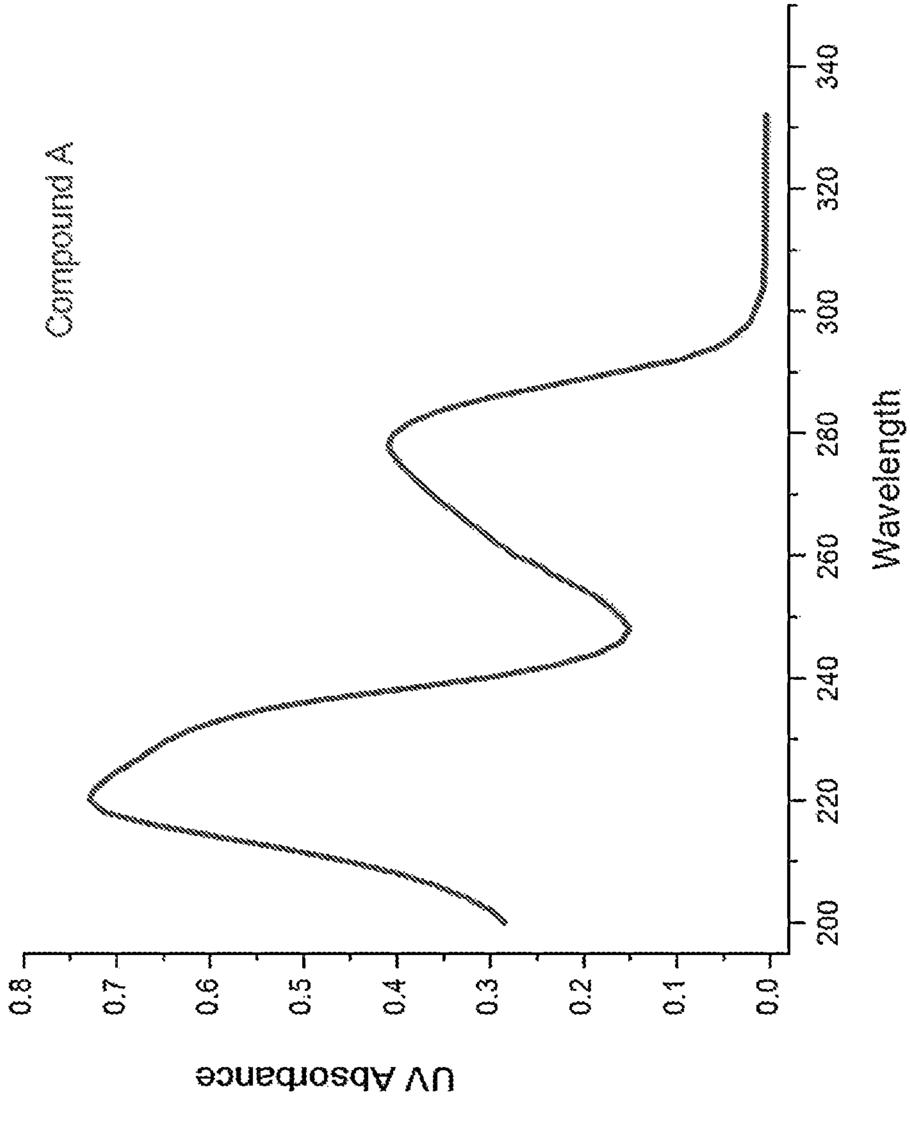
FIG. 1 is a graph showing UV absorbance curve of 0.15 g/L aqueous solution of Compound A.

Embodiments of the present disclosure involve making composites or components of nanostructures and therapeutic or diagnostic agents including those known in the art and including nucleic acids, such as DNA, RNA or their analogues, peptides, proteins, small molecules, and molecular beacons. RNA can be small RNA including siRNA and miRNA. The nanostructures are carriers that are formed from self-assembled modules as described below and can be further processed to yield nanopieces. In some embodiments the nanostructures may be complexed with nucleic acids, such as DNA, RNA or their analogues, peptides, proteins, small molecules, and molecular beacons. Thus, the compounds of the invention can be used as nano-vectors for drug delivery, which could facilitate drug transportation into cells, tissues, and/or organs.

Compounds of the invention can be used as nanomaterials in medical devices, during tissue repair including surgery and/or tissue engineering. For example, nanomaterials of the invention can be used in bio-adhesion between molecules, cells, tissues, and t issues with foreign substances such as an implant.

Compounds, Compositions and Assemblies

The synthetic nanomaterials described herein are not naturally occurring. The compositions have advantages over other nanomaterials, e.g., low toxicity, excellent biocompatibility and biodegradability due to their biomimetic structure.

The compositions are useful for multiple purposes that require biocompatibility. For example in certain embodiments, after the components/compounds are processed and incorporated with delivery cargos (such as small molecules, polypeptides and nucleic acids), these compounds form nanostructures (termed as "nanopieces"), which facilitate and promote drug delivery to target bodily tissues. Thus, the compounds can be used as nano-vectors for drug delivery, which could facilitate drug transportation into cells, tissues, and/or organs. For example, these nanostructures can be used to deliver nucleic acid drugs (e.g., small inhibitory RNA, microRNA, mRNA, DNA) into cells for therapeutics and diagnostics as well as for drug discovery and investigating new drug formulations. Thus, nanostructures described have significant advantages such as low toxicity when used for RNA/gene therapeutics or drug delivery techniques.

Another application of this invention is in research and development as a tool for delivering probes and chemical and biological compound for elucidating biological signaling pathway as well as identifying key molecular for a particular biological function in a research or clinical setting. The nanomaterials also serve biomimetic effects in medical devices or during tissue repair including surgery and/or tissue engineering. For example, the nanomaterial can be used to affect bio-adhesion between molecules, cells, tissues, and t issues with foreign substances such as an implant or other medical devices.

Modules according to the present disclosure include compounds of Formula (I) below:

(I)

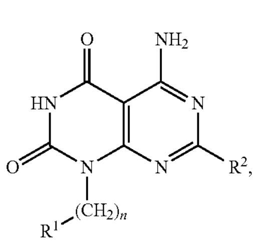

or a pharmaceutically acceptable salt, ester or amide thereof wherein, n is an integer of 0, 1, 2, 3, 4, 5 or 6;

$R^1$ is α-amino acid, β-amino acid, α-polypeptide, β-polypeptide,

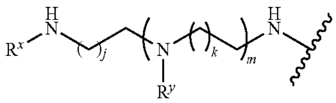

or

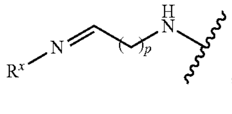

;

j, k, m and p are independently an integer of 0 to 20;

$R^x$ is aliphatic or H;

$R^y$ is H or

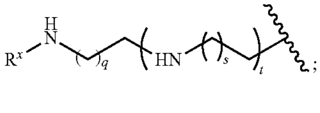

;

q, s and t are independently an integer of 0 to 20;

$R^2$ is H, $CH_3$ or $NHR_7$; and $R^2$ is H or aliphatic.

In embodiments, n is an integer of 1, 2, 3, 4, 5 or 6. In embodiments, n is 1, 2, 3, or 4. In embodiments, n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^1$ is an α-amino acid comprising a covalent bond between an α-amino group and $(CH_2)_r$. In embodiments, $R^1$ is a β-amino acid comprising a covalent bond between a β-amino group and $(CH_2)_r$. In embodiments, $R^1$ is an α polypeptide comprising a covalent bond between an α-amino group and $(CH_2)_r$. In embodiments, $R^1$ is a β-polypeptide comprising a covalent bond between a β-amino group and $(CH_2)_r$.

In another embodiment $R^1$ is an α- or β-amino acid, wherein the primary amino group within the amino acid backbone is covalently bound to the carbon atom of the $(CH_2)_n$-modified linker.

In embodiments, $R^1$ is a D-α-amino acid. In embodiments, $R^1$ is a L-α-amino acid. In embodiments, $R^1$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^1$ is lysine, arginine, serine, glycine, or aspartate.

In embodiments, $R^1$ is a D-β-amino acid. In embodiments, $R^1$ is a L-β-amino acid. In embodiments, $R^1$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^1$ is α-amino acid derivative of lysine, arginine, serine, glycine, or aspartate.

In a further embodiment $R^1$ is an α- or β-polypeptide, wherein the terminal amino group within the polypeptide backbone is covalently bound to the carbon atom of the $(CH_2)_n$-modified linker. In embodiments, $R^1$ is an α- or β-polypeptide comprising 1, 2, 3, 4, 5, 6, 7, 8, 9, or 10 amino acid residues. In embodiments, R' is an α- or β-polypeptide comprising 1, 2, 3, 4, or 5 amino acid residues.

Exemplary $R^1$ groups are shown below:

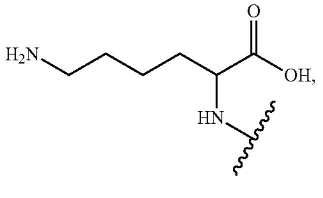

-continued
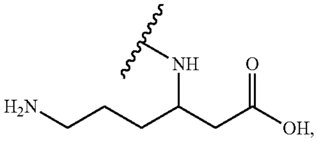
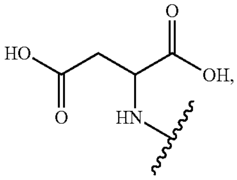
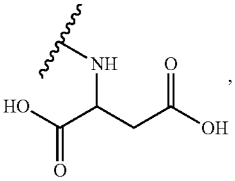
,
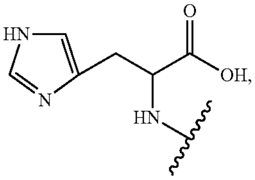
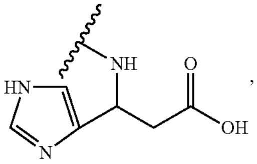
,
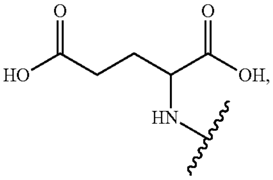
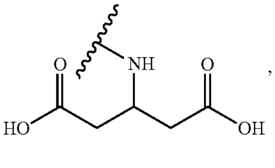
,
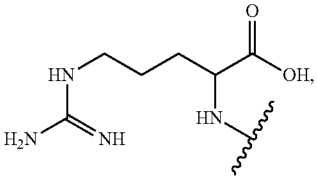
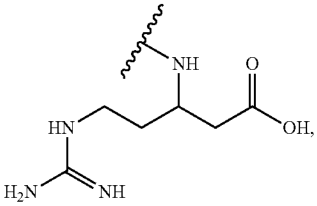
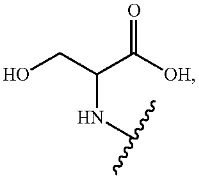
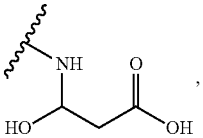
,
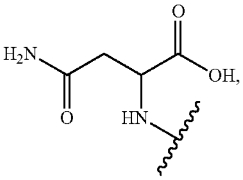
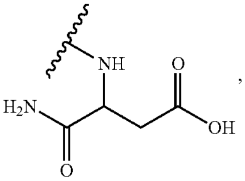
,
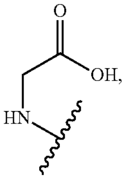
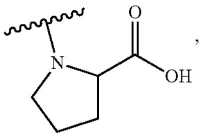
,
-continued
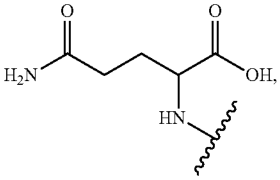
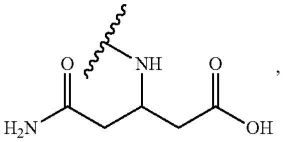
,
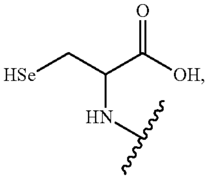
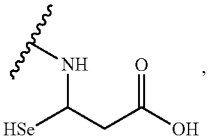
,
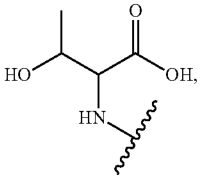
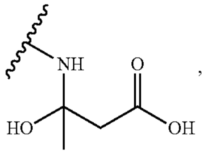
,
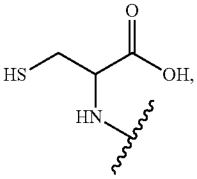
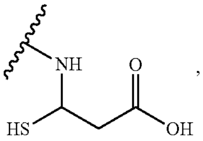
,
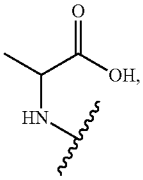
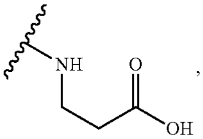
,
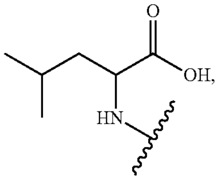
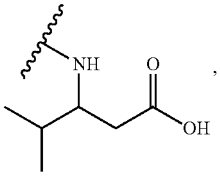
,
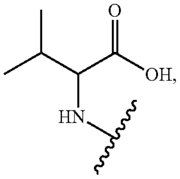
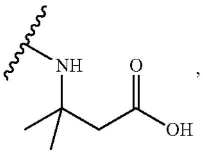
,
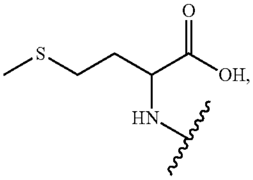
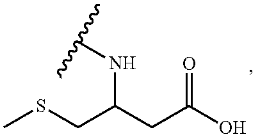
,
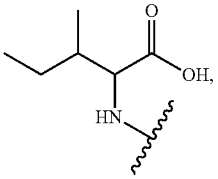
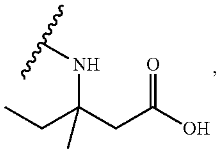
,
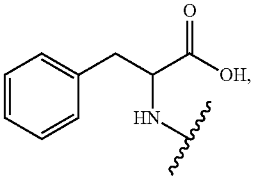

-continued

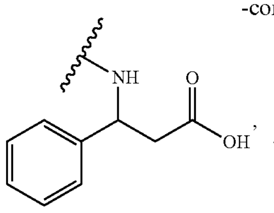,
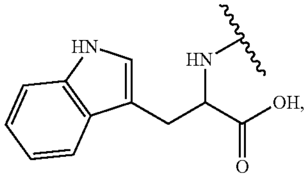,

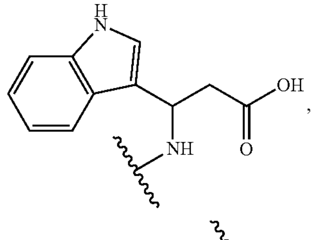,

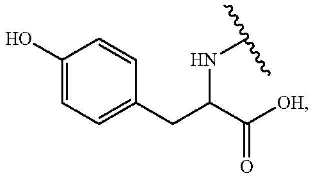, or

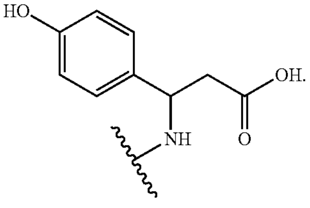.

In embodiments, $R^2$ is H. In embodiments, $R^2$ is $CH_3$. In embodiments, $R^2$ is $NHR_7$. In embodiments, $R^z$ is H. In embodiments, $R^z$ is aliphatic. In embodiments, $R^2$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

Modules according to the present disclosure also include compounds of Formula (II) below:

(II)

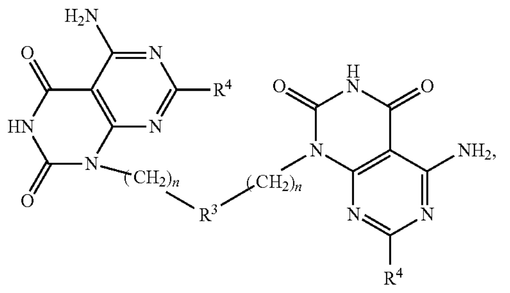

or a pharmaceutically acceptable salt, ester or amide thereof wherein, n is independently 1, 2, 3, 4, 5 or 6;

$R^3$ is an α-amino acid, β-amino acid, α-polypeptide, β-polypeptide,

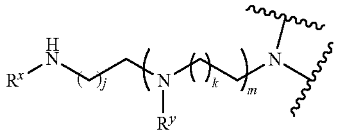 or

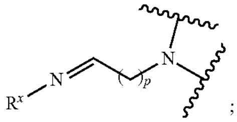;

j, k, m and p are independently an integer of 0 to 20;

$R^x$ is aliphatic or H;

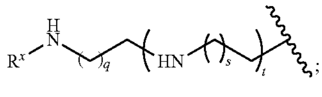;

$R^y$ is independently H or q, s and t are independently an integer of 0 to 20;

$R^4$ is independently H, $CH_3$, or $NHR_2$; and $R^z$ is independently H or aliphatic.

In embodiments, each n is independently 1, 2, 3, or 4. In embodiments, each n is independently 1 or 2. In embodiments, each n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^3$ is an α-amino acid comprising a covalent bond between an α-amino group and $(CH_2)_r$. In embodiments, $R^3$ is a β-amino acid comprising a covalent bond between a β-amino group and $(CH_2)$. In embodiments, $R^3$ is an α polypeptide comprising a covalent bond between an α-amino group and $(CH_2)_r$. In embodiments, $R^3$ is a β-polypeptide comprising a covalent bond between a β-amino group and $(CH_2)_r$.

In another embodiment $R^3$ is an α- or β-amino acid, wherein the primary amino group within the amino acid backbone is covalently bound to the carbon atom of the $(CH_2)_n$-modified linker.

In embodiments, $R^3$ is a D-α-amino acid. In embodiments, $R^3$ is a L-α-amino acid. In embodiments, $R^5$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^3$ is lysine, arginine, serine, glycine, or aspartate.

In embodiments, $R^3$ is a D-β-amino acid. In embodiments, $R^3$ is a L-β-amino acid. In embodiments, $R^3$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp. D), glutamate (Glu, E), γ-carboxyglutamate, asparagine (Asn, N), or glutamine (Gln, Q). In embodiments, $R^3$ is a β-amino acid derivative of lysine, arginine, serine, glycine, or aspartate.

In a further embodiment $R^3$ is an α- or β-polypeptide, wherein the terminal amino group within the polypeptide backbone is covalently bound to the carbon atom of the $(CH_2)_n$-modified linker. In embodiments, $R^3$ is an α- or β-polypeptide comprising 1, 2, 3, 4, 5, 6, 7, 8, 9, or 10 amino acid residues. In embodiments, $R^3$ is α- or β-polypeptide comprising 1, 2, 3, 4, or 5 amino acid residues.

In another embodiment $R^3$ is α- or β-amino acid, wherein the primary amino group within the amino acid backbone is covalently bound to the carbon atom of the $(CH_2)_n$-modified linker.

In embodiments, $R^4$ is H. In embodiments, $R^4$ is $CH_3$. In embodiments, $R^4$ is $NHR^z$. In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In another embodiment $R^3$ is an α- or β-amino acid, wherein the primary amino group within the amino acid backbone is covalently bound to the carbon atom of the $(CH_2)_n$-modified linkers.

In a further embodiment $R^3$ is an α- or β-polypeptide, wherein the terminal amino group within the polypeptide backbone is covalently bound to the carbon atom of the $(CH_2)_n$-modified linkers.

Exemplary $R^3$ groups are shown in the formula below:

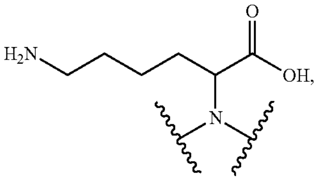

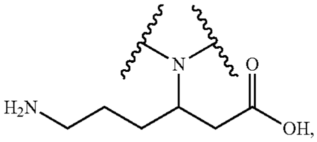

-continued

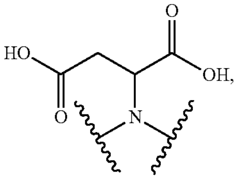 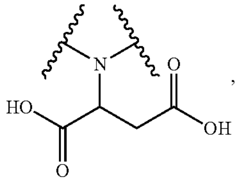 ,

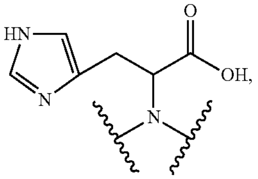 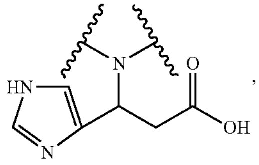 ,

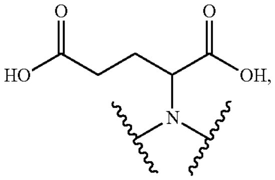 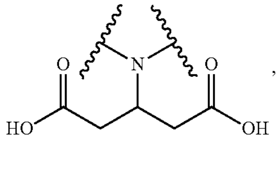 ,

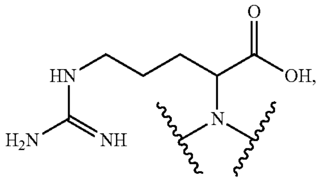

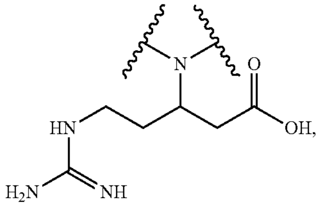

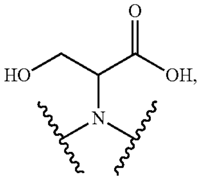 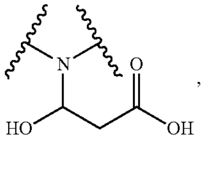 ,

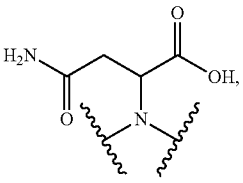 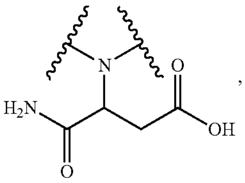 ,

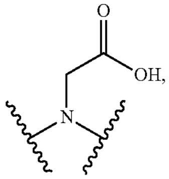 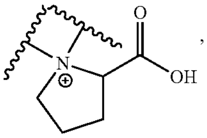 ,

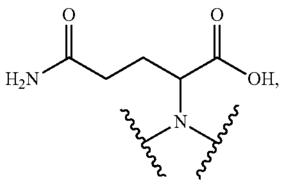 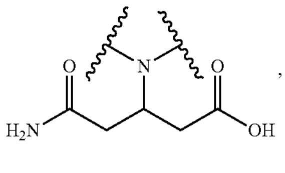 ,

-continued

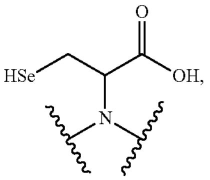 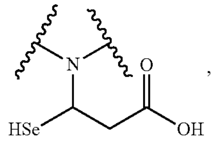,

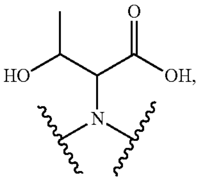 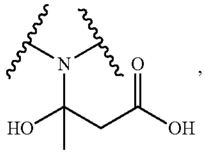,

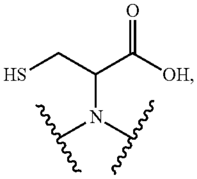 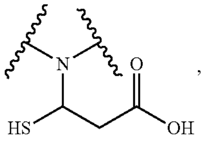, 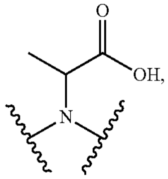

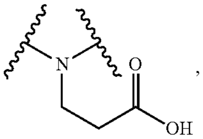, 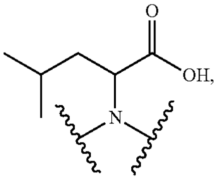

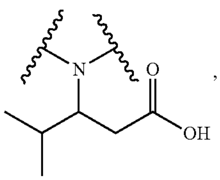, 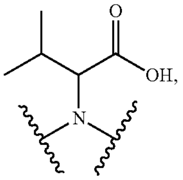

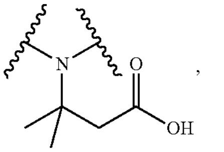, 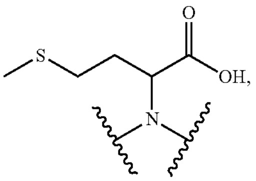

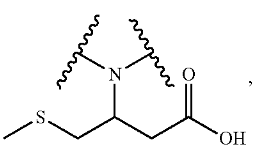, 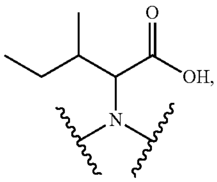

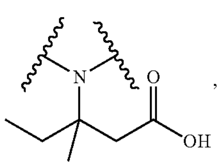, 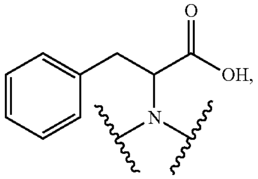

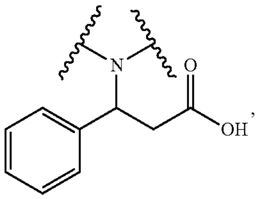, 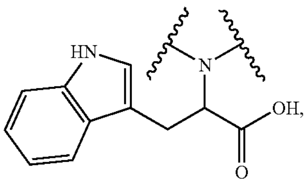

-continued

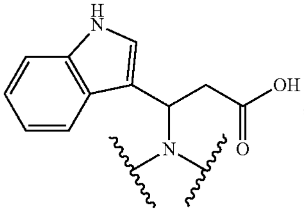,

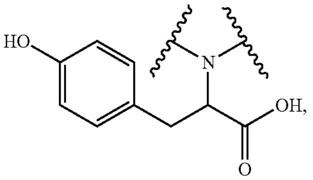 or

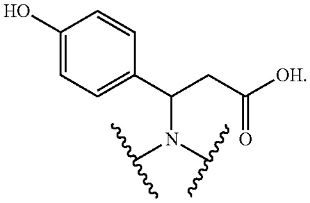

Modules according to the present disclosure include compounds of Formula (III) below:

(III)

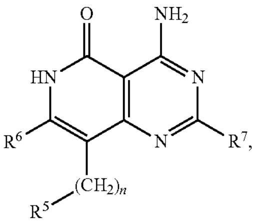

or a pharmaceutically acceptable salt, ester or amide thereof wherein, n is an integer of, 0, 2, 3, 4, 5 or 6;

$R^5$ is α-amino acid, β-amino acid, α-polypeptide, β-polypeptide,

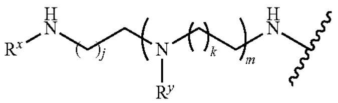 or

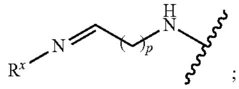;

j, k, m and p are independently an integer of 0 to 20;

$R^x$ is aliphatic or H;

$R^y$ is H or

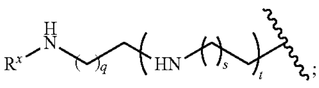;

q, s and t are independently an integer of 0 to 20;

$R^6$ and $R^7$ are independently selected from hydrogen, $CH_3$, or $NHR^z$; and $R^2$ is H or aliphatic.

In embodiments, n is an integer of 1, 2, 3, 4, 5 or 6. In embodiments, n is 1, 2, 3, or 4. In embodiments, n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^5$ is an α-amino acid comprising a covalent bond between an α-amino group and $(CH_2)_r$. In embodiments, $R^5$ is a β-amino acid comprising a covalent bond between a β-amino group and $(CH_2)_r$. In embodiments, $R^5$ is an α polypeptide comprising a covalent bond between an α-amino group and $(CH_2)_r$. In embodiments, $R^5$ is a β-polypeptide comprising a covalent bond between a β-amino group and $(CH_2)_r$.

In another embodiment $R^5$ is an α- or β-amino acid, wherein the primary amino group within the amino acid backbone is covalently bound to the carbon atom of the $(CH_2)_n$-modified linker.

In embodiments, $R^5$ is a D-α-amino acid. In embodiments, $R^5$ is a L-α-amino acid. In embodiments, $R^5$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^5$ is lysine, arginine, serine, glycine, or aspartate.

In embodiments, $R^5$ is a D-β-amino acid. In embodiments, $R^5$ is a L-β-amino acid. In embodiments, $R^5$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^3$ is a β-amino acid derivative of lysine, arginine, serine, glycine, or aspartate.

In a further embodiment $R^5$ is an α- or β-polypeptide, wherein the terminal amino group within the polypeptide backbone is covalently bound to the carbon atom of the $(CH_2)_n$-modified linker. In embodiments, $R^3$ is an α- or β-polypeptide comprising 1, 2, 3, 4, 5, 6, 7, 8, 9, or 10 amino acid residues. In embodiments, $R^5$ is α- or β-polypeptide comprising 1, 2, 3, 4, or 5 amino acid residues.

In another embodiment $R^5$ is α- or β-amino acid, wherein the primary amino group within the amino acid backbone is covalently bound to the carbon atom of the $(CH_2)_n$-modified linker.

In embodiments, $R^7$ is H. In embodiments, $R^7$ is $CH_3$. In embodiments, $R^7$ is $NHR^z$. In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

Exemplary $R^5$ groups are shown in the formula below:

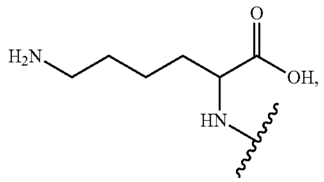

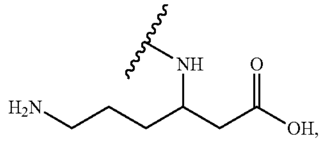

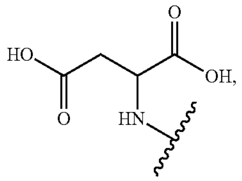 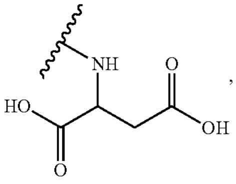 ,

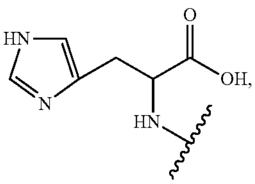 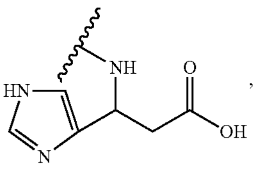 ,

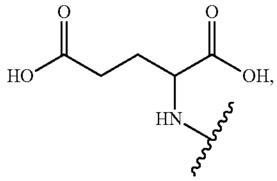 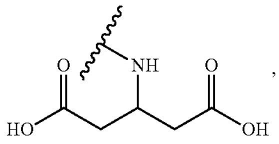 ,

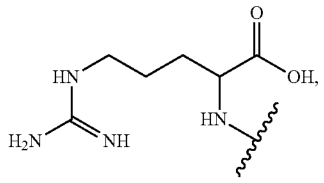

-continued
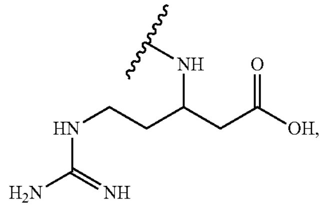
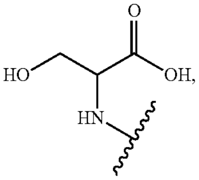
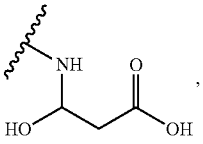
,
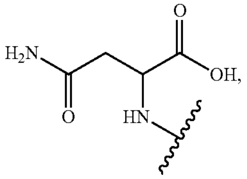
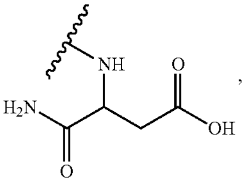
,
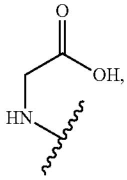
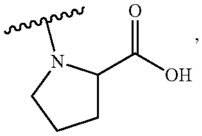
,
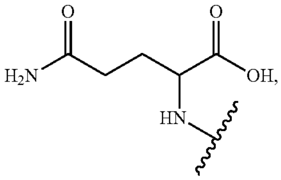
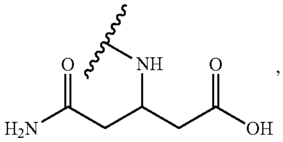
,
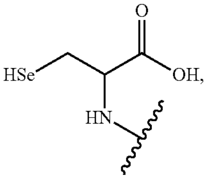
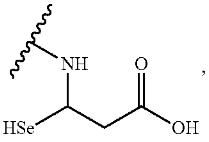
,
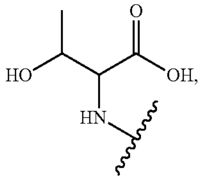
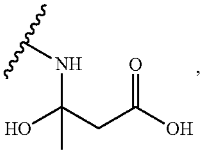
,
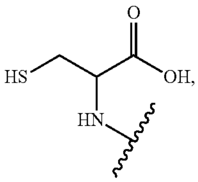
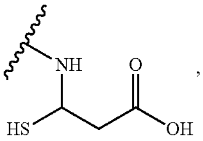
,
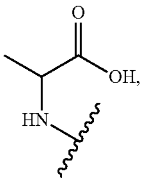
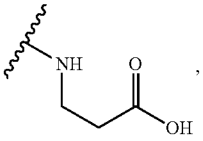
,
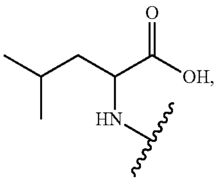
-continued
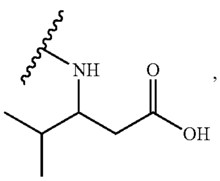
,
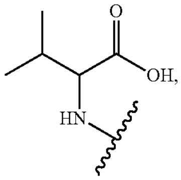
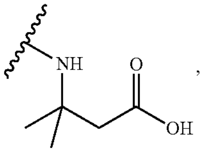
,
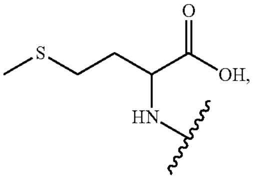
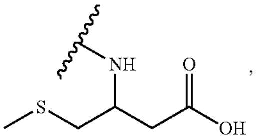
,
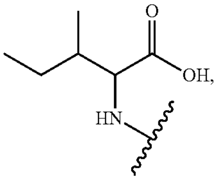
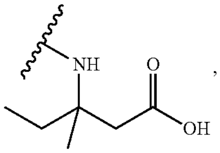
,
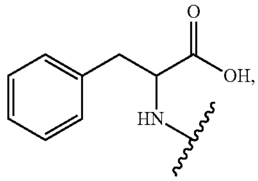
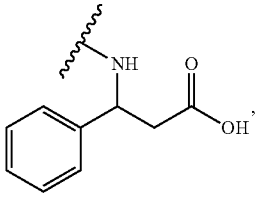
,
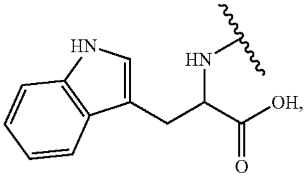
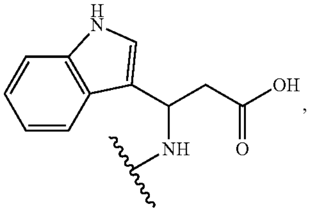
,
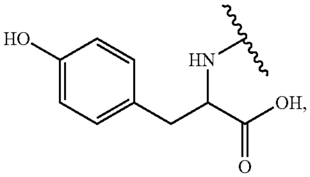
or
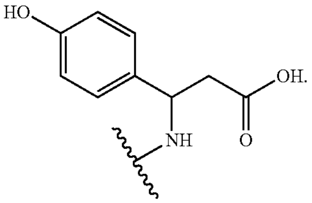

Modules according to the present disclosure also include compounds of Formula IV below:

(IV)

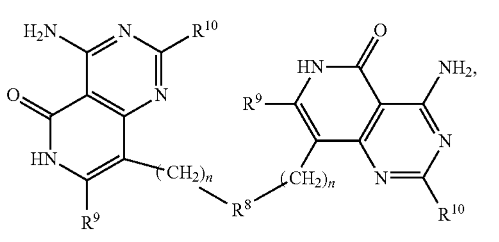

or a pharmaceutically acceptable salt or ester thereof wherein, n is 1, 2, 3, 4, 5 or 6;

$R^8$ is an α-amino acid, β-amino acid, α-polypeptide, β-polypeptide,

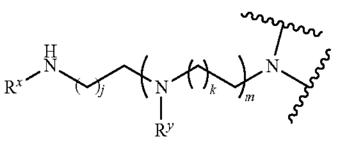

or

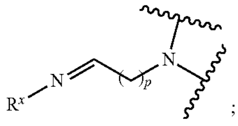

;

j, k, m and p are independently an integer of 1 to 20;

$R^x$ is aliphatic or H;

$R^y$ is H or

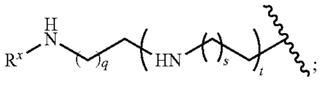

;

q, s and t are independently an integer of 1 to 20;

each $R^9$ and $R^{10}$ is independently selected from hydrogen, $CH_3$, or $NHR_7$; and $R^z$ is H or aliphatic.

In embodiments, each n is independently 1, 2, 3, or 4. In embodiments, each n is independently 1 or 2. In embodiments, each n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^8$ is an α-amino acid comprising a covalent bond between an α-amino group and $(CH_2)_r$. In embodiments, $R^2$ is a β-amino acid comprising a covalent bond between a β-amino group and $(CH_2)_r$. In embodiments, $R^8$ is an α polypeptide comprising a covalent bond between an α-amino group and $(CH_2)_r$. In embodiments, $R^8$ is a β-polypeptide comprising a covalent bond between a β-amino group and $(CH_2)_r$.

In another embodiment $R^8$ is an α- or β-amino acid, wherein the primary amino group within the amino acid backbone is covalently bound to the carbon atom of the $(CH_2)_n$-modified linker.

In embodiments, $R^8$ is a D-α-amino acid. In embodiments, $R^8$ is a L-α-amino acid. In embodiments, $R^5$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^8$ is lysine, arginine, serine, glycine, or aspartate.

In embodiments, $R^8$ is a D-β-amino acid. In embodiments, $R^8$ is a L-β-amino acid. In embodiments, $R^8$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^8$ is a β-amino acid derivative of lysine, arginine, serine, glycine, or aspartate.

In a further embodiment $R^8$ is an α- or β-polypeptide, wherein the terminal amino group within the polypeptide backbone is covalently bound to the carbon atom of the $(CH_2)_n$-modified linker. In embodiments, $R^8$ is an α- or β-polypeptide comprising 1, 2, 3, 4, 5, 6, 7, 8, 9, or 10 amino acid residues. In embodiments, $R^8$ is α- or β-polypeptide comprising 1, 2, 3, 4, or 5 amino acid residues.

In another embodiment $R^8$ is α- or β-amino acid, wherein the primary amino group within the amino acid backbone is covalently bound to the carbon atom of the $(CH_2)_n$-modified linker.

In embodiments, $R^9$ is H. In embodiments, $R^9$ is $CH_3$. In embodiments, $R^9$ is $NHR_2$. In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^{10}$ is H. In embodiments, $R^{10}$ is $CH_3$. In embodiments, $R^{10}$ is $NHR^z$. In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In another embodiment $R^8$ is an α- or β-amino acid, wherein the primary amino group within the amino acid backbone is covalently bound to the carbon atom of the $(CH_2)_n$-modified linkers.

In a further embodiment $R^8$ is an α- or β-polypeptide, wherein the terminal amino group within the polypeptide backbone is covalently bound to the carbon atom of the $(CH_2)_n$-modified linkers.

Exemplary $R^8$ groups are shown in the formula below:

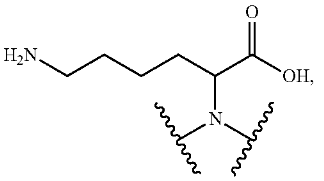

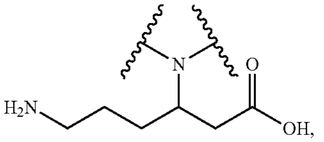

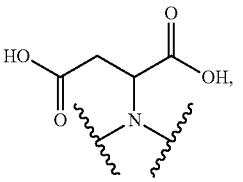 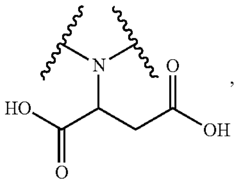 ,

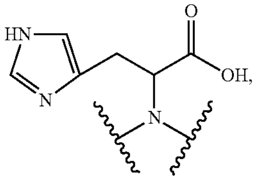 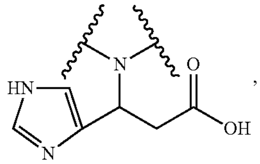 ,

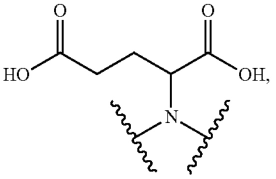 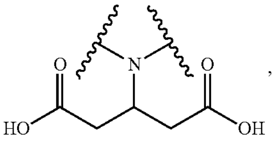 ,

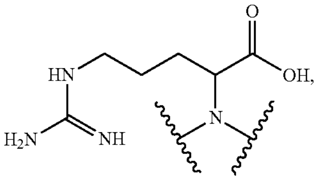

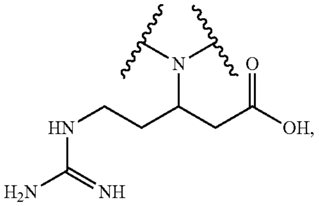

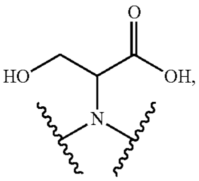 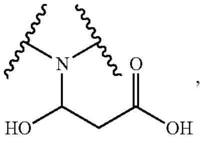 ,

-continued

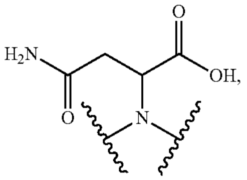 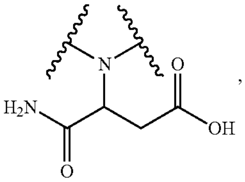 ,

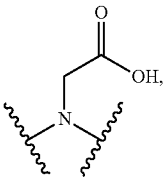 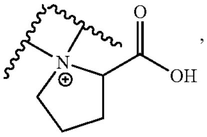 ,

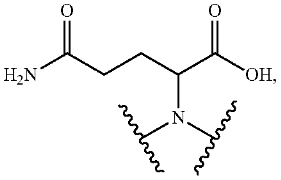 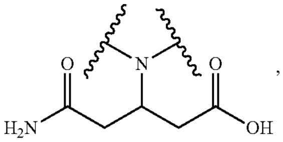 ,

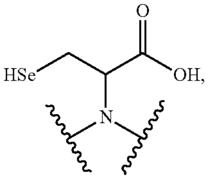 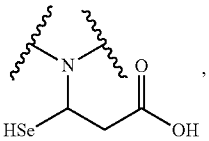 ,

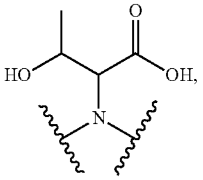 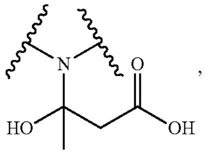 ,

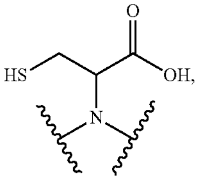 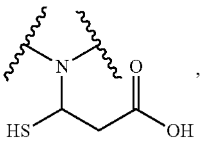 , 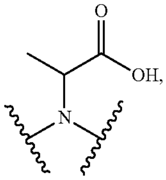

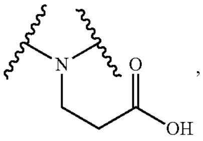 , 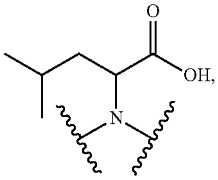

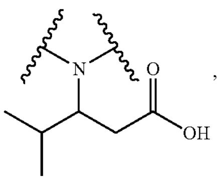 , 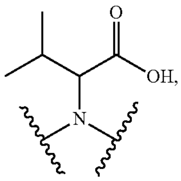

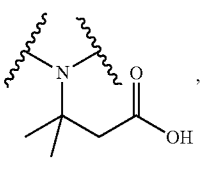 , 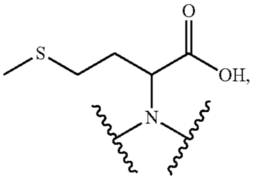

-continued

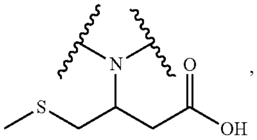,
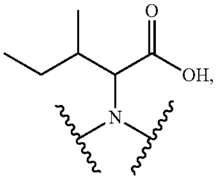

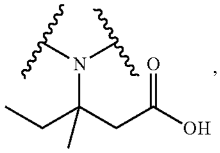,
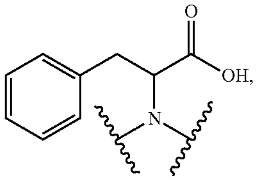

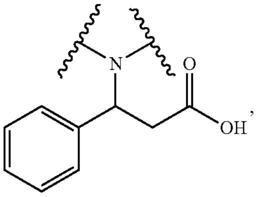,
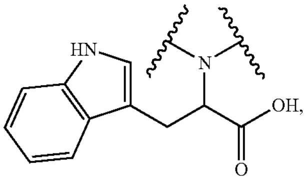

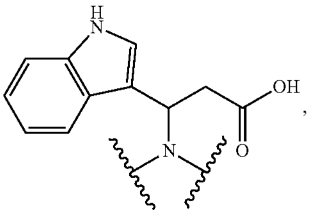,

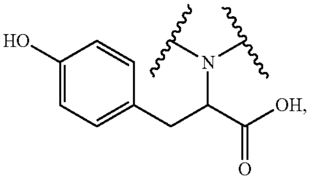 or

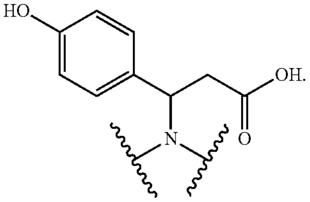

Modules according to the present disclosure include compounds of Formula V below:

(V)

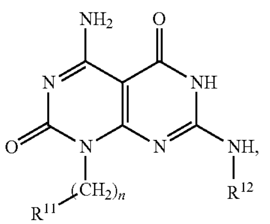

or a pharmaceutically acceptable salt, ester or amide thereof wherein, n is an integer of, 1, 2, 3, 4, 5 or 6;

$R^{11}$ is β-amino acid, β-polypeptide,

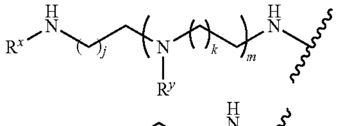 or

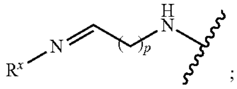;

j, k, m and p are independently an integer of 1 to 20;

$R^x$ is aliphatic or H;

$R^y$ is H of

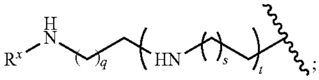;

q, s and t are independently an integer of 1 to 20; and $R^{12}$ is H or aliphatic.

In embodiments, n is an integer of 1, 2, 3, 4, 5 or 6. In embodiments, n is 1, 2, 3, or 4. In embodiments, n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^{11}$ is a β-amino acid comprising a covalent bond between a β-amino group and $(CH_2)_r$. In embodiments, $R^{11}$ is a β-polypeptide comprising a covalent bond between a β-amino group and $(CH_2)_r$.

In another embodiment $R^{11}$ is a β-amino acid, wherein the primary amino group within the amino acid backbone is covalently bound to the carbon atom of the $(CH_2)_n$-modified linker.

In embodiments, $R^{11}$ is a D-β-amino acid. In embodiments, $R^{11}$ is a L-β-amino acid. In embodiments, $R^{11}$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{11}$ is a β-amino acid derivative of lysine, arginine, serine, glycine, or aspartate.

In a further embodiment $R^{11}$ is a β-polypeptide, wherein the terminal amino group within the polypeptide backbone is covalently bound to the carbon atom of the $(CH_2)_n$-modified linker. In embodiments, $R^{11}$ is an α- or β-polypeptide comprising 1, 2, 3, 4, 5, 6, 7, 8, 9, or 10 amino acid residues. In embodiments, $R^{11}$ is α- or β-polypeptide comprising 1, 2, 3, 4, or 5 amino acid residues.

In another embodiment $R^{11}$ is β-amino acid, wherein the primary amino group within the amino acid backbone is covalently bound to the carbon atom of the $(CH_2)_n$-modified linker.

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In embodiments, $R^{12}$ is H. In embodiments, $R^{12}$ is aliphatic. In embodiments, $R^{12}$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In another embodiment $R^1$ is α- or β-amino acid, wherein the primary amino group within the amino acid backbone is covalently bound to the carbon atom of the $(CH_2)_n$-modified linker.

In a further embodiment $R^{11}$ is a β-polypeptide, wherein the terminal amino group within the polypeptide backbone is covalently bound to the carbon atom of the $(CH_2)_n$-modified linker.

Exemplary $R^{11}$ groups are shown in the formula below:

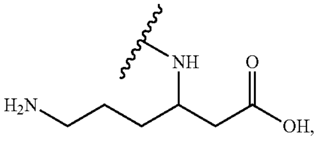,

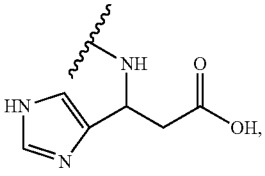,

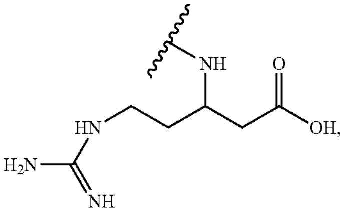, 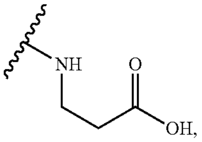,

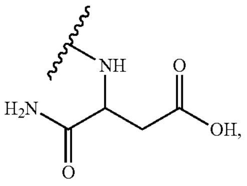, 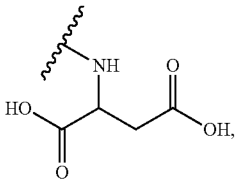,

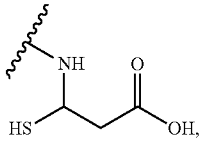, 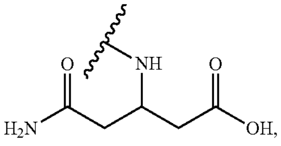,

-continued

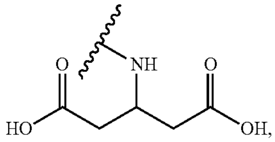, 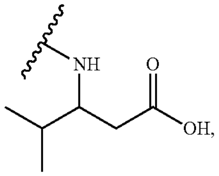,

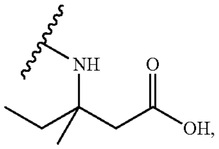, 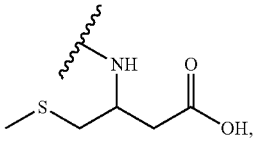,

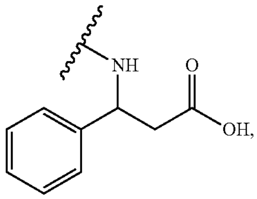, 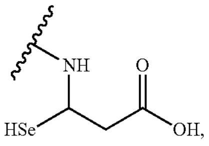,

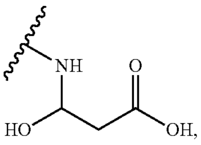, 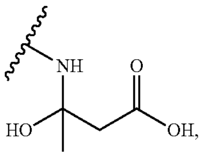,

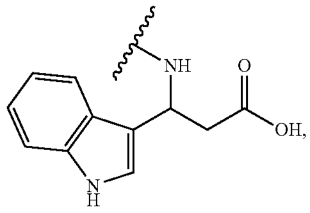,

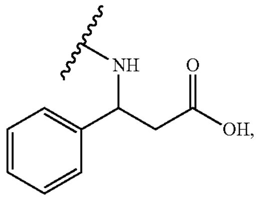, or 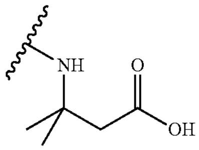

Modules according to the present disclosure also include compounds of Formula VI below:

(VI)

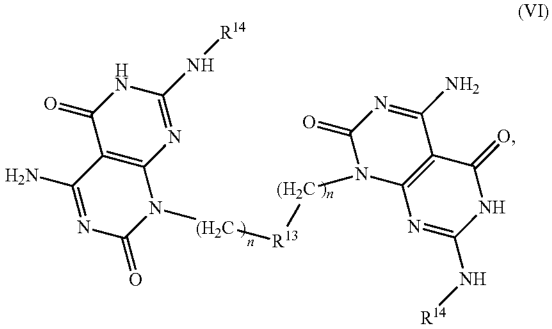

or a pharmaceutically acceptable salt, ester or amide thereof wherein, n is 1, 2, 3, 4, 5 or 6;

$R^{13}$ is a β-amino acid, β-polypeptide,

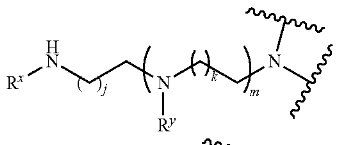
or

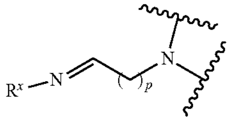
;

j, k, m and p are independently an integer of 1 to 20;

$R^x$ is aliphatic or H;

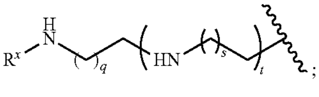
;

$R^y$ is H or q, s and t are independently an integer of 1 to 20; and $R^{14}$ is H or aliphatic.

In embodiments, each n is independently 1, 2, 3, or 4. In embodiments, each n is independently 1 or 2. In embodiments, each n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20, and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^{13}$ is a β-amino acid comprising a covalent bond between a β-amino group and $(CH_2)_r$. In embodiments, $R^{13}$ is a β-polypeptide comprising a covalent bond between a β-amino group and $(CH_2)_r$.

In another embodiment $R^{13}$ is a β-amino acid, wherein the primary amino group within the amino acid backbone is covalently bound to the carbon atom of the $(CH_2)_n$-modified linker.

In embodiments, $R^{13}$ is a D-β-amino acid. In embodiments, $R^{13}$ is a L-β-amino acid. In embodiments, $R^{13}$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{13}$ is a β-amino acid derivative of lysine, arginine, serine, glycine, or aspartate.

In a further embodiment $R^{13}$ is a β-polypeptide, wherein the terminal amino group within the polypeptide backbone is covalently bound to the carbon atom of the $(CH_2)_n$-modified linker. In embodiments, $R^{13}$ is α-polypeptide comprising 1, 2, 3, 4, 5, 6, 7, 8, 9, or 10 amino acid residues. In embodiments, $R^{13}$ is β-polypeptide comprising 1, 2, 3, 4, or 5 amino acid residues.

In another embodiment $R^{13}$ is β-amino acid, wherein the primary amino group within the amino acid backbone is covalently bound to the carbon atom of the $(CH_2)_n$-modified linker.

In embodiments, $R^{14}$ is H. In embodiments, $R^{14}$ is $CH_3$. In embodiments, $R^{14}$ is $NHR^z$. In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In another embodiment $R^{13}$ is an α- or β-amino acid, wherein the primary amino group within the amino acid backbone is covalently bound to the carbon atom of the $(CH_2)_n$-modified linkers.

In a further embodiment $R^{13}$ is an α- or β-polypeptide, wherein the terminal amino group within the polypeptide backbone is covalently bound to the carbon atom of the $(CH_2)$, modified linkers.

Exemplary $R^{13}$ groups are shown in the formula below:

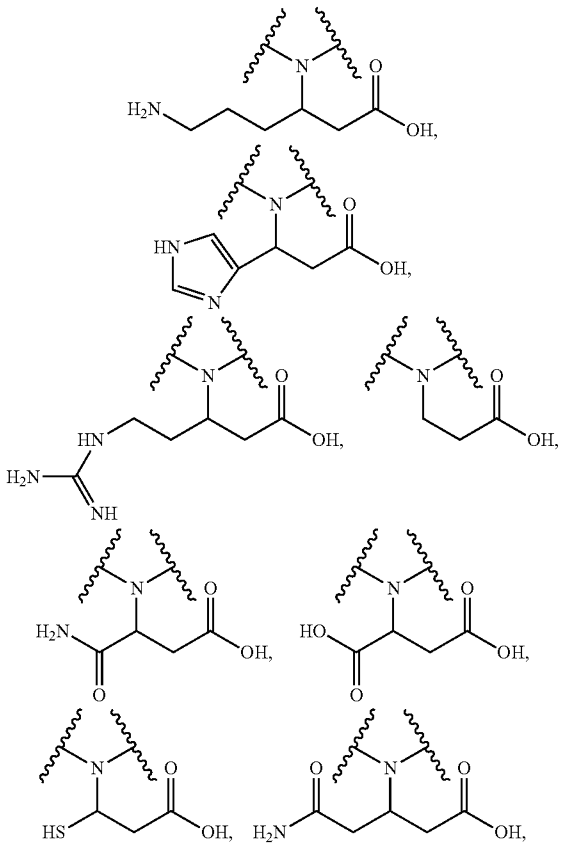

-continued

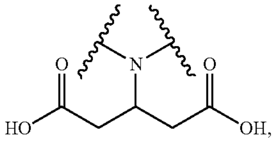 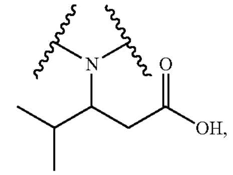

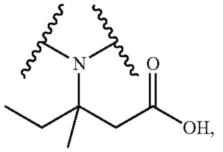 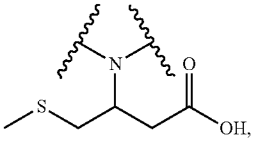

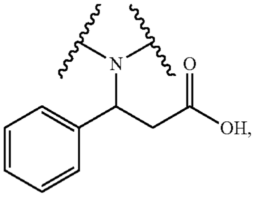 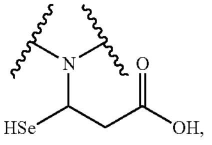

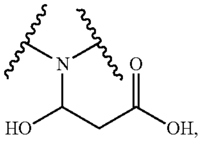 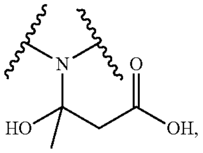

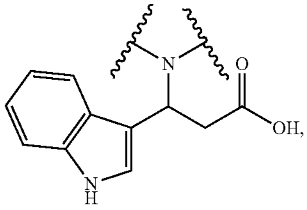

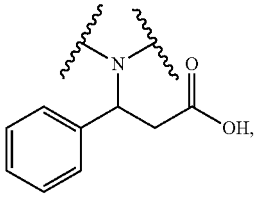 or 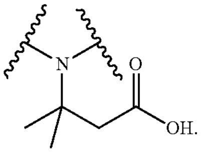

Modules according to the present disclosure include compounds of Formula VII below:

(VII)

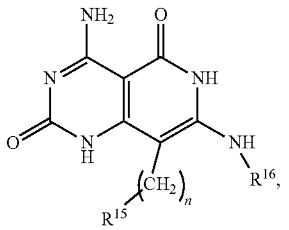

or a pharmaceutically acceptable salt, ester or amide thereof wherein, n is an integer of, 1, 2, 3, 4, 5 or 6;

$R^{15}$ is α-amino acid, β-amino acid, α-polypeptide, β-polypeptide,

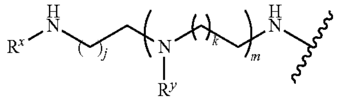 or

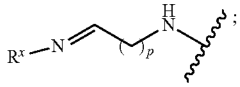;

j, k, m and p are independently an integer of 1 to 20;

$R^x$ is aliphatic or H;

$R^y$ is H or

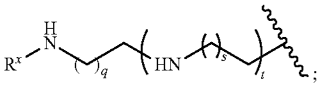;

q, s and t are independently an integer of 1 to 20; and $R^{16}$ is H or aliphatic.

In embodiments, n is an integer of 1, 2, 3, 4, 5 or 6. In embodiments, n is 1, 2, 3, or 4. In embodiments, n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^{15}$ is an α-amino acid comprising a covalent bond between an α-amino group and $(CH_2)_r$. In embodiments, $R^{15}$ is a β-amino acid comprising a covalent bond between a β-amino group and $(CH_2)$. In embodiments, $R^{15}$ is an α polypeptide comprising a covalent bond between an α-amino group and $(CH_2)_r$. In embodiments, $R^{15}$ is a β-polypeptide comprising a covalent bond between a β-amino group and $(CH_2)_r$.

In another embodiment $R^{15}$ is an α- or β-amino acid, wherein the primary amino group within the amino acid backbone is covalently bound to the carbon atom of the $(CH_2)_n$-modified linker.

In embodiments, $R^{15}$ is a D-α-amino acid. In embodiments, $R^{15}$ is a L-α-amino acid. In embodiments, $R^{15}$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{15}$ is lysine, arginine, serine, glycine, or aspartate.

In embodiments, $R^{15}$ is a D-β-amino acid. In embodiments, $R^{15}$ is a L-β-amino acid. In embodiments, $R^{15}$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{15}$ is a β-amino acid derivative of lysine, arginine, serine, glycine, or aspartate.

In a further embodiment $R^{15}$ is an α- or β-polypeptide, wherein the terminal amino group within the polypeptide backbone is covalently bound to the carbon atom of the $(CH_2)_n$-modified linker. In embodiments, $R^{15}$ is an α- or β-polypeptide comprising 1, 2, 3, 4, 5, 6, 7, 8, 9, or 10 amino acid residues. In embodiments, $R^{15}$ is α- or β-polypeptide comprising 1, 2, 3, 4, or 5 amino acid residues.

In another embodiment $R^{15}$ is α- or β-amino acid, wherein the primary amino group within the amino acid backbone is covalently bound to the carbon atom of the $(CH_2)_n$-modified linker.

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In embodiments, $R^{16}$ is H. In embodiments, $R^{16}$ is aliphatic. In embodiments, $R^{16}$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In another embodiment $R^{15}$ is an α- or β-amino acid, wherein the primary amino group within the amino acid backbone is covalently bound to the carbon atom of the $(CH_2)$-modified linker.

In a further embodiment $R^{15}$ is an α- or β-polypeptide, wherein the terminal amino group within the polypeptide backbone is covalently bound to the carbon atom of the $(CH_2)_n$-modified linker.

Exemplary $R^{15}$ groups are shown in the formula below:

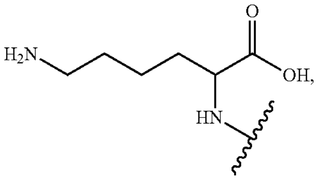

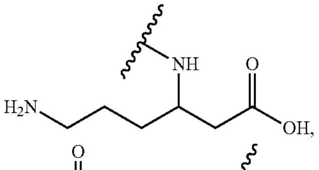

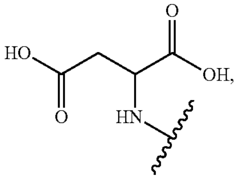

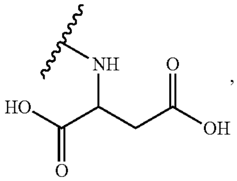

,

-continued

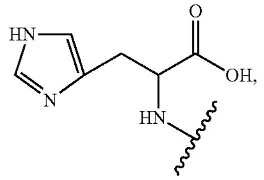

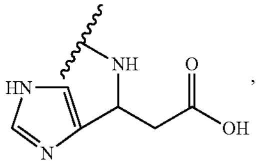

,

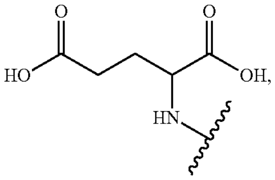

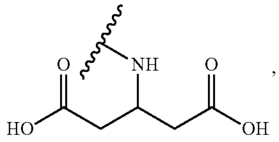

,

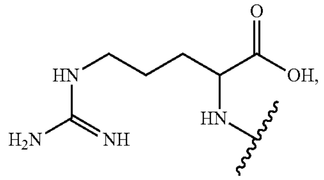

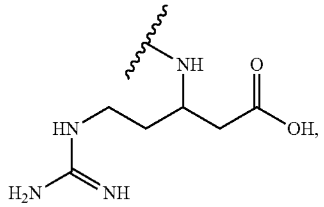

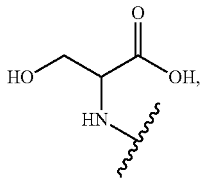

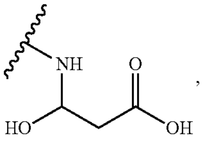

,

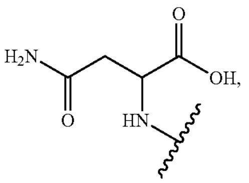

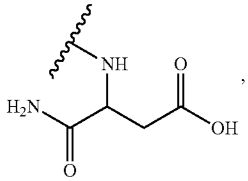

,

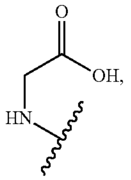

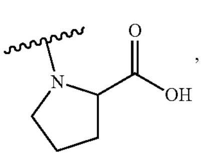

,

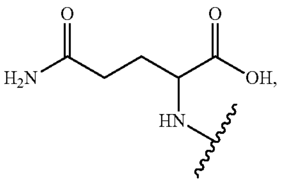

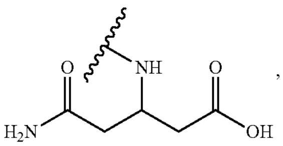

,

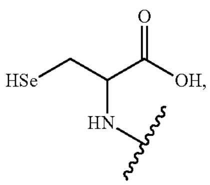

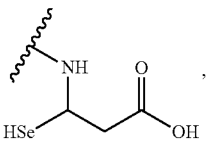

,

-continued

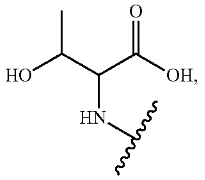

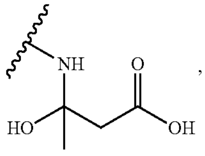

,

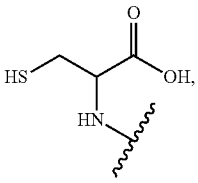

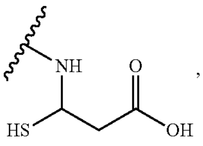

,

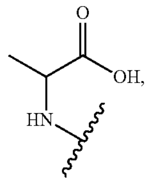

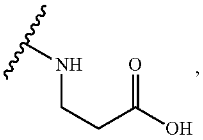

,

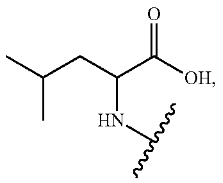

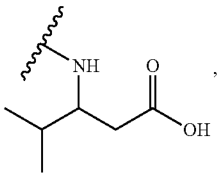

,

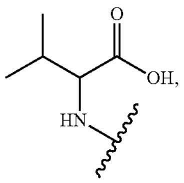

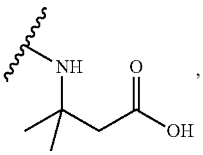

,

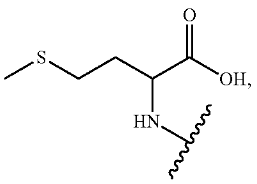

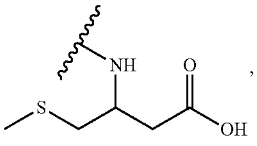

,

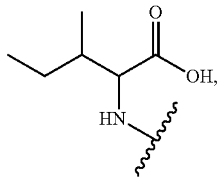

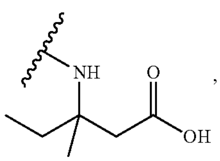

,

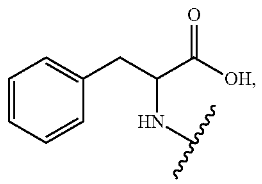

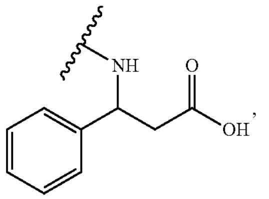

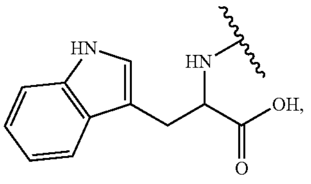

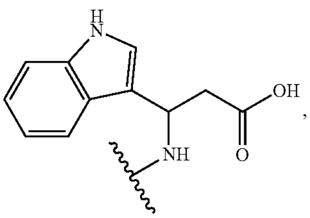

,

-continued

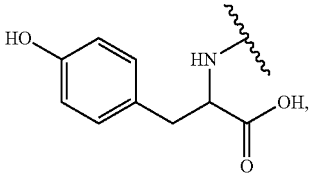

or

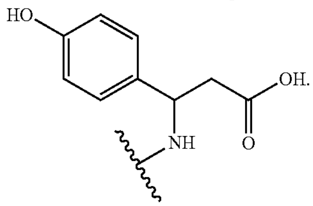

Modules according to the present disclosure also include compounds of Formula VIII below:

(VIII)

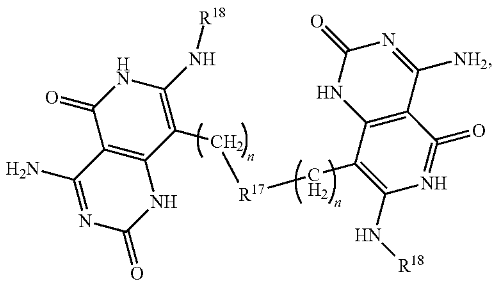

or a pharmaceutically acceptable salt, ester or amide thereof wherein, n is 1, 2, 3, 4, 5 or 6;

$R^{17}$ is an α-amino acid, β-amino acid, α-polypeptide, β-polypeptide,

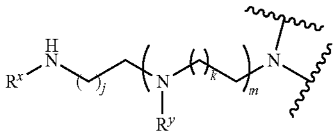

or

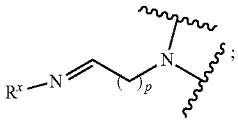

;

j, k, m and p are independently an integer of 1 to 20;

$R^x$ is aliphatic or H;

$R^y$ is H or

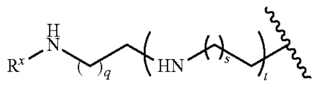

;

q, s and t are independently an integer of 1 to 20; and $R^{18}$ is H or aliphatic.

In embodiments, each n is independently 1, 2, 3, or 4. In embodiments, each n is independently 1 or 2. In embodiments, each n is 2.

In embodiments, j, k, m and p are independently an integer of 0 to 20 (e.g., j is independently 0, 1, 2, 3, 4, 5, 6, 7, 8, 9, 10, 11, 12, 13, 14, 15, 16, 17, 18, 19 or 20; k is independently 0, 1, 2, 3, 4, 5, 6, 7, 8, 9, 10, 11, 12, 13, 14, 15, 16, 17, 18, 19 or 20; m is independently 0, 1, 2, 3, 4, 5, 6, 7, 8, 9, 10, 11, 12, 13, 14, 15, 16, 17, 18, 19 or 20; and p is independently 0, 1, 2, 3, 4, 5, 6, 7, 8, 9, 10, 11, 12, 13, 14, 15, 16, 17, 18, 19 or 20). In embodiments, j, k, m, and p are independently an integer of 1 to 20. In embodiments, j, k, m and p are independently 1, 2, 3, 4, 5, or 6. In embodiments, j, k, m and p are independently 1, 2, 3, or 4.

In embodiments, q, s and t are independently an integer of 0 to 20 (e.g., q is independently 0, 1, 2, 3, 4, 5, 6, 7, 8, 9, 10, 11, 12, 13, 14, 15, 16, 17, 18, 19 or 20; s is independently 0, 1, 2, 3, 4, 5, 6, 7, 8, 9, 10, 11, 12, 13, 14, 15, 16, 17, 18, 19 or 20; and t is independently 0, 1, 2, 3, 4, 5, 6, 7, 8, 9, 10, 11, 12, 13, 14, 15, 16, 17, 18, 19 or 20). In embodiments, j q, s and t are independently an integer of 1 to 20. In embodiments, q, s and t are independently 1, 2, 3, 4, 5, or 6. In embodiments, q, s and t are independently 1, 2, 3, or 4.

In embodiments, $R^{17}$ is an α-amino acid comprising a covalent bond between an α-amino group and $(CH_2)_r$. In embodiments, $R^{17}$ is a β-amino acid comprising a covalent bond between a β-amino group and $(CH_2)_r$. In embodiments, $R^{17}$ is an α polypeptide comprising a covalent bond between an α-amino group and $(CH_2)_r$. In embodiments, $R^{17}$ is a β-polypeptide comprising a covalent bond between a β-amino group and $(CH_2)_r$.

In another embodiment $R^{17}$ is an α- or β-amino acid, wherein the primary amino group within the amino acid backbone is covalently bound to the carbon atom of the $(CH_2)_n$-modified linker.

In embodiments, $R^{17}$ is a D-α-amino acid. In embodiments, $R^{17}$ is a L-α-amino acid. In embodiments, $R^5$ is glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{17}$ is lysine, arginine, serine, glycine, or aspartate.

In embodiments, $R^{17}$ is a D-β-amino acid. In embodiments, $R^{17}$ is a L-β-amino acid. In embodiments, $R^{17}$ is a β-amino acid derivative of glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), or glutamine (Gln, Q). In embodiments, $R^{17}$ is a β-amino acid derivative of lysine, arginine, serine, glycine, or aspartate.

In a further embodiment $R^{17}$ is an α- or β-polypeptide, wherein the terminal amino group within the polypeptide backbone is covalently bound to the carbon atom of the $(CH_2)_n$-modified linker. In embodiments, $R^{17}$ is an α- or β-polypeptide comprising 1, 2, 3, 4, 5, 6, 7, 8, 9, or 10 amino acid residues. In embodiments, $R^{17}$ is α- or β-polypeptide comprising 1, 2, 3, 4, or 5 amino acid residues.

In another embodiment $R^{17}$ is α- or β-amino acid, wherein the primary amino group within the amino acid backbone is covalently bound to the carbon atom of the $(CH_2)_n$-modified linker.

In embodiments, $R^{18}$ is H. In embodiments, $R^{18}$ is $CH_3$. In embodiments, $R^{18}$ is $NHR^z$, In embodiments, $R^z$ is H. In embodiments, $R^z$ is aliphatic. In embodiments, $R^z$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic).

In embodiments, $R^x$ is aliphatic. In embodiments, $R^x$ is a substituted or unsubstituted group selected from alkyl, alkenyl, alkynyl, and/or carbocyclic (e.g., a substituted or unsubstituted group selected from $C_1$-$C_6$ alkyl, $C_2$-$C_6$ alkenyl, $C_2$-$C_6$ alkynyl, and/or $C_3$-$C_8$ carbocyclic). In embodiments, $R^x$ is H.

In another embodiment $R^{17}$ is α- or β-amino acid, wherein the primary amino group within the amino acid backbone is covalently bound to the carbon atom of the $(CH_2)_n$-modified linkers.

In a further embodiment $R^{17}$ is an α- or β-polypeptide, wherein the terminal amino group within the polypeptide backbone is covalently bound to the carbon atom of the $(CH_2)_n$-modified linkers.

Exemplary $R^{17}$ groups are shown in the formula below:

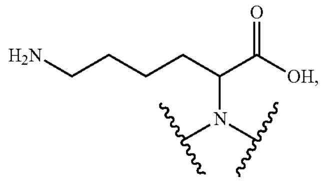

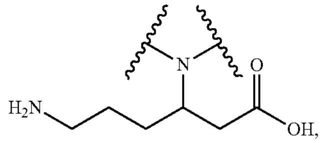

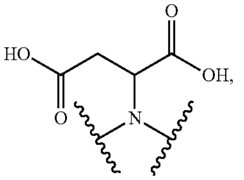
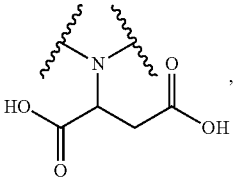
,

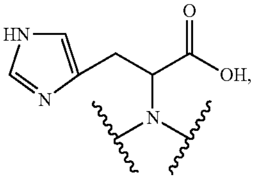
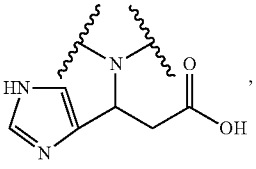
,

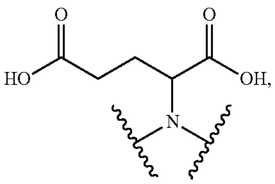
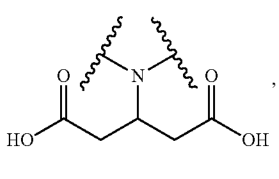
,

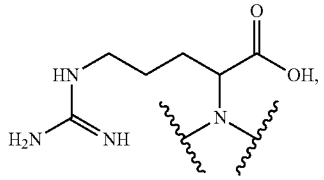

-continued
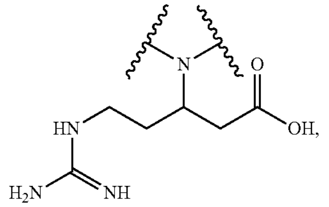
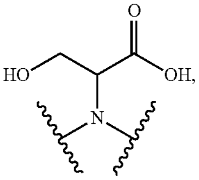
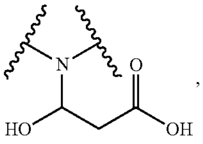
,
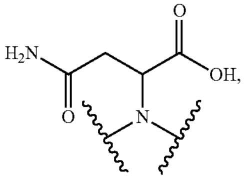
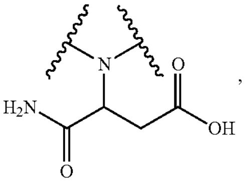
,
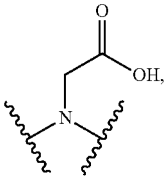
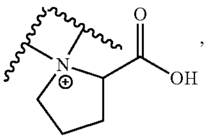
,
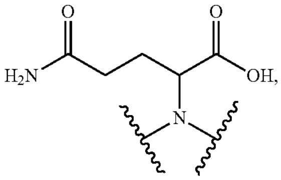
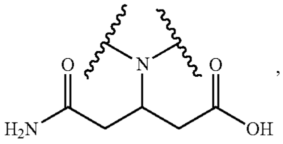
,
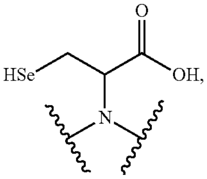
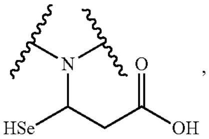
,
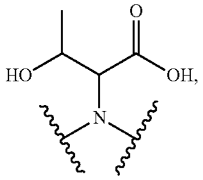
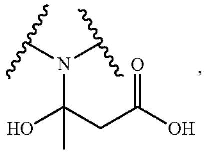
,
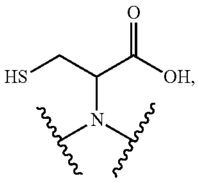
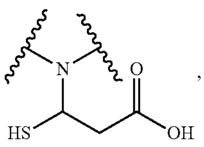
,
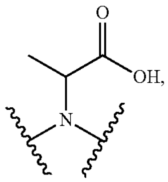
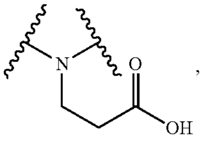
,
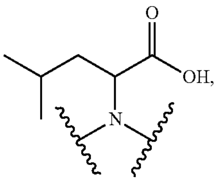
-continued
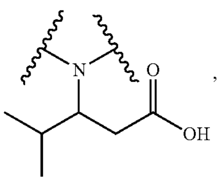
,
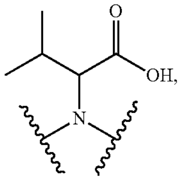
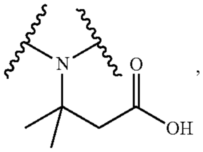
,
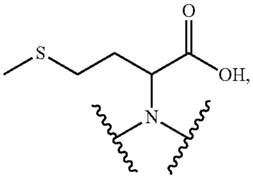
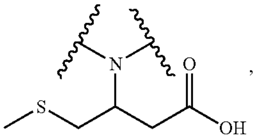
,
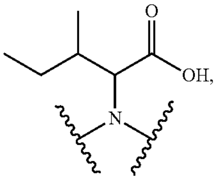
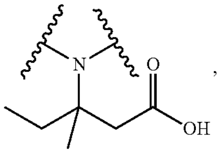
,
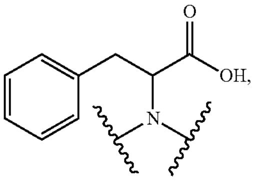
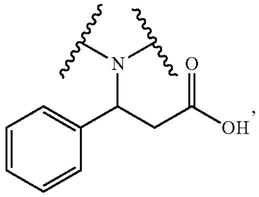
,
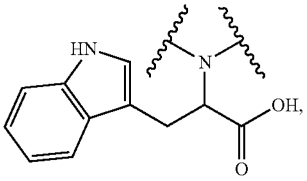
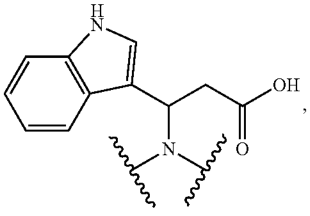
,
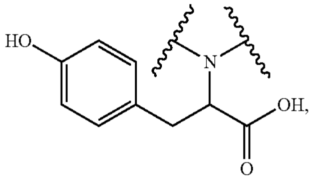
or
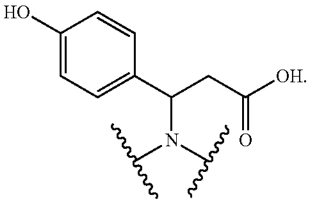

In embodiments, the compound is:

(Compound A)

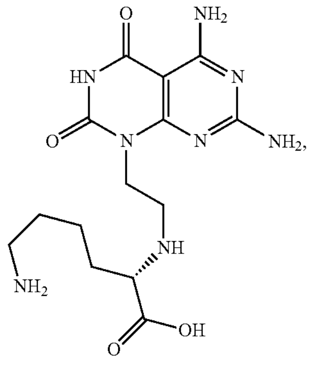

(Compound B)

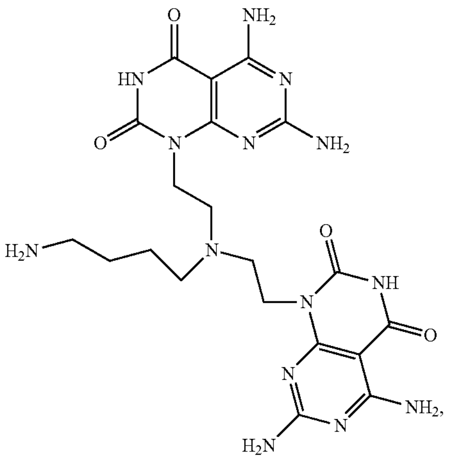

(Compound C)

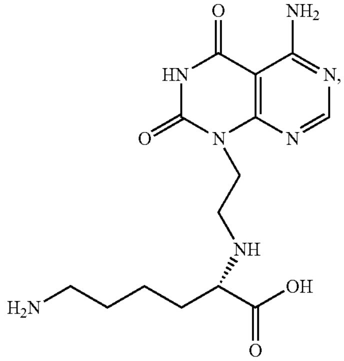

or

-continued (Compound D)

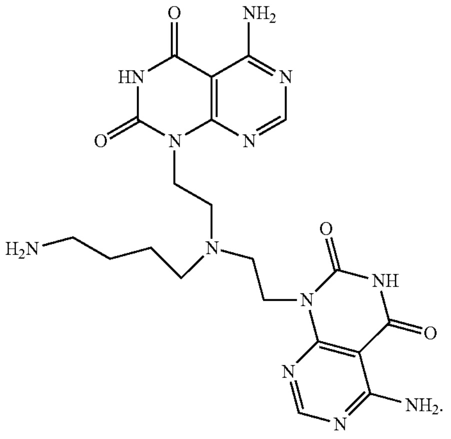

In embodiments, Compound A is positively charged at pH 6.0 and negatively charged at pH 11.5.

In embodiments, Compound B is positively charged at pH 7.4 and neutral at pH 12.

In embodiments, Compound C is positively charged at pH 6.0 and negatively charged at pH 11.5.

In embodiments, Compound D is positively charged at pH 7.4 and neutral at pH 12.

Synthesis

The following four structures are examples of total synthesis (Scheme A):

<u>Scheme A</u>

Compound A

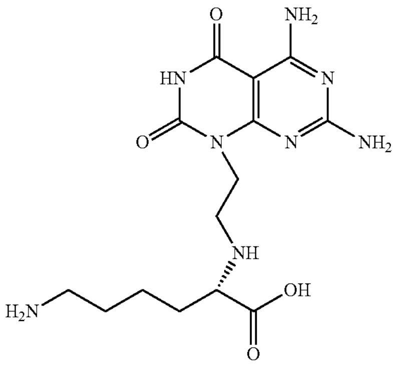

Compound B

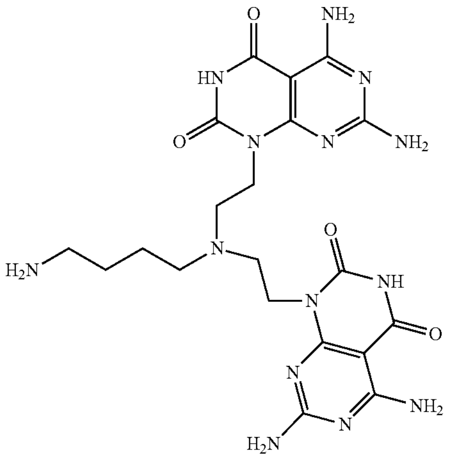

-continued

Compound C

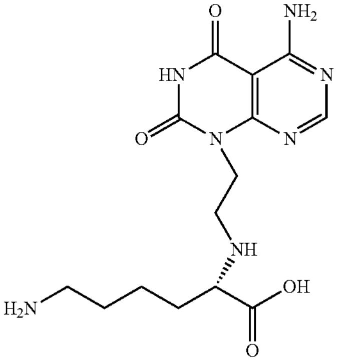

Compound D

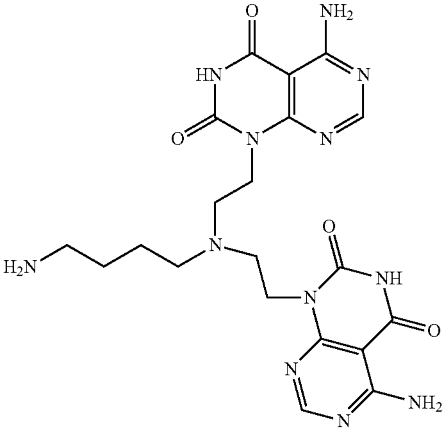

All reagents and solvents were obtained from commercial suppliers and used without further purification. Commercial suppliers include Sigma-Aldrich, Alfa Aesar, Oakwood chemical, Cambridge Isotopes and Fisher Scientific. NMR spectra are recorded on a Bruker high field NMR spectrometers with the solvents as internal reference. (400 MHz and 600 MHz) The following abbreviation are used for the proton spectra multiplicities: s, singlet; br s, broad singlet; d, doublet; dd double doublet; t, triplet; q, quartet; sep, septet; m, multiplet. Coupling constants (J) are reported in hertz (Hz). Compounds A5 and A were purified by semi-prep HPLC on an Agilent 1200 system with a Hypersil GOLD aQ column reverse phase column (150×10 mm L×W, particle size 5 um, Thermo Scientific), flow rate of 3 mL/min, and a linear gradient of a trinary solvent system of water/acetonitrile/pH=1 hydrochloric acid (A: diionized water, B: acetonitrile, C: pH=1 hydrochloric acid). TLC analysis was performed on silica gel F254 (Agela Technologies) and detection was carried out by UV light and with potassium permanganate staining. Flash column chromatography was performed on silica gel 60F with solvent of HPLC grade. All reactions are performed under nitrogen atmosphere and anhydrous condition unless specifically noted.

Abbreviations of reagents and compounds used in synthesis are as follows: Ac (acetyl); ACN (acetonitrile); Bn (benzyl); Boc (tert-Butyloxycarbonyl); Bz (benzoyl); Cbz (benzyloxycarbonyl); DCC (N,N'-Dicyclohexylcarbodiimide); 1,2-DCE (1,2-Dichloroethane); DCM (Dichloromethane); $dH_2O$ or DI $H_2O$ (deionized Water); DIPEA (N,N-Diisopropylethylamine); DMAP (4-Dimethylaminopyridine); DMF (N,N-Dimethylformamide); Et (ethyl); EtOH (Ethanol); EtsN or TEA (Triethylamine); Me (methyl); MeOH (Methanol); $NaBH(OAc)_3$ (Sodium triacetoxyborohydride); NMMO (N-Methylmorpholine N-oxide); Ph (phenyl); TEA (Triethylamine); TFA (Trifluoroacetic acid); TFAA (Trifluoroacetic anhydride); THF (Tetrahydrofuran). Abbreviations of reaction conditions and technique are as follows: h (hour); min (minute); r.t. (room temperature); TLC (thin layer chromatography).

Compound A and B are synthesized from the same starting materials, and synthetic schemes are shown below:

Scheme 1.

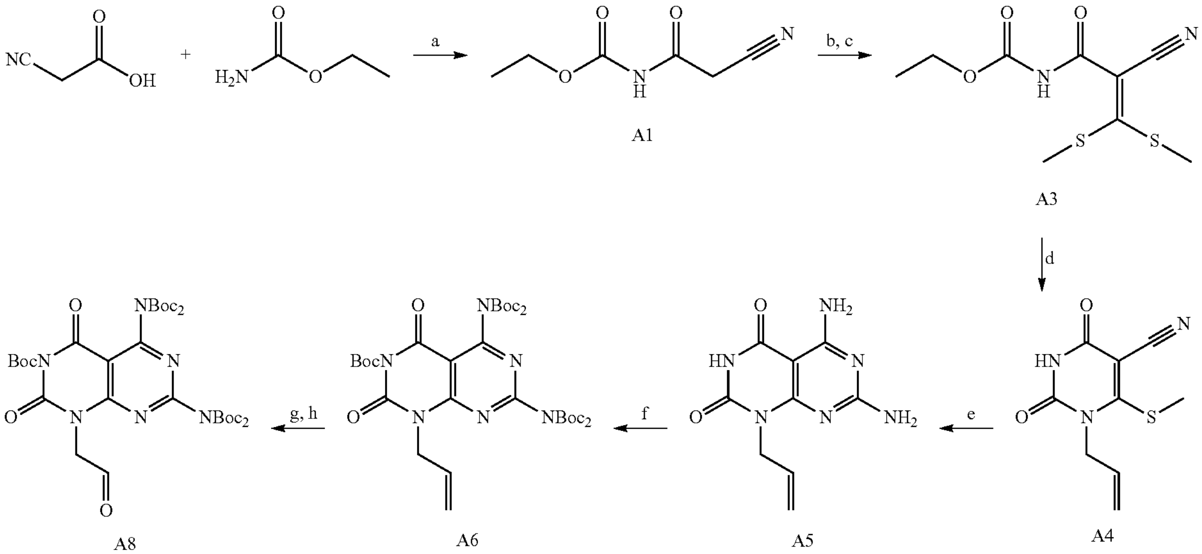

Scheme 1. (a) $POCl_3$, toluene, DMF, 70° C., 1.5 h, 89.2%. (b) $K_2CO_3$, $CS_2$, DMF, r.t., 6 h, 92.3%. (c) MeI, water, acetonitrile, 95° C., 3 h, 86.9%. (d) Allylamine, EtOH, reflux, 16 h, 66.8%. (e) Guanidinium hydrochloride, NaOEt, EtOH, reflux, 16 h, 93.3%. (f) DMAP, $Boc_2O$, TEA, THF, r.t., 40 h, 58.5%. (g) $OsO_4$, NMMO, water, acetone, r.t., 24 h, 79.7%. (h) $NaIO_4$, DCM, water, r.t., 42 h, 82.8%.

Scheme 2
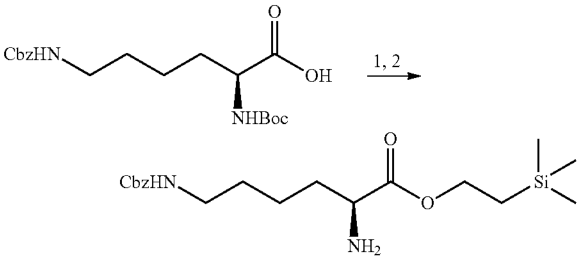
Compound 15
Scheme 2. (1) DMAP, 2-trimethylsilylethanol, DCC, DCM, r.t., 24 h, 98.2%. (2) TFA, DCM, r.t., 3 h, 90.8%.
Scheme 3.
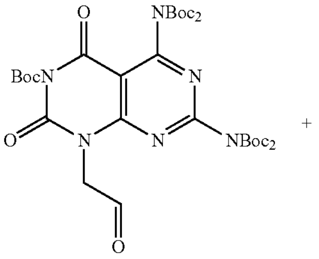
A8
-continued
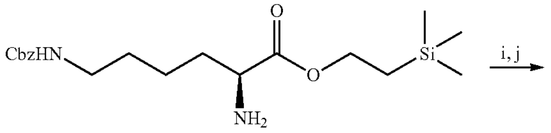
Compound 15
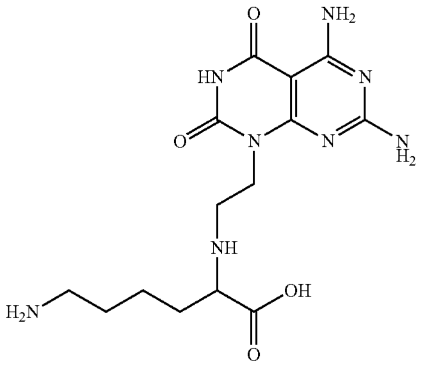
A
Scheme 3. (i) DIPEA, $NaBH(OAc)_3$, 1,2-DCE, r.t., 24 h, 71.2%. (j) TFA, thioanisole, r.t., 72 h, 93.8%.
Scheme 4.
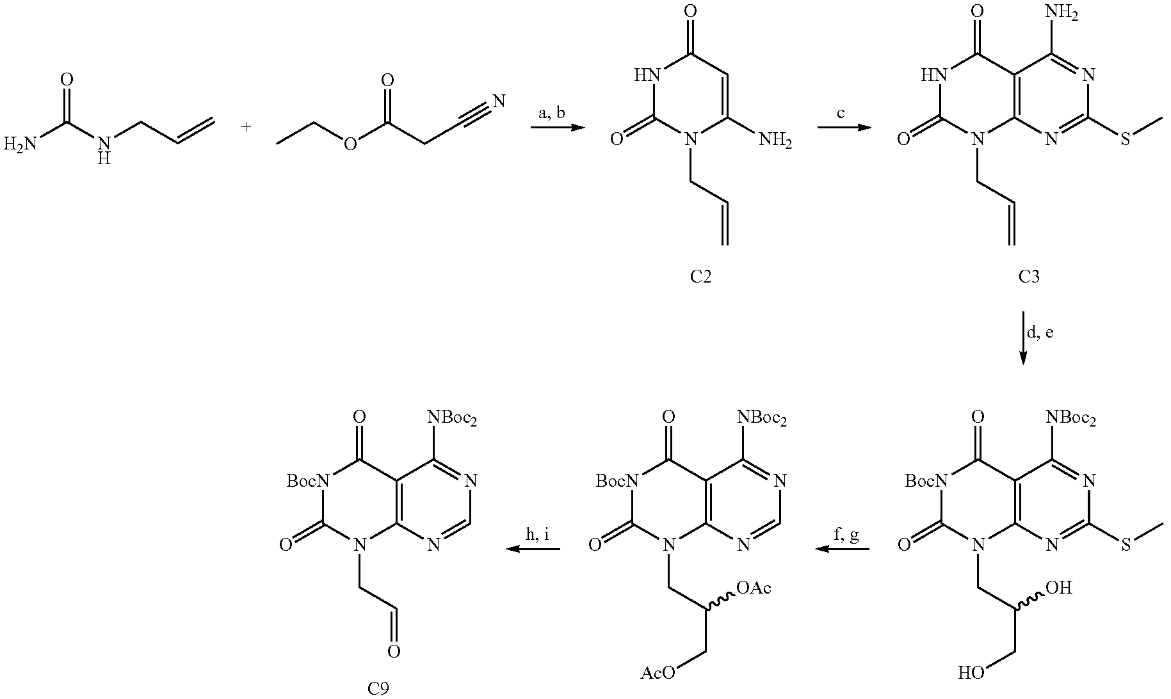
C2
C3
C5
C7
C9
Scheme 4. (k) $NaBH(OAc)_3$, 1,2-DCE, 16 h, r.t. (l) $NaBH(OAc)_3$, 1,2-DCE, 16 h, r.t. (k) TFA, thioanisole, r.t., 72 h.

Synthesis of Compounds A and B

Final compound A was prepared from commercially available starting materials with a synthetic pathway generating intermediates A1-A9 to afford the final compound A. Likewise, final compound B was prepared from synthesized intermediate compound A8 to produce further compound intermediates B9 and B10 to yield the final compound B.

Synthesis of Compound A

Synthesis of Compound A1

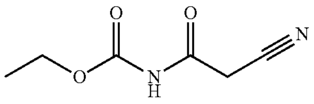

Commercially available 2-cyanoacetic acid (8.50 g) and ethylcarbamate (9.80 g) are dissolved in 25 mL toluene and 2.5 mL N',N'-dimethylformamide (DMF). After phosphoryl chloride (4.90 mL) is added drop wise, the solution is showing yellow color. Reaction mixture is then heated to 70° C., and kept for 1.5 hours. After reaction finished, the reaction mixture is cooled to room temperature and poured into 100 g ice water. Aqueous layer is then extracted with ethyl acetate (3×250 mL), and washed with brine (100 mL). After drying over anhydrous $Na_2SO_4$, filtration, pale yellow solid is generated after evaporating all volatiles. This yellow solid is then subjected to a silica gel flash column chromatography (3% MeOH/DCM) to result a white powder compound A1 (15.61 g, 89.2%). $R_f$=0.35 (5% $CH_3OH$/DCM). $^1$H-NMR (400 MHZ, DMSO-$d_6$) δ (ppm): 10.99 ($C_3NHC_4$, s, 1H), 4.12 ($C_2H$, q, J=4.72 Hz, 2H), 4.09 ($C_5H$, s, 2H), 1.21 ($C_1H$, t, J=4.72 Hz, 3H). $^{13}$C-NMR (600 MHZ, DMSO-$d_6$) δ (ppm): 164.18 ($C_4$), 151.61 ($C_3$), 115.25 ($C_6$), 61.49 ($C_2$), 27.74 ($C_5$), 14.08 ($C_1$). HRMS (ESI) m/z calculated for $C_6H_8N_2O_3$+$H^+$ 157.0613. found 157.0627. Formula is confirmed as $C_6H_8N_2O_3$.

Synthesis of Compound A2

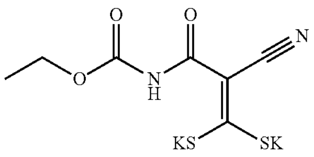

A solution of compound A1 (3.12 g) and potassium carbonate (2.75 g) in DMF (50 mL) is stirred at room temperature for 2 hours. 2.6 mL carbon disulfide is added to the reaction suspension, and then kept stirring for 4 hours. After completion of the reaction, 100% ethanol is added to reaction mixture at 0° C. Yellow precipitate is generated and filtered out. After washing with diethyl ether and drying under reduced pressure overnight, pale yellow solid, compound A2 is obtained in a yield of 92.3%. $^1$H-NMR (400 MHZ, DMSO-$d_6$) δ (ppm): 14.92 ($C_3NHC_4$, s, 1H), 3.99 ($C_2H$, q, J=4.72 Hz, 2H), 1.16 ($C_1H$, t, J=4.72 Hz, 3H), $^{13}$C-NMR (600 MHZ, DMSO-$d_6$) δ (ppm): 222.21 ($C_7$), 164.35 ($C_4$), 152.08 ($C_3$), 125.16 ($C_6$), 97.80 ($C_5$), 59.09 ($C_2$), 14.50 ($C_1$). HRMS (ESI) m/z calculated for $C_7H_6N_2O_3S_2K_2$+$H^+$ 308.9172. found 308.9171. Formula is confirmed as $C_7H_8N_2O_3S_2K_2$.

Synthesis of Compound A3

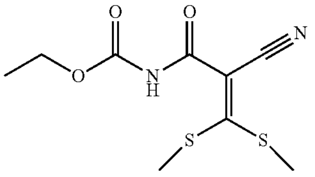 [SMILES: CCOC(=O)NC(=O)C(C#N)=C(SC)SC]

To a solution of compound A2 (6.18 g) in 80 mL water/acetonitrile (7:3), methyl iodide (2.7 mL in 15 mL acetonitrile) is added drop wise. After stirring at room temperature for 30 min, the reaction flask is heated to 95° C., and kept for 3 hours. Reaction mixture is cooled to room temperature, and volatiles are removed under reduce pressure. Then the residue is extracted with ethyl acetate (3×100 mL). Organic layers are combined and washed with brine. After drying over anhydrous sodium sulfate and evaporation, yellow crude solid is obtained and after subjected to a silica gel flash column chromatography (30% ethyl acetate/hexanes) to result a light yellow solid compound A3 (4.52 g) is obtained in a yield of 86.9%. $R_f$=0.20 (30% ethyl acetate/hexanes). $^1$H-NMR (400 MHZ, $CDCl_3$) δ (ppm): 7.98 ($C_3NHC_4$, br, s, 1H), 4.27 ($C_2H$, q, J=7.16 Hz, 2H), 2.76 ($C_8H$ or $C_9H$, s, 3H), 2.60 ($C_8H$ or $C_9H$, s, 3H), 1.32 ($C_1H$, t, J=7.16 Hz, 3H). $^{13}$C-NMR (600 MHz, $CDCl_3$) δ (ppm): 182.91 ($C_7$), 159.19 ($C_4$), 150.54 ($C_3$), 116.89 ($C_6$), 98.82 ($C_5$), 62.80 ($C_2$), 21.12 ($C_8$ or $C_9$), 19.56 ($C_8$ or $C_9$), 14.40 ($C_1$). HRMS (ESI) m/z calculated for $C_9H_{12}N_2O_3S_2$+$H^+$ 261.0368, found 261.0361. Formula is confirmed as $C_9H_{12}N_2O_3S_2$.

Synthesis of Compound A4

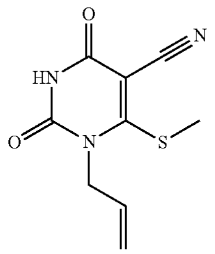

To a solution of compound A3 (3.14 g) in absolute ethanol (75 mL), allylamine (925 uL in 20 mL ethanol) is added drop wise over 30 min. Then reaction mixture is heated to reflux for 16 hours. After cooling to room temperature and evaporation of volatiles, a yellow solid residue is obtained. A flash column chromatography (50% ethyl acetate/hexanes to 2% MeOH/DCM) is applied to yield a white crystal compound A4 (1.80 g, 66.8%). $R_f$=0.68 (10% MeOH/DCM). $^1$H-NMR (400 MHz, DMSO-$d_6$) δ (ppm): 12.13 ($C_3NHC_4$, s, 1H), 5.88 ($C_8H$, m, 1H) 5.17 ($C_9H$, ddd, $J_1$=17.44 Hz, $J_2$=7.08 Hz, $J_3$=0.64 Hz, 2H), 4.69 ($C_7H$, d, J=3.76 Hz, 2H), 2.76 ($C_6H$, s, 3H). $^{13}$C-NMR (600 MHz, DMSO-de) δ (ppm): 166.49 ($C_4$), 159.36 ($C_2$), 148.99 ($C_1$), 132.28 ($C_5$), 116.76 ($C_9$), 114.50 ($C_5$), 92.58 ($C_3$), 48.15 ($C_7$), 19.30 ($C_6$). HRMS (ESI) m/z calculated for $C_9H_9N_2O_3S$+$H^+$ 224.0494. found 224.0489. Formula is confirmed as $C_9H_9N_2O_3S$.

Synthesis of Compound A5

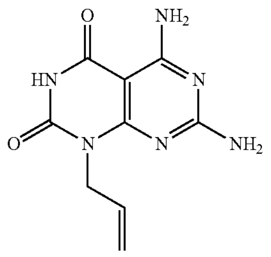 [SMILES: C=CCn1c(=O)[nH]c(=O)c2c(N)nc(N)nc21]

A mixture of guanidinium hydrochloride (2.05 g) and sodium ethoxide (21% wt., 7.8 mL) in absolute ethanol (14 mL) is heated to 45° C. for 15 min. After filtration, filtrate is added directly into 40 mL absolute ethanol, containing compound A4 (2.70 g). Reaction mixture is then heated to reflux and kept for 16 hours. Off white solid (compound A5, 2.65 g) is precipitated out in a yield of 93.3%. Small portion of product is purified through reverse phase HPLC, and used for NMR and Massspectrum. $^1$H-NMR (400 MHZ, DMSO-$d_6$) δ (ppm): 11.13 ($C_1NHC_2$, br, s, 1H), 8.04 (CNH, br, s, 1H), 7.45 ($C_6NH$, br, s, 1H) 6.91 ($C_5NH$, br, s, 2H), 5.85 ($C_8H$, m, 1H), 5.08 ($C_8H$, dt, $J_1$=5.72 Hz, $J_2$=1.52 Hz, 2H), 4.57 ($C_7H$, d, J=5.0 Hz, 2H). $^{13}$C-NMR (600 MHz, DMSO-$d_6$) δ (ppm): 163.75 ($C_4$), 163.64 ($C_6$), 163.47 ($C_5$) 159.27 ($C_2$), 151.26 ($C_1$), 134.26 ($C_8$), 115.12 ($C_9$), 82.99 ($C_3$), 42.23 ($C_7$). HRMS (ESI) m/z calculated for $C_9H_{10}N_6O_2$+$H^+$ 235.0943. found 235.0937. Formula is confirmed as $C_9H_{10}N_6O_2$.

HPLC isolation of compound A5 is performed on a semi-prep Hypersil GOLD aQ column (150×10 mm L×W, particle size 5 um), the isolation program is listed below:

Solvent A: 100% DI water; Solvent B: 100% acetonitrile.

| Time | A % | B % |
|---|---|---|
| 0.00 min | 100.0 | 0 |
| 4.00 min | 60.0 | 40.0 |
| 12.00 min | 30.0 | 70.0 |
| 14.00 min | 0 | 100.0 |

Synthesis of Compound A6

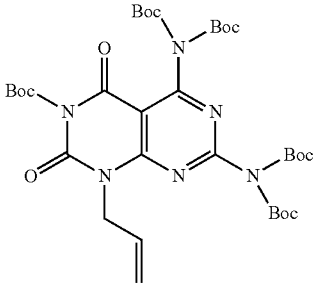 [SMILES: C=CCn1c(=O)n(C(=O)OC(C)(C)C)c(=O)c2c(N(C(=O)OC(C)(C)C)C(=O)OC(C)(C)C)nc(N(C(=O)OC(C)(C)C)C(=O)OC(C)(C)C)nc21]

To slurry mixture of compound A5 (2.11 g) and DMAP (1.10 g) in THF (120 mL), triethylamine (24.9 mL) is added slowly over 1 min. After stirring at room temperature for 2 min, 20.7 mL Di-tert-butyl dicarbonate ($Boc_2O$) is added drop wise to the reaction mixture. And then the mixture is stirred at room temperature for 40 hours, and the reaction mixture turn into reddish solution. Upon thin layer chromatography (TLC) applied to identify the completion of reaction, 20 mL $dH_2O$ is added to quench the reaction. And then volatiles are removed under reduce pressure, the red viscous residue is taken up by 500 mL ethyl acetate, and then washed with water (250 mL), 10% citric acid (75 mL), water (2×200 mL), Sodium bicarbonate solution (200 mL), and brine (250 mL). After drying over anhydrous sodium sulfate and filtration, solvent of filtrate is removed under vacuum, resulting in a red/orange solid. This solid is purified by flash chromatography (0-20% ethyl acetate in hexanes over silica gel) to yield white foam compound A6 (3.87 g) in a yield of 58.5%. $R_f$=0.65 (30% ethyl acetate/hexanes). $^1$H-NMR (400 MHz, $CDCl_3$) δ (ppm): 5.94 ($C_8H$, m, 1H), 5.31 ($C_9H$, dd, $J_1$=37.84 Hz, $J_2$=10.2 Hz, 2H), 4.81 ($C_7H$, d, J=5.6 Hz, 2H), 1.59 ($C_{12}H$, s, 9H), 1.50 ($C_{15,\ 18\ or\ 21,\ 24}H$, s, 18H), 1.45 ($C_{15,\ 18\ or\ 21,\ 24}H$, s, 18H), $^{13}$C-NMR (600 MHz, $CDCl_3$) δ (ppm): 162.60 ($C_4$), 159.80 ($C_{19,\ 22}$), 159.37 ($C_2$), 155.81 ($C_{13,\ 16}$), 149.80 ($C_6$), 149.72 ($C_5$), 147.89 ($C_{10}$), 146.94 ($C_1$), 130.68 ($C_5$), 119.97 ($C_9$), 87.71 ($C_{11}$), 84.66 ($C_{20,\ 23}$), 84.53 ($C_{14,\ 17}$), 82.48 ($C_3$), 45.31 ($C_7$), 27.95 ($C_{21,\ 24}$), 27.91 ($C_{15,\ 18}$), 27.61 ($C_{12}$). HRMS (ESI) m/z calculated for $C_{34}H_{50}N_6O_{12}$+$H^+$ 735.3565. found 735.3553. Formula is confirmed as $C_{34}H_{50}N_6O_{12}$.

Synthesis of Compound A7

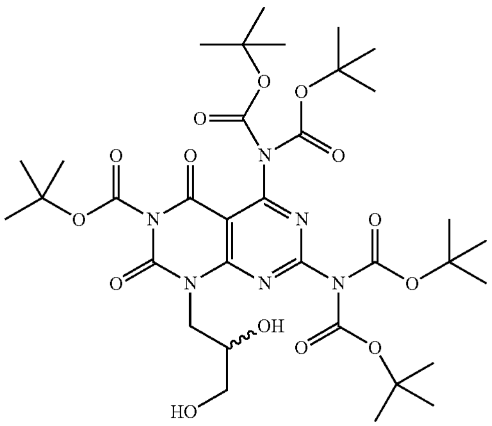 [SMILES: CC(C)(C)OC(=O)N(C(=O)OC(C)(C)C)c1nc(N(C(=O)OC(C)(C)C)C(=O)OC(C)(C)C)c2c(=O)n(C(=O)OC(C)(C)C)c(=O)n(CC(O)CO)c2n1]

Compound A6 (2.93 g) is dissolved in acetone/water (8:1, 58.5 mL). And then NMMO (50% by weight in water, 1.64 mL) is added drop wise to the reaction mixture. After stirring at room temperature for 5 min, $OsO_4$ (4% aqueous solution) is added drop wise over a period of 3 min, resulting in a light yellow solution. The resulting solution is stirring at room temperature for 24 hours, then quenched with aqueous sodium sulfite (1.0M) until solution turn to colorless. Then volatiles are removed under vacuum, resulting in white slurry in water. The product is extracted by 350 mL dichloromethane (DCM) from the residue, and then washed with water (150 mL) and brine (150 mL). The organic layer is then dried over anhydrous $Na_2SO_4$, filtered, and evaporated to dryness under vacuum to yield white solid compound A7 (2.45 g, 79.7%) as inseparable diastereomers mixture. Compound A7 is directly used for the next step without further purification. $R_f$ (inseparable diastereomers mixture)=0.25 (30% ethyl acetate/hexanes). HRMS (ESI) m/z calculated for $C_{34}H_{52}N_6O_{14}$+$H^+$ 769.3620. found 769.3617. Formula is confirmed as $C_{34}H_{52}N_6O_{12}$.

Synthesis of Compound A8

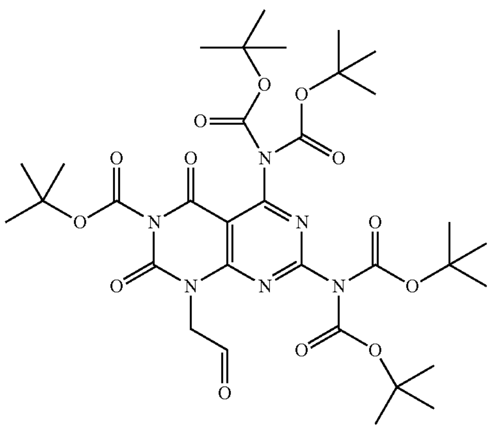 [SMILES: CC(C)(C)OC(=O)N(C(=O)OC(C)(C)C)c1nc(N(C(=O)OC(C)(C)C)C(=O)OC(C)(C)C)c2c(=O)n(C(=O)OC(C)(C)C)c(=O)n(CC=O)c2n1]

Compound A7 (1.36 g) is dissolved in dichloromethane (DCM)/water mixture (6:1, 35 mL), and then sodium periodide (760 mg) and stirred for 42 hour. After TLC monitoring indicating the full consumption of starting materials, the insoluble material is filtered off, and filtrate is then separated and concentrated under reduced pressure. And resulting residue is extracted by 250 mL DCM, and then washed with 100 mL water and 100 mL brine. And then the crude product is purified through silica gel flash chromatography (5-40% ethyl acetate in hexanes, then 5% methanol in DCM) to yield compound A8 (1.08 g, 82.8%). $^{1}$H-NMR (400 MHZ, $CDCl_3$) δ (ppm): 9.64 ($C_8$H, s, 1H), 5.04 ($C_7$H, s, 2H), 1.57 ($C_{11}$H, s, 9H), 1.46 ($C_{20,\ 23}$H, s, 18H), 1.45 ($C_{14,\ 17}$H, s, 18H). $^{13}$C-NMR (600 MHz, $CDCL_3$) δ (ppm): 192.85 ($C_5$), 162.58 ($C_4$), 159.50 ($C_{18,\ 21}$), 158.99 ($C_2$), 155.81 ($C_{12,\ 15}$), 149.45 ($C_6$), 149.31 ($C_5$), 147.79 ($C_{10}$), 146.45 ($C_1$), 87.90 ($C_{10}$), 84.77 ($C_{19,\ 22}$), 84.58 ($C_{13,\ 16}$), 82.66 ($C_3$), 51.45 ($C_7$), 27.82 ($C_{20,\ 23}$), 27.76 ($C_{14,\ 17}$), 27.39 ($C_{11}$). $R_f$=0.60 (40% ethyl acetate/hexanes). HRMS (ESI) m/z calculated for $C_{33}H_{48}N_6O_{13}$+$H^+$ 737.3258. found 737.3357. Formula is confirmed as $C_{33}H_{48}N_6O_{13}$.

Synthesis of Compound 14

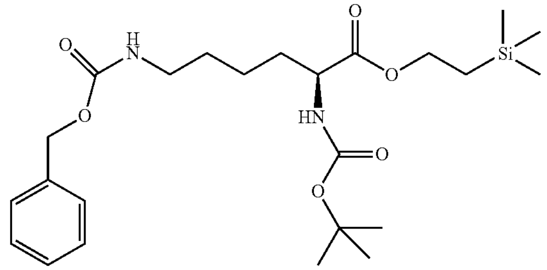 [SMILES: CC(C)(C)OC(=O)N[C@@H](CCCCNC(=O)OCc1ccccc1)C(=O)OCC[Si](C)(C)C]

6-benzyloxycarbonylamino-2-tert-butoxycarbonyl-L-amino-hexanoic acid (1.9 g), DMAP (62 mg), and 2-trimethylsilylethanol (720 μL) are dissolved in 25 mL DCM, and then the mixture is cool to 0° C. After stirring at 0° C. for 5 min, reaction mixture is added DCC (1.40 g) at 0° C., and the resulting slurry is kept at 0° C. and stirring for 15 min. Then reaction mixture is warmed to room temperature and kept stirring for 24 hours. The solution is filtered to remove formed N,N'-Dicyclohexylurea from reaction. The filtrate is then concentrated under reduced pressure, to generate an off-white viscous oil as crude product. The crude product is subjected to silica gel flash chromatography (5-20% ethyl acetate in hexanes) to yield a colorless viscous liquid compound 14 (2.36, 98.2%). $R_f$=0.63 (30% ethyl acetate/hexanes). $^{1}$H-NMR (400 MHZ, $CDCl_3$) δ (ppm): 7.30-7.38 ($C_{16\text{-}20}$H, m, 5H), 5.09 ($C_{14}$H, s, 2H), 4.81 ($C_8$H, br, s, 1H), 4.23 ($C_5$H, t, J=8.64 Hz, 2H), 3.19 ($C_{12}$H, q, J=6.38 Hz, 2H) 1.79 ($C_9$H, br, m, 2H), 1.48-1.62 ($C_{10}$, 11H, br, m, 3H), 1.43 ($C_4$H, s, 9H), 1.35 ($C_{10}$H, br, m, 1H), 1.00 ($C_6$H, t, J=8.68 Hz, 2H), 0.04 ($C_7$H, s, 9H). $^{13}$C-NMR (600 MHz, $CDCl_3$) δ (ppm): 173.07 ($C_1$), 156.65 ($C_{13}$), 155.69 ($C_2$), 136.80 ($C_{15}$), 128.72, 128.34, 128.30 ($C_{16\text{-}20}$), 80.05 ($C_3$), 66.84 ($C_{14}$), 63.95 ($C_5$), 53.47 ($C_8$), 40.90 ($C_{12}$), 33.71 ($C_9$), 29.56 ($C_{10}$), 28.53 ($C_4$), 22.60 ($C_{11}$), 17.59 ($C_6$), −1.31 ($C_7$). HRMS (ESI) m/z calculated for $C_{24}H_{40}N_2O_6Si$+$H^+$ 481.2734. found 481.2728. Formula is confirmed as $C_{24}H_{40}N_2O_6Si$.

Synthesis of Compound 15

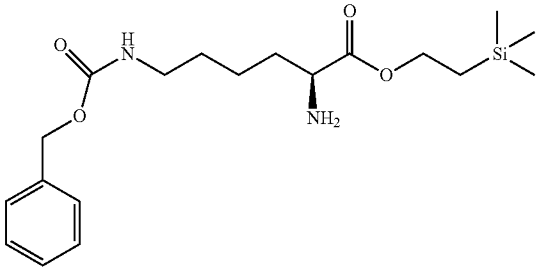 [SMILES: C[Si](C)(C)CCOC(=O)[C@@H](N)CCCCNC(=O)OCc1ccccc1]

To a solution of compound 14 (2.40 g) in DCM (80 mL), TFA (8 mL) is added to the reaction flask. Then the reaction is kept stirring at room temperature for 3 hours. After reaction, DCM and the excess TFA is removed under reduced pressure. The viscous liquid residue is then applied to silica gel flash chromatography (0-10% methanol in DCM) to yield a colorless viscous liquid compound 15 (1.73, 90.8%). $R_f$=0.65 (10% methanol/DCM). $^{1}$H-NMR (400 MHz, DMSO-$d_6$) δ (ppm): 8.29 ($C_5$NH, br, 1H) 7.25-7.38 ($C_{13\text{-}17}$H, m, 5H), 5.00 ($C_{11}$H, s, 2H), 4.25 ($C_2$H, t, J=8.00 Hz, 2H), 3.98 ($C_5$H, br, s, 1H), 2.98 ($C_9$H, d, J=5.84 Hz, 2H) 1.74 ($C_6$H, br, m, 2H), 1.22-1.46 ($C_{7,\ 8}$H, br, m, 4H), 1.00 ($C_1$H, t, J=7.84 Hz, 2H), 0.04 ($C_4$H, s, 9H). $^{13}$C-NMR (600 MHz, $CDCl_3$) δ (ppm): 169.72 ($C_1$), 156.09 ($C_{10}$), 137.20 ($C_{11}$), 128.35, 127.77, 127.70 ($C_{13\text{-}17}$), 65.13 ($C_{11}$), 64.01 ($C_2$), 51.91 ($C_5$), 40.04 ($C_9$), 29.74 ($C_6$), 28.80 ($C_8$), 21.48 ($C_7$), 16.85 ($C_3$), −1.56 ($C_4$). HRMS (ESI) m/z calculated for $C_{19}H_{32}N_2O_4Si$+$H^+$ 381.2210. found 381.2204. Formula is confirmed as $C_{19}H_{32}N_2O_4Si$.

Synthesis of Compound A9

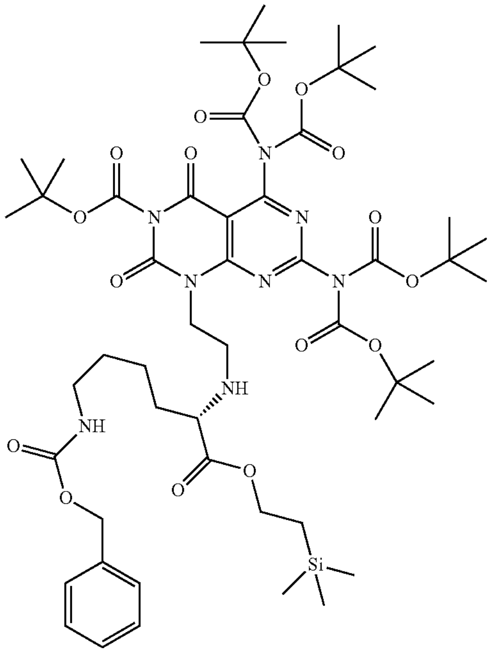 [SMILES: CC(C)(C)OC(=O)N(C(=O)OC(C)(C)C)c1nc(N(C(=O)OC(C)(C)C)C(=O)OC(C)(C)C)c2c(=O)n(C(=O)OC(C)(C)C)c(=O)n(CCN[C@@H](CCCCNC(=O)OCc3ccccc3)C(=O)OCC[Si](C)(C)C)c2n1]

6-benzyloxycarbonylamino-2-L-amino-hexanoic acid trimethylsilyl ethyl ester (649.5 mg) and N,N-Diisopropylethylamine (DIPEA, 591 μL) are dissolved in 1,2-dichloroethane (1,2-DCE, 24 mL). A solution of compound A8 (830 mg) in 1,2-DCE (15 mL) is added to reaction mixture drop wise over 3 min. After stirring at room temperature for 15 min, solid $NaBH(OAc)_3$ (360.3 mg) is added to the solution. The resulting slurry is then stirred at room temperature for 24 hours. After TLC monitoring indicating fully consumption of starting materials, reaction mixture is quenched with water (6 mL). Then the reaction mixture is extracted with dichloromethane (3×200 mL), organic layers are combined and washed with 10% citric acid in water (200 mL), water (2×200 mL), saturated sodium bicarbonate (200 mL), and brine (200 mL). After drying over $NaSO_4$, filtration and evaporation of solvent under reduced pressure are performed, and residue is then applied to a silica gel flash chromatography (5-30% ethyl acetate in hexanes) to yield compound A9 (885 mg, 71.2%). $R_f$=0.40 (30% ethyl acetate/hexanes). $^1$H-NMR (400 MHZ, DMSO-$d_6$) δ (ppm): 10.67 ($C_{17}NHC_{18}$, br, s, 1H) 7.28-7.34 ($C_{21-25}$H, m, 5H), 5.06 ($C_{19}$H, s, 2H), 4.29 ($C_9$H, br, 1H), 4.17 ($C_1$H, m, 1H), 3.17 ($C_8$H, m, 2H), 2.74 ($C_{17}$H, m, 2H) 1.74 ($C_{14}$H, br, m, 2H), 1.57 ($C_{28}$H, s, 9H), 1.46 ($C_{37,\ 40}$H, s, 18H), 1.45 ($C_{31,\ 34}$H, s, 18H), 1.22-1.41 ($C_{15,\ 16}$H, br, m, 4H), 0.98 ($C_3$H, m, 2H), 0.04 ($C_{13}$H, s, 9H). HRMS (ESI) m/z calculated for $C_{52}H_{80}N_8O_{16}Si+H^+$ 1101.5540. found 1101.5521. Formula is confirmed as $C_{52}H_{80}N_8O_{16}Si$.

Synthesis of Compound A

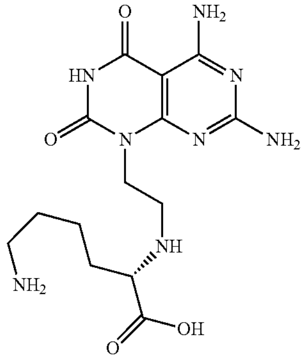 [SMILES: NCCCC[C@H](NCCn1c(=O)[nH]c(=O)c2c(N)nc(N)nc21)C(=O)O]

Compound A9 (0.54 g) is added into 94% TFA/thioanisole solution (10 mL). After stirring at room temperature for 72 hours, diethyl ether ($Et_2O$, 80 mL) is added. White precipitate of product compound A forms, the precipitate is then centrifuged down. After pouring clear TFA containing supernatant out, white precipitate is then washed with $Et_2O$, methanol to yield crude product (168.6 mg, 93.8%). The crude product is purified by HPLC to get pure product of white solid compound A. $^1$H-NMR (400 MHZ, DMSO-$d_6$) δ (ppm): 11.43 ($C_1NHC_2$, br, s, 1H) 9.23 ($C_6$NH, br, 1H), 9.02 ($C_6$NH, br. 1H), 8.33 ($C_9HC_8$, br, 1H), 7.99 ($C_{14}$NH, br, 3H, $C_{14}$NH has been protonated by $C_{10}$OH) 7.45 ($C_5$NH, br, 2H), 4.18-4.36 ($C_7$H, m, 2H), 4.08 ($C_9$H, br, 1H), 3.31 ($C_8$H, br, 2H), 2.75 ($C_{14}$H, q, J=6.44 Hz, 2H) 1.91 ($C_{11}$H, br, m, 1H), 1.77 ($C_{11}$H, br, m, 1H), 1.58 ($C_{13}$H, br, m, 2H), 1.46 ($C_{12}$H, br, m, 1H), 1.31 ($C_{12}$H, br, m, 1H). $^{13}$C-NMR (600 MHz, $D_2O$ with drops of DMSO-$d_6$ as reference) δ (ppm): 173.48 ($C_{10}$), 163.90 ($C_4$), 161.88 ($C_2$), 157.97 ($C_6$), 157.02 ($C_5$), 153.09 ($C_1$), 85.31 ($C_3$), 62.39 ($C_9$), 46.21 ($C_7$), 40.59 ($C_8$), 40.03 ($C_{14}$), 29.99 ($C_{11}$), 27.96 ($C_{13}$), 23.02 ($C_{12}$). HRMS (ESI) m/z calculated for $C_{14}H_{22}N_8O_4+H^+$ 367.1842. found 367.1832. Formula is confirmed as $C_{14}H_{22}N_8O_4$.

HPLC isolation of compound A is performed on a semi-prep Hypersil GOLD aQ column (150×10 mm L×W, particle size Sum), the isolation program is listed below:

Solvent A: 100% DI water; Solvent B: 100% acetonitrile; Solvent C: pH=1 HCl water solution

| Time | A % | B % | C % |
|---|---|---|---|
| 0.00 min | 98.0 | 0 | 2.0 |
| 15.00 min | 68.0 | 30.0 | 2.0 |
| 25.00 min | 8.0 | 90.0 | 2.0 |
| 26.00 min | 0 | 100.0 | 0 |

Compound A is shown the largest peak at HPLC, and collected at about 7.2 min.

Synthesis of Compound B

Synthesis of Compound B9

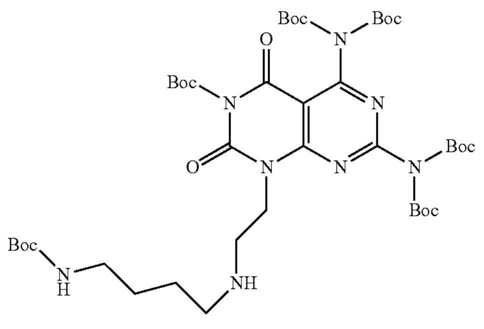 [SMILES: CC(C)(C)OC(=O)NCCCCNCCn1c(=O)n(C(=O)OC(C)(C)C)c(=O)c2c(N(C(=O)OC(C)(C)C)C(=O)OC(C)(C)C)nc(N(C(=O)OC(C)(C)C)C(=O)OC(C)(C)C)nc21]

Commercially available N-Boc-1,4-diaminobutane is added to a solution of Compound A8 in 1,2-DCE at room temperature. Then the mixture is stirred for 1 hour, solid $NaBH(OAc)_3$ is added. The resulting solution is then stirred at room temperature for 15 hours. Aqueous layer is extracted with DCM, and organic layers are combined and washed with water, and brine. After drying over $NaSO_4$, filtration and evaporation of solvent under reduced pressure are performed, and residue is then applied to a silica gel flash chromatography (0-10% methanol in DCM) to yield white foam compound B9.

Synthesis of Compound B10

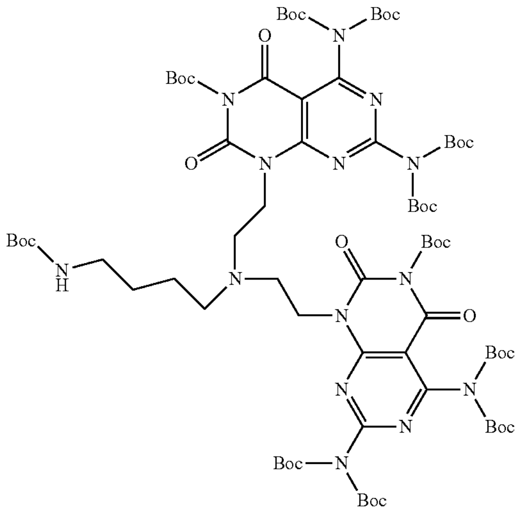 [SMILES: CC(C)(C)OC(=O)NCCCCN(CCn1c(=O)n(C(=O)OC(C)(C)C)c(=O)c2c(N(C(=O)OC(C)(C)C)C(=O)OC(C)(C)C)nc(N(C(=O)OC(C)(C)C)C(=O)OC(C)(C)C)nc21)CCn1c(=O)n(C(=O)OC(C)(C)C)c(=O)c2c(N(C(=O)OC(C)(C)C)C(=O)OC(C)(C)C)nc(N(C(=O)OC(C)(C)C)C(=O)OC(C)(C)C)nc21]

Compound A8 and compound B9 are dissolved in 1,2-DCE at room temperature, and stirred for 1 hour. Solid $NaBH(OAc)_3$ is added. The resulting solution is then stirred at room temperature for 15 hours. Aqueous layer is extracted with DCM, and organic layers are combined and washed with water, and brine. After drying over $NaSO_4$, filtration and evaporation of solvent under reduced pressure are performed, and residue is then applied to a silica gel flash chromatography (0-10% methanol in DCM) to yield white foam compound B10.

Synthesis of Compound B

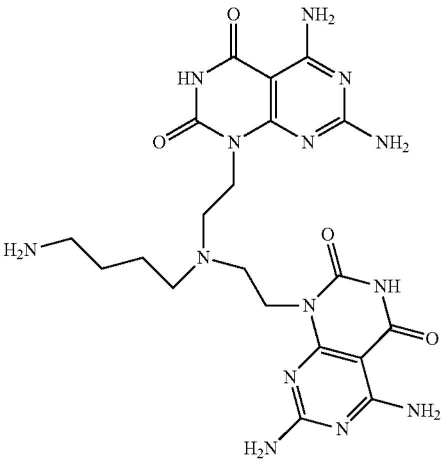 [SMILES: NCCCCN(CCn1c(=O)[nH]c(=O)c2c(N)nc(N)nc21)CCn1c(=O)[nH]c(=O)c2c(N)nc(N)nc21]

Compound B10 is added into 94% TFA/thioanisole solution. After stirring at room temperature for 72 hours, diethyl ether ($Et_2O$) is added. White precipitate of product compound B forms, and is then centrifuged and washed with $Et_2O$, MeOH. The crude product is obtained as white solid, and purified by HPLC to get pure product of white solid compound B. HPLC isolation of compound B is performed on a semi-prep Hypersil GOLD aQ column (150× 10 mm L×W, particle size 5 um), the isolation program is listed below: Solvent A: 100% DI water; Solvent B: 100% acetonitrile; Solvent C: pH=1 HCl water solution

| Time | A % | B % | C % |
|---|---|---|---|
| 0.00 min | 98.0 | 0 | 2.0 |
| 15.00 min | 68.0 | 30.0 | 2.0 |
| 25.00 min | 8.0 | 90.0 | 2.0 |
| 26.00 min | 0 | 100.0 | 0 |

Synthesis of Compounds C and D

Compound C and D are synthesized from the same starting materials, and synthetic schemes are shown below:

Scheme 5.
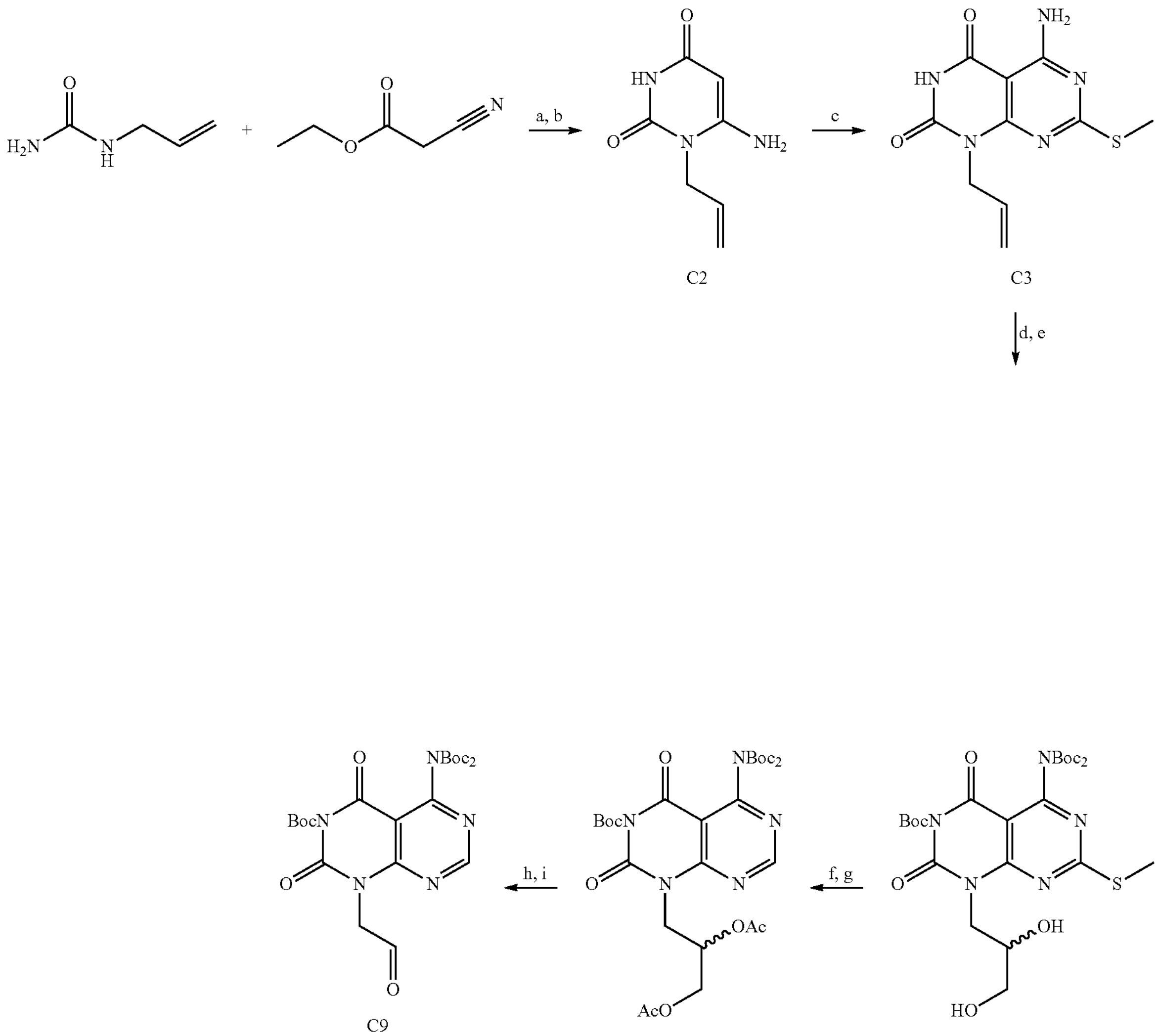
C2 C3
C9 C7 C5
Scheme 5. (a) $Ac_2O$, 85° C., 3 h, 59.1%. (b) NaOH, 85° C., 2 h, 62.2%. (c) $K_2CO_3$, dimethyl cyanodithioiminocarbonate, DMF, 100° C., 5 h, 92.8%. (d) DMAP, $Boc_2O$, TEA, THF, r.t., 40 h. (e) $OsO_4$, NMMO, water, acetone, r.t., 22 h. (f) $Ac_2O$, TEA, THF, r.t., 12 h. (g) Raney Ni, EtOH, reflux, 24 h. (h) 7N ammonia, MeOH, r.t., 10 h. (i) $NaIO_4$, DCM, water, r.t., 36 h.
Scheme 6.
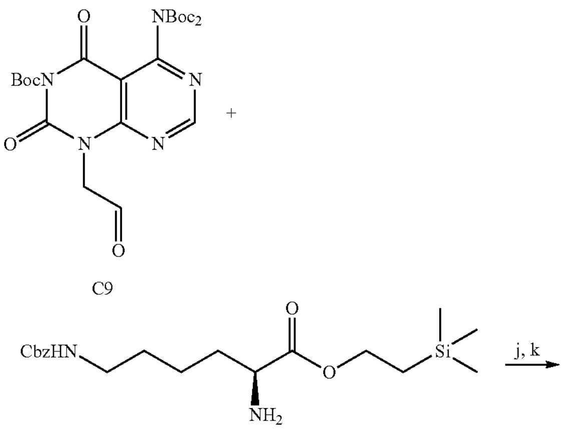
C9
-continued
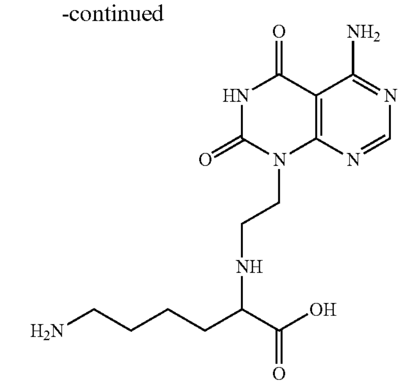
C
Scheme 2. (j) DIPEA, $NaBH(OAc)_3$, 1,2-DCE, r.t., 16 h. (j) TFA, thioanisole, r.t., 72 h.

Scheme 7.

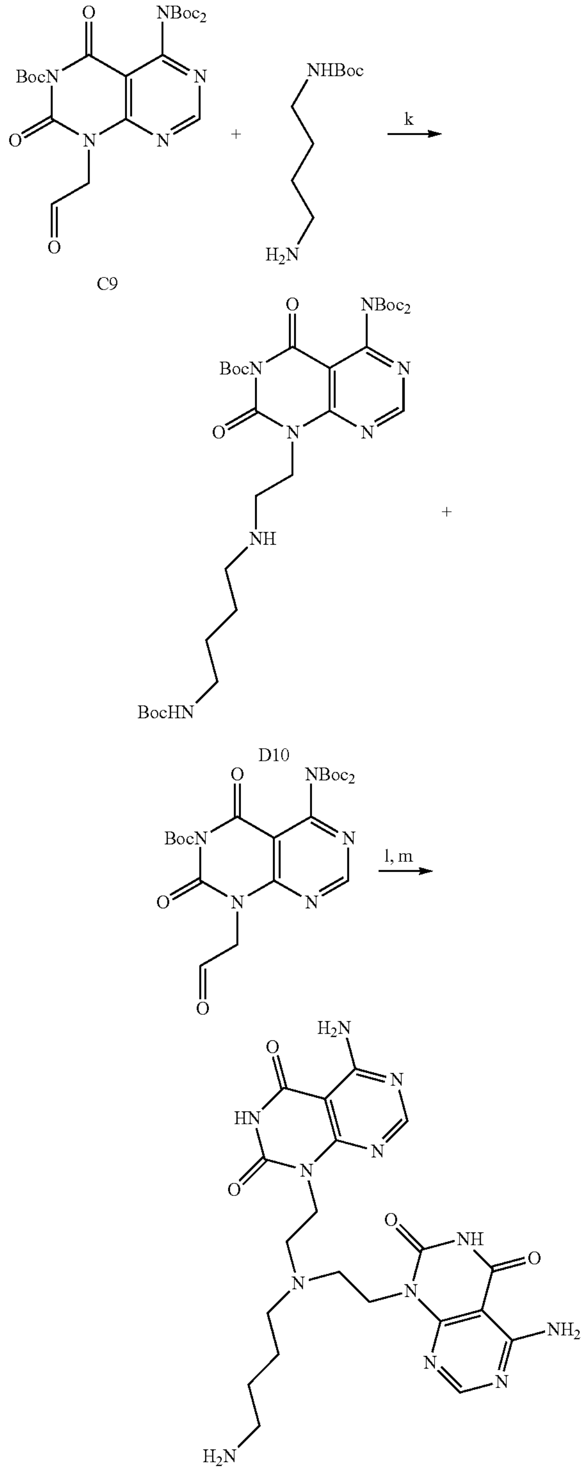

C9

D10

D

Scheme 3. (k) NaBH(OAc)3, 1,2-DCE, 16 h, r.t. (l) NaBH(OAc)3, 1,2-DCE, 16 h, r.t. (k) TFA, thioanisole, r.t., 72 h.

The final compound C was prepared from commercially available starting materials with a synthetic pathway generating intermediates C1-C7 to afford the final compound C. Likewise, final compound D was prepared from synthesized intermediate compound C9 to produce further compound intermediates D9 and D10 to yield the final compound D.

Synthesis of Compound C

Synthesis of Compound C1.

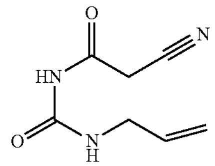

N-allylurea (10.4 g) and cyanoacetic acid (8.91 g) are dissolved in 20 mL acetic anhydride. Then the mixture is heated to 85° C., and stirred for 3 hours while the temperature is kept at 85° C. After completion, the brown reaction mixture is cooled to room temperature, and carefully added to 53 mL diethyl ether. Then mixture is kept on ice for 2 hours, before the precipitate is filtered out and washed with diethyl ether. After drying under vacuum, 10.35 g off-white needle shaped solid (compound C1) is obtained in a yield of 59.1%. $R_f$=0.66 (5% MeOH/DCM). $^1$H-NMR (400 MHZ, DMSO-$d_6$) δ (ppm): 10.61 ($C_4NHC_5$, br, s, 1H) 8.10 ($C_4NHC_3$, br, 1H), 5.85 ($C_2H$, m, 1H), 5.09 ($C_1H$, ddd, $J_1$=20.32 Hz, $J_1$=6.84 Hz, $J_1$=1.04 Hz, 2H), 3.92 ($C_6H$, s, 2H), 3.79 ($C_3H$, t, J=4.72 Hz, 2H). $^{13}$C-NMR (600 MHZ, $CDCl_3$) δ (ppm): 165.01 ($C_5$), 152.21 ($C_4$), 134.96 ($C_2$), 115.18, 115.04 ($C_{1,\ 7}$), 41.28 ($C_3$), 26.71 ($C_6$). HRMS (ESI) m/z calculated for $C_7H_9N_3O_2$+$H^+$ 168.0773. found 168.0768. Formula is confirmed as $C_7H_9N_3O_2$.

Synthesis of Compound C2

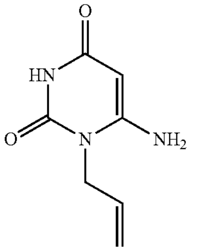

Compound C1 (5.17 g) is dissolved in 22.5 mL 2:1 water/ethanol solution. Slowly heat the reaction mixture to 85° C., then 10% sodium hydroxide (NaOH, by weight) solution is added to adjust pH to 10.0. All materials are dissolved at this time, and 10 min later yellow solid start to precipitate out. The reaction is kept at 85° C. for 2 hours, then is adjusted with 1N hydrochloric acid (HCl) to pH=5. After cooled to room temperature, reaction mixture is placed on ice for 30 min. Then white crystal (compound $C_2$) is filtered out and dried under vacuum for overnight. 3.22 g compound $C_2$ is obtained in a yield of 62.2%. $R_f$=0.54 (10% MeOH/DCM). $^1$H-NMR (400 MHZ, DMSO-$d_6$) δ (ppm): 10.35 ($C_4NHC_5$, br, s, 1H) 6.70 ($C_7NH$, br, 2H), 5.80 ($C_2H$, m, 1H), 5.09 ($C_1H$, ddd, $J_1$=20.32 Hz, $J_2$=7.00 Hz, $J_3$=0.96 Hz, 2H), 4.54 ($C_6H$, d, J=1.28 Hz, 1H), 4.39 ($C_3H$, d, J=3.12 Hz, 2H). $^{13}$C-NMR (600 MHz, $CDCl_3$) δ (ppm): 162.31 ($C_5$), 155.58 ($C_7$), 151.00 ($C_4$), 132.39 ($C_2$), 115.62 ($C_1$), 75.17 ($C_6$), 42.47 ($C_3$). HRMS (ESI) m/z calculated for $C_7H_9N_3O_2$+$H^+$ 168.0773. found 168.0764. Formula is confirmed as $C_7H_9N_3O_2$.

Synthesis of Compound C3.

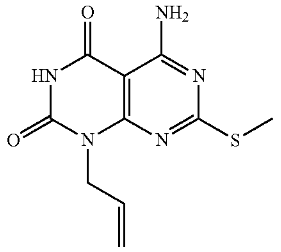 [SMILES: C=CCn1c(=O)[nH]c(=O)c2c(N)nc(SC)nc21]

Compound C2 (1.67 g), dimethyl cyanodithioiminocarbonate (1.46 g), and potassium carbonate (2.10 g) are mixed and dissolved in 30 mL N,N-dimethylformamide. The reaction mixture is then heated to 100° C. and kept for 5 hours. After completion the reaction mixture is poured onto 200 mL ice-water then acidified with 10% HCl to pH=3. Then this mixture is placed on ice for 30 min, white precipitation start to appear. And after setting mixture on ice overnight, white precipitate (compound C3) is filtered out, and the yield is 92.8%. $R_f$=0.52 (3% MeOH/DCM). $^1$H-NMR (400 MHZ, DMSO-$d_6$) δ (ppm): 11.61 ($C_4NHC_5$, br, s, 1H) 8.22 ($C_9NH$, br, d, J=8.92 Hz, 2H), 5.87 ($C_2H$, m, 1H), 5.13 ($C_1H$, q, J=1.48 Hz, 1H), 5.09 ($C_1H$, q, J=1.48 Hz, 1H), 3.92 ($C_6H$, s, 2H), 2.46 ($C_{10}H$, s, 3H). $^{13}$C-NMR (600 MHz, $CDCl_3$) δ (ppm): 174.81 ($C_5$), 162.77 ($C_7$), 161.65 ($C_5$), 157.16 ($C_9$), 149.85 ($C_4$), 132.62 ($C_2$), 116.51 ($C_1$), 86.67 ($C_6$), 43.03 ($C_3$), 13.14 ($C_{10}$). HRMS (ESI) m/z calculated for $C_{10}H_{10}N_5O_2S+H^+$ 266.0712. found 266.0710. Formula is confirmed as $C_{10}H_{10}N_5O_2S$.

Synthesis of Compound C4.

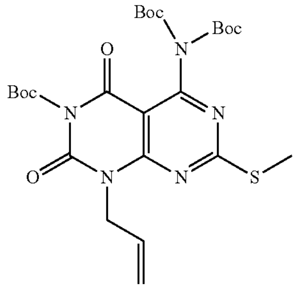 [SMILES: C=CCn1c(=O)n(C(=O)OC(C)(C)C)c(=O)c2c(N(C(=O)OC(C)(C)C)C(=O)OC(C)(C)C)nc(SC)nc21]

Compound C3 (6.72 g), 4-dimethylaminopyridine (3.1 g, DMAP), and triethylamine (28.3 mL, TEA) are added to tetrahydrofuran (250 mL, THF). Then di-tert-butyl dicarbonate (23.3 mL, $Boc_2O$) is added slowly to the reaction. The mixture is stirred at room temperature for 40 hours. Thin layer chromatography (TLC) is applied to identify the completion of reaction. Volatiles are removed under reduce pressure, the residue is taken up by 400 mL ethyl acetate, and then washed with water (150 mL), 10% citric acid (75 mL), water (100 mL×2), Sodium bicarbonate solution (100 mL), and brine (150 mL). Upon dry over anhydrous sodium sulfate and filtration, solvent of filtrate is removed under vacuum, resulting in a red/orange solid. This solid is purified by flash chromatography (0-25% ethyl acetate in hexanes over silica gel) to yield white foam (compound C4, 10.32 g, 71.9%).

Synthesis of Compound C5

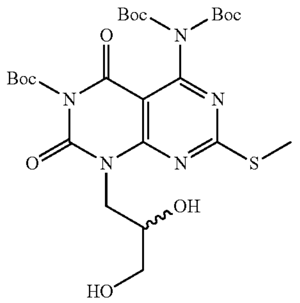 [SMILES: CSc1nc(N(C(=O)OC(C)(C)C)C(=O)OC(C)(C)C)c2c(=O)n(C(=O)OC(C)(C)C)c(=O)n(CC(O)CO)c2n1]

Compound C4 and 50% aqueous 4-methylmorpholine N-oxide (NMMO) are dissolved in acetone/water (8:1). After stirring at room temperature for 5 min, osmium tetroxide ($OsO_4$) (4% aqueous solution) is added drop wise over a period of 5 min. The resulting brown solution is stirring at room temperature for 22 hours, then quenched with aqueous sodium sulfite until solution turn to colorless. The di-ol product is extracted by chloroform, and then washed with water and brine. The organic layer is then dried over anhydrous sodium sulfate ($Na_2SO_4$), filtered, and evaporated to dryness under vacuum to yield white solid compound C5.

Synthesis of Compound C6

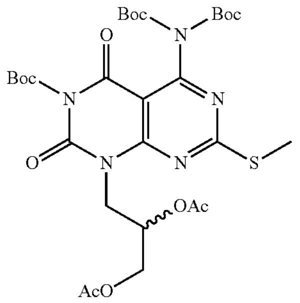 [SMILES: CSc1nc(N(C(=O)OC(C)(C)C)C(=O)OC(C)(C)C)c2c(=O)n(C(=O)OC(C)(C)C)c(=O)n(CC(COC(C)=O)OC(C)=O)c2n1]

Compound C5 is dissolved in THF, and then the reaction mixture is slowly added acetic anhydride and TEA, and stirred at room temperature for 12 hours. After reaction, volatiles are removed under reduced pressure; the residue is then taken up by ethyl acetate, and washed by 10% citric acid, water, sodium bicarbonate, water, and brine. Upon removal of the solvent, the crude product is got and purified through a gel flash chromatography to yield compound C6.

Synthesis of Compound C7

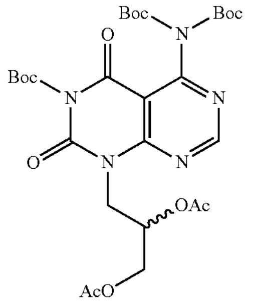 [SMILES: CC(=O)OCC(Cn1c(=O)n(C(=O)OC(C)(C)C)c(=O)c2c(N(C(=O)OC(C)(C)C)C(=O)OC(C)(C)C)ncnc21)OC(C)=O]

Compound C6 is dissolved in ethanol, and bubbled with nitrogen for 20 min. Raney nickel is added to the reaction, then mixture is heated to reflux for 24 hours. After TLC indicating the completion of reaction, reaction mixture is cooled to room temperature and filtered to remove nickel. The filtrate is then concentrated to yield compound C7.

Synthesis of Compound C8

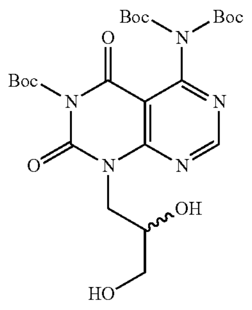

Compound C7 is dissolved in methanol, 7N ammonia in methanol is slowly added to the reaction flask, and then the reaction is kept stirring at room temperature for 10 hours. After TLC indicating the completion of reaction, volatiles are removed under reduced pressure to yield compound C8.

Synthesis of Compound C9

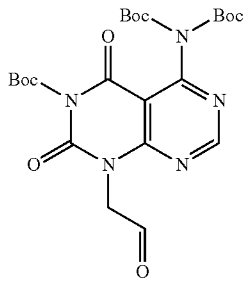 [SMILES: CC(C)(C)OC(=O)N(C(=O)OC(C)(C)C)c1ncnc2c1c(=O)n(C(=O)OC(C)(C)C)c(=O)n2CC=O]

Compound C8 and sodium periodate are dissolved in dichloromethane (DCM)/water mixture (4:1), and stirred for 36 hours. The mixture is filtered, and filtrate is then separated. The solvent in organic layer is removed under reduced pressure. And resulting residue is then purified through silica gel flash chromatography to yield compound C9.

Synthesis of Compound C10

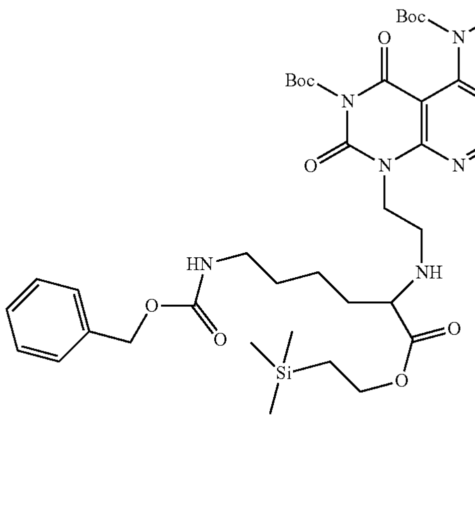

6-benzyloxycarbonylamino-2-L-amino-hexanoic acid trimethylsilylethyl ester and N,N-Diisopropylethylamine (DIPEA) are dissolved in 1,2-dichloroethane (1,2-DCE). A solution of compound C9 in 1,2-DCE is added to reaction mixture drop wise. After stirring at room temperature for 15 min, solid sodium triacetoxyborohydride ($NaBH(OAc)_3$) is added. The resulting solution is then stirred at room temperature for 16 hours, and then quenched with water. Aqueous layer is extracted with dichloromethane, and organic layer is combined and washed with 10% citric acid in water, water, and brine. After drying over $NaSO_4$, filtration and evaporation of solvent under reduced pressure are performed, and residue is then applied to a silica gel flash chromatography (5-30% ethyl acetate in hexanes) to yield compound C10.

Synthesis of Compound C

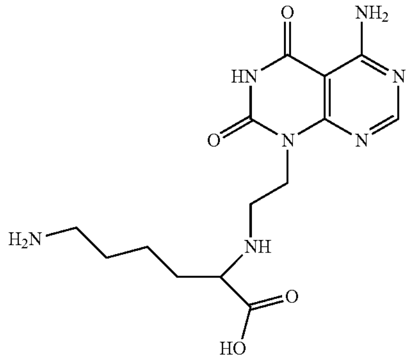 [SMILES: NCCCCC(NCCn1c(=O)[nH]c(=O)c2c(N)ncnc21)C(=O)O]

Compound C10 is added into 94% trifluoroacetic acid (TFA)/thioanisole solution. After stirring at room temperature for 72 hours, diethyl ether ($Et_2O$) is added. White precipitate of product compound C forms is then centrifuged and washed with $Et_2O$, methanol. The crude product is obtained as white solid, and purified by high pressure liquid chromatography (HPLC) to get pure product of white solid compound C. HPLC isolation of compound C is performed on a semi-prep Hypersil GOLD aQ column (150×10 mm L×W, particle size 5 um), the isolation program is listed below:

Solvent A: 100% DI water; Solvent B: 100% acetonitrile; Solvent C: pH=1 HCl water solution

| Time | A % | B % | C % |
|---|---|---|---|
| 0.00 min | 98.0 | 0 | 2.0 |
| 15.00 min | 68.0 | 30.0 | 2.0 |
| 25.00 min | 8.0 | 90.0 | 2.0 |
| 26.00 min | 0 | 100.0 | 0 |

Synthesis of Compound D

Synthesis of Compound D11

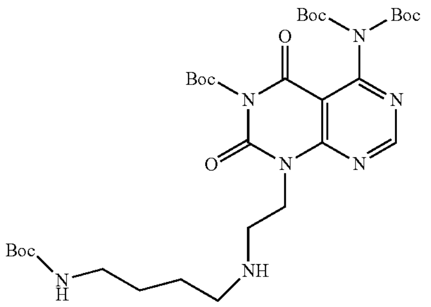 [SMILES: CC(C)(C)OC(=O)NCCCCNCCn1c(=O)n(C(=O)OC(C)(C)C)c(=O)c2c(N(C(=O)OC(C)(C)C)C(=O)OC(C)(C)C)ncnc21]

Commercial available N-Boc-1,4-diaminobutane is added to a solution of Compound C9 in 1,2-DCE at room temperature. Then the mixture is stirred for 1 hour, solid $NaBH(OAc)_3$ is added. The resulting solution is then stirred at room temperature for 15 hours. Aqueous layer is extracted with DCM, and organic layers are combined and washed with water, and brine. After drying over $NaSO_4$, filtration and evaporation of solvent under reduced pressure are performed, and residue is then applied to a silica gel flash chromatography (0-10% methanol in DCM) to yield white foam compound D11.

Synthesis of Compound D12

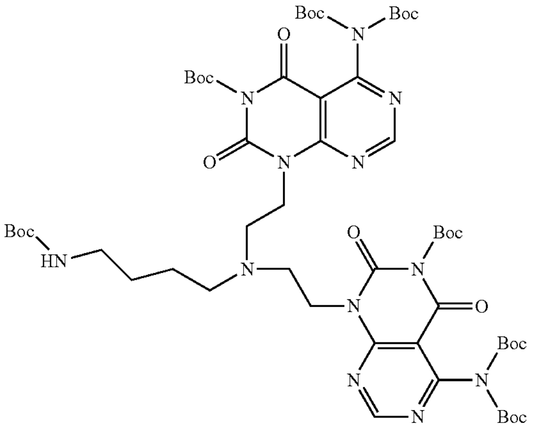 [SMILES: CC(C)(C)OC(=O)NCCCCN(CCn1c(=O)n(C(=O)OC(C)(C)C)c(=O)c2c(N(C(=O)OC(C)(C)C)C(=O)OC(C)(C)C)ncnc21)CCn1c(=O)n(C(=O)OC(C)(C)C)c(=O)c2c(N(C(=O)OC(C)(C)C)C(=O)OC(C)(C)C)ncnc21]

Compound D11 and compound C10 are dissolved in 1,2-DCE at room temperature, and stirred for 1 hour. Solid $NaBH(OAc)_3$ is added. The resulting solution is then stirred at room temperature for 15 hours. Aqueous layer is extracted with DCM, and organic layers are combined and washed with water, and brine. After drying over $NaSO_4$, filtration and evaporation of solvent under reduced pressure are performed, and residue is then applied to a silica gel flash chromatography (0-10% methanol in DCM) to yield white foam compound D12.

Synthesis of Compound D

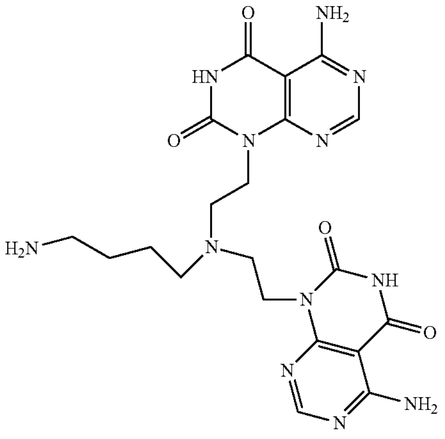 [SMILES: NCCCCN(CCn1c(=O)[nH]c(=O)c2c(N)ncnc21)CCn1c(=O)[nH]c(=O)c2c(N)ncnc21]

Compound D12 is added into 94% TFA/thioanisole solution. After stirring at room temperature for 72 hours, diethyl ether ($Et_2O$)) is added. White precipitate of product compound D forms, and is then centrifuged and washed with $Et_2O$, MeOH. The crude product is obtained as white solid, and purified by HPLC to get pure product of white solid compound D. HPLC isolation of compound D is performed on a semi-prep Hypersil GOLD aQ column (150×10 mm L×W, particle size Sum), the isolation program is listed below: Solvent A: 100% DI water; Solvent B: 100% acetonitrile; Solvent C: pH=1 HCl water solution

| Time | A % | B % | C % |
|---|---|---|---|
| 0.00 min | 98.0 | 0 | 2.0 |
| 15.00 min | 68.0 | 30.0 | 2.0 |
| 25.00 min | 8.0 | 90.0 | 2.0 |
| 26.00 min | 0 | 100.0 | 0 |

Also provided herein is a composition that includes a cargo molecule and a nanoparticle (e.g., a nanocarrier, where the nanocarrier (e.g., nanotube or nanopiece)) comprises a compound of Formula (I), (III), (V) or (VIII), and the cargo molecule includes a therapeutic agent or a diagnostic agent. Exemplary therapeutic agent includes, but is not limited to, a nucleic acid (e.g., siRNA, shRNA), a protein, a peptide, or a small molecule. Exemplary diagnostic agent includes, but is not limited to, a molecular probe or a molecular beacon. Such diagnostic agents and therapeutic agents are well known to those of skill in the art.

Assemblies

Figure 8:
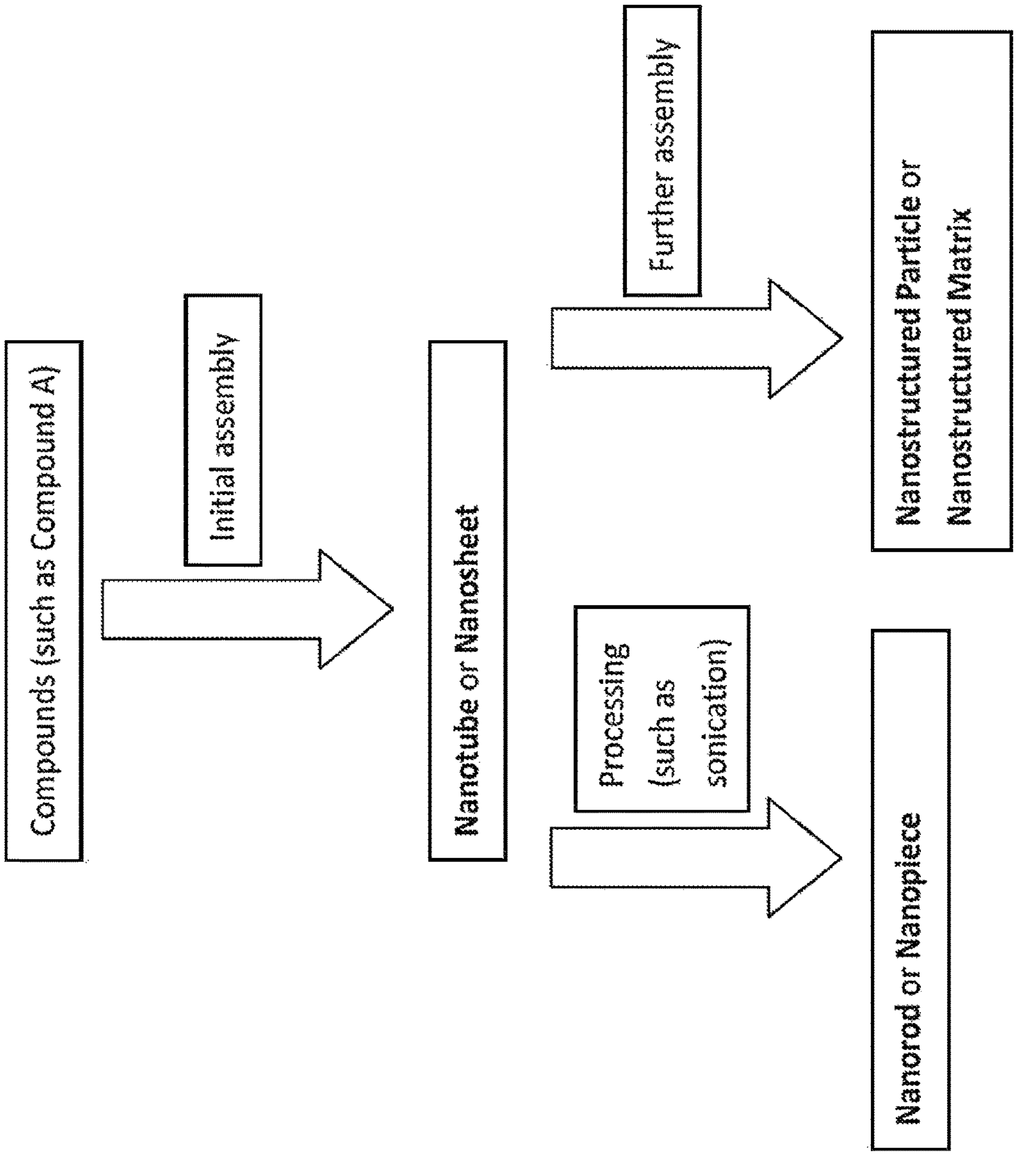
FIG. 8 is a flow chart illustrating exemplary embodiments of molecular assemblies formed from and/or comprising a compound or composition as described herein.

The compounds and compositions described herein can also be used for the preparation of molecular assemblies comprising one or more compounds and/or compositions described herein or formed from one or more compounds and/or compositions described herein. Exemplary, non-limiting assemblies (e.g., nanostructures) are described in Table A and in FIG. 8.

TABLE A

| Exemplary Molecular Assemblies | |
|---|---|
| Nanostructure | Characteristics |
| Nanotube | At least two dimensions ≤ about 100 nm; At least two aspect ratios (among height:width, width:length, and length:height) ≤ about 0.02 nm or ≥ about 50 nm. |
| Nanosheet | One dimension ≤ about 100 nm; One aspect ratio (among height:width, width:length, and length:height) ≤ about 0.02 nm or ≥ about 50 nm. |
| Nanorod | At least two dimension ≤ about 100 nm |
| Nanopiece | At least two dimension ≤ about 100 nm |
| Nanostructured Particle | At least two dimensions are between about 100 nm and about 1 μm |
| Nanostructured Matrix | At least two dimensions are ≥ about 1 μm |

In embodiments, the nanostructures can also comprise cargo molecules for, e.g., use as nanocarriers as described herein. In embodiments, a nanotube, nanosheet, nanopiece, nanostructured particle, or a nanostructured matrix, or any combination thereof, can be assembled in the presence of a cargo molecule (e.g., a diagnostic or therapeutic agent) as described herein. In embodiments, a composition comprises a nanotube, nanosheet, nanopiece, nanostructured particle, or a nanostructured matrix, or any combination thereof, and a cargo molecule (e.g., a diagnostic or therapeutic agent) as described herein.

Preparation and Use of Nanomaterial of the Invention

In embodiments, the compounds of the invention can be used as nanocarriers for delivering diagnostic or therapeutic agents into cells. These compounds are able to assemble into nanostructures including nanotubes and/or nanopieces and they mimic or structurally resemble a nucleic acid base pair.

Provided herein are methods for making a nanotube-agent complex. The methods include combining a solution of a compound of the invention with one or more agents (such as diagnostic or therapeutic agents, e.g., siRNA, molecular beacons), where the compound is self-assembled into nanotube, and the one or more agents are incorporated into the nanotube to form a complex of nanotube-agent(s), thereby delivering the agent(s).

Alternatively, the methods include combing a solution of a compound having Formula (I), (II), (III), (IV), (V), (VI), (VII), or (VIII) with one or more agents (such as diagnostic or therapeutic agents, e.g., siRNA, molecular beacons), where the compound is self-assembled into nanotube, and the one or more agents are incorporated into the nanotube to form a complex of nanotube-agent(s), thereby delivering the agent(s).

Also provided herein is a system for selective delivery of a drug or an agent into a bodily tissue or into a cell. The system includes a cargo molecule and a nanocarrier, where the nanocarrier (e.g., nanotube or nanopiece) comprises a compound of Formula (I), (III), (V) or (VIII), and the cargo molecule includes a therapeutic drug/agent or a diagnostic agent. Exemplary therapeutic drug/agent includes, but is not limited to, a nucleic acid (e.g., siRNA, shRNA), a protein, a peptide, or a small molecule. Exemplary diagnostic agent includes, but is not limited to, a molecular probe or a molecular beacon. Such diagnostic agents and therapeutic agents are well known to those of skill in the art.

In some embodiments, the cargo molecule includes a nucleic acid for anti-inflammation and/or joint degradation function, for example, but is not limited to interleukin-1 receptor type 1 siRNA, TNF-α siRNA, miRNA-365 antagomir, and miRNA-146a antagomir.

In one illustrative embodiment, the cargo molecule includes interleukin-1 receptor type 1 siRNA. The system for delivering this siRNA is prepared by diluting interleukin-1 receptor type 1 siRNA is in water, then mixing it with compound A nanotubes solution in a certain ratio (50 pmol siRNA to 5 ug nanotubes), vortexing well the mixture, sonicating the mixture, and spinning the liquid down.

In one illustrative embodiment, the cargo molecule includes TNF-α siRNA. The system for delivering this siRNA is prepared by diluting TNF-α siRNA in water, mixing with compound B nanotubes solution in a certain ratio (50 pmol siRNA to 10 ug nanotubes), and vortexing the mixture well, sonicating the mixture, and spinning the liquid down.

In one illustrative embodiment, the cargo molecule includes miRNA-365 antagomir. The system for delivering miRNA-365 antagomir is prepared by diluting miRNA-365 antagomir in saline, mixing with compound C nanotubes solution in a certain ratio (20 pmol miRNA-365 antagomir to 5 ug nanotubes), vortexing well, sonicating the mixture, and spinning the liquid down.

In one illustrative embodiment, the cargo molecule includes miRNA-146a antagomir. The system for delivering miRNA-146a antagomir is prepared by diluting miRNA-146a antagomir in water, mixing with compound D nanotubes solution in a certain ratio (50 pmol miRNA-146a antagomir to 4 ug nanotubes), vortexing well, sonicating the mixture, and spinning the liquid down.

In some embodiments, the cargo molecule includes a nucleic acid for anti-cancer function, for example, an Indian hedgehog homolog (Ihh) siRNA, miRNA-181a antagomir, a vascular endothelial growth factor (VEGF) siRNA.

In one illustrative embodiment, the cargo molecule includes an Ihh siRNA. The system for delivering an Ihh siRNA is prepared by diluting an Ihh siRNA in water, mixing with compound A nanotubes solution in a certain ratio (50 pmol siRNA to 20 ug nanotubes), and vortexing well, sonicating the mixture, and spinning the liquid down.

In one illustrative embodiment, the cargo molecule includes miRNA-181a antagomir. A system for delivering miRNA-181a antagomir is prepared by diluting miRNA-181a antagomirin saline, mixing with compound B nanotubes solution in a certain ratio (20 pmol miRNA-365 antagomir to 3 ug nanotubes), vortexing well, sonicating the mixture, and spinning the liquid down.

In one illustrative embodiment, the cargo molecule includes VEGF siRNA. A system for delivering the VEGF siRNA is prepared by diluting a VEGF siRNA in 5% glucose, mixing with compound C nanotubes solution in a certain ratio (50 pmol siRNA to 12.5 ug nanotubes), vortexing the mixture well, sonicating the mixture, and spinning the liquid down.

In some embodiments, the cargo molecule includes a molecular beacon, such as, but is not limited to, matrix metalloproteinase-13 (MMP-13) molecular beacon, a disintegrin and metalloproteinase with thrombospondin motifs-5 (ADAMTS-5) molecular beacon, miRNA-181a molecular beacon.

In one illustrative embodiment, the cargo molecule includes MMP-13 molecular beacon. A system for delivering MMP-13 molecular beacon is prepared by diluting MMP-13 molecular beacon in water, mixing with compound A nanotubes solution in a certain ratio (100 pmol molecular beacon to 5 ug nanotubes), vortexing the mixture well. Sonicate the mixture described in Step three, and then spin all liquid down In one illustrative embodiment, the cargo molecule includes ADAMTS-S molecular beacon. A system for delivering ADAMTS-5 molecular beacon is prepared by diluting ADAMTS-5 molecular beacon in water, mixing with compound C nanotubes solution in a certain ratio (100 pmol molecular beacon to 10 ug nanotubes), vortexing the mixture well. Sonicate the mixture described in Step three, and then spin all liquid down.

In one illustrative embodiment, the cargo molecule includes miRNA-181a molecular beacon. A system for delivering miRNA-181a molecular beacon is prepared by diluting miRNA-181a molecular beacon in saline, mixing with compound D nanotubes solution in a certain ratio (20 pmol molecular beacon to 5 ug nanotubes), vortexing the mixture well. Sonicate the mixture described in Step three, and then spin all liquid down.

In some embodiments, the cargo molecule includes a protein or a peptide, for example, but is not limited to, matrilin-3, cartilage oligomeric matrix protein (COMP) protein, insulin-like growth factor 1 (IGF-1).

In one illustrative embodiment, the cargo molecule includes matrilin-3. A system for delivering matrilin-3 is prepared by diluting matrilin-3 in water, mixing with compound A nanotubes solution in a certain ratio (200 ng matrilin-3 to Sug nanotubes) for 30 s. Matrilin-3 is further described in the PCT publication number WO12/094511, the content of which is incorporated herein as its entirety. The following table describes the GenBank IDs for each of the matrilins as found on the NCBI database, the contents of each of the Genbank citations below is hereby incorporated by reference.

| Gene | Species | GenBank mRNA Reference sequence |
|---|---|---|
| MATN1 | human | NM_002379.3 |
| MATN2 | human | NM_002380.3 (Transcrip. Var. 1) |
| | | NM_030583.2 (Transcrip. Var. 2) |
| MATN3 | human | NM_002381.4 |
| MATN4 | human | NM_003833.3 (Transcrip. Var. 1) |
| | | NM_030590.2 (Transcrip. Var. 2) |
| | | NM_030592.2 (Transcrip. Var. 3) |

Matrilin-3 is a protein (NP_002372.1) that in humans is encoded by the MATN3 gene. Matrilin-1 has an amino acid sequence of NP_002372.1. Active domains or fragments of matrilins are known in the art.

In one illustrative embodiment, the cargo molecule includes COMP protein. A system for delivering COMP protein is prepared by diluting COMP protein in HBSS, mixing with compound C nanotubes solution in a certain ratio (100 ng protein to 10 ug nanotubes) for 3 mins.

In one illustrative embodiment, the cargo molecule includes IGF-1. A system for delivering IGF-1 is prepared by diluting IGF-1 in saline, mixing with compound B nanotubes solution in a certain ratio (1 μg protein to 5 ug nanotubes) for 30 mins.

In some embodiments, the cargo molecule includes a small molecule, for example, but is not limited to, Pemetrexed, Dexamethasone, tamoxifen, and Doxorubicin.

In one illustrative embodiment, the cargo molecule includes Pemetrexed. A system for delivering Pemetrexed is prepared by diluting Pemetrexed in water, and mixing with compound B nanotubes solution in a certain ratio (Sug Pemetrexed to Sug nanotubes) for 1 s In one illustrative embodiment, the cargo molecule includes Dexamethasone. A system for delivering Dexamethasone is prepared by diluting Dexamethasone in HBSS, and mixing with compound C nanotubes solution in a certain ratio (100 μg Dexamethasone to 10 ug nanotubes) 5 mins.

In one illustrative embodiment, the cargo molecule includes tamoxifen. A system for delivering tamoxifen is prepared by diluting tamoxifen in PBS, and mixing with compound D nanotubes solution in a certain ratio (1 μg tamoxifen to 5 ug nanotubes) for 24 hours.

In one illustrative embodiment, the cargo molecule includes Doxorubicin. A system for delivering Doxorubicin is prepared by diluting Doxorubicin in PBS, and mixing with compound D nanotubes solution in a certain ratio (1 μg Doxorubicin to 5 ug nanotubes) for 24 hours.

In some embodiments, the cargo molecule includes a drug, a fluorescent material, a radioisotope, a target-oriented material, an imaging material, a cell, a protein drug, an antibody, or an aptamer.

For example, the drug is at least one selected from the group consisting of paclitaxel, doxorubicin, docetaxel, 5-fluoreuracil, oxaliplatin, cisplatin, carboplatin, berberine, epirubicin, doxycycline, gemcitabine, rapamycin, tamoxifen, Herceptin™ (trastuzumab), Avastin™ (bevacizumab), Tysabri™ (natalizumab), Erbitux™ (cetuximab), Campath™ (alemtuzumab), Zevalin™ (ibritumomab tiuxetan), Humira™ (adalimumab), Mylotarg™ (gemtuzumab ozogamicin), Xolair™ (omalizumab), Bexxar™ (tositumomab and iodine I 131 tositumomab), Raptiva™ (efalizumab), Remicade™ (infliximab), siRNA, aptamer, interferon, insulin, Reopro™ (abciximab), Rituxan™ (rituximab), Zenapax™ (daclizumab), Simulect™ (basiliximab), Orthoclone™ (muromonab-CD3), Synagis™ (palivizumab), erythropoietin, epidermal growth factor (EGF), human growth hormone (hGH), thioredoxin, Fel d1, Bee Venom Phospholipase A2 (Api m1), myelin basic protein, Hsp60, and Chaperone DnaJ (Hsp 40).

For example, the fluorescent material is at least one selected from the group consisting of fluorescein, rodamine, Dansyl, Cyanine dye (Cy), and antracene.

For example, the radioisotope is at least one selected from the group consisting of $^{3}H$, $^{14}C$, $^{22}Na$, $^{35}S$, $^{33}P$, $^{32}P$, and $^{125}I$.

For example, the target-oriented material is a peptide comprising at least one selected from the group consisting of RGD (arginine-leucine-aspartic acid), TAT (threonine-alanine-threonine), and MVm (methionine-valine-D-methionine); a peptide recognizing a specific cell; an antigen; an antibody; folic acid; nucleic acid; an aptamer; and a carbohydrate.

For example, the imaging material is at least one selected from the group consisting of a gadolinium (Ga)-complex selected from gadolinium-diethylenetriamine penta-acetic acid (Ga-DTPA), gadolinium-diethylenetriamine penta-acetic acid-BMA (Ga-DTPA-BMA), gadolinium-tetraazacyclododecanetetraacetic acid (Ga-DOT), and Gadolinium-(1,4,8,11-tetraazacyclotetradecane) (Ga-cyclam).

Further exemplary uses of the compounds for delivering agent(s) are described below.

The UV absorbance spectrum of Compound A displays a two-peak model within 200 nm to 332 nm range. Spectrum is taken by Nanodrop 2000® (Thermo Scientific). 1 uL 0.15 g/L pure Compound A (pH=3.05) in water is placed on Nanodrop 2000®, and scanned 3 times (from 200 nm to 332 nm). The result is average of three scans (FIG. 1).

Compound A, B, C, D can self-assemble into nanotubes (in embodiments, nanotubes are long, thin cylinders of atoms; for example, nanotubes can be unique for their size, shape, and physical properties) in aqueous solution at pH=1 to pH=14.

Nanotubes Formed from Compound A

Figure 2:
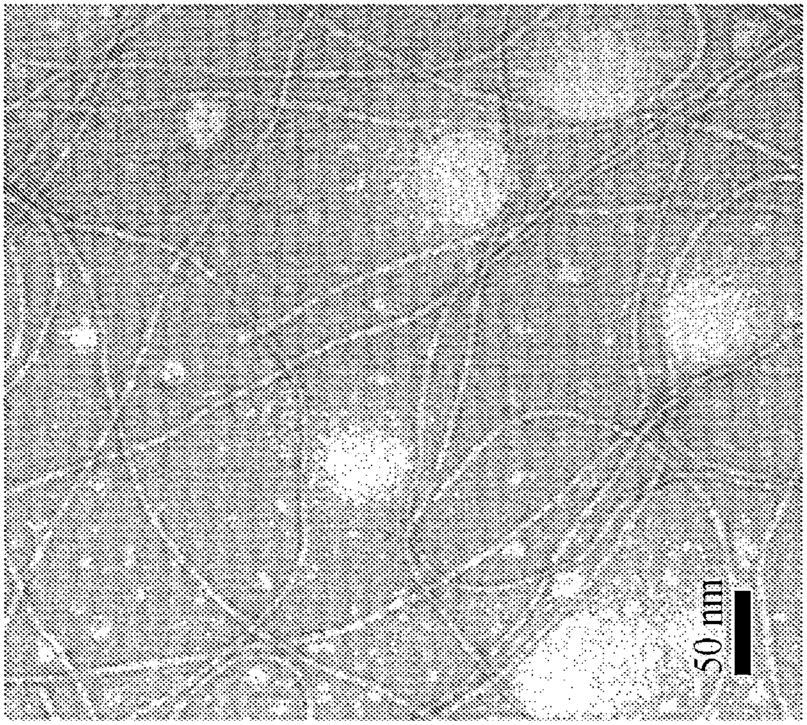
FIG. 2 is an image showing transmission electron microscope (TEM) scan of Compound A nanotubes.

A negatively stained transmission electron microscopy (TEM) picture example of nanotubes formed by Compound A is shown as in FIG. 2, which provided the visual evidence of formation of nanotubes.

The sample of Compound A is prepared as below: 200 mesh formvar carbon coated copper grid is floated on 3 μL of 0.5 mg/mL Compound A in water (pH=3.05) for 1 min, transferred to 3 μL of 2% aqueous uranyl acetate for about Imin, blotted, dried and viewed under Philips® CM10 model TEM with Gatan® Erlangshen ES1000W lens at 80 kv and 92,000× magnification, the black bar in the picture represent 50 nm. The software used to obtain pictures is Digital Micrograph® (TM) 1.71.38.

To assemble into nanopieces, 1 mg/mL aqueous solution of compound A, B, C, or D is made and well mixed, and following steps below:

Step one: Dilute molecular beacon or siRNA in water, then mix with compound A, B, C, or D nanotubes solution in a certain ratio (50 pmol siRNA or 100 pmol molecular beacon to Sug), then vortex well.

Step two: Sonicate the mixture and then spin all liquid down. Nanopieces were assembled after Step two.

Figure 3:
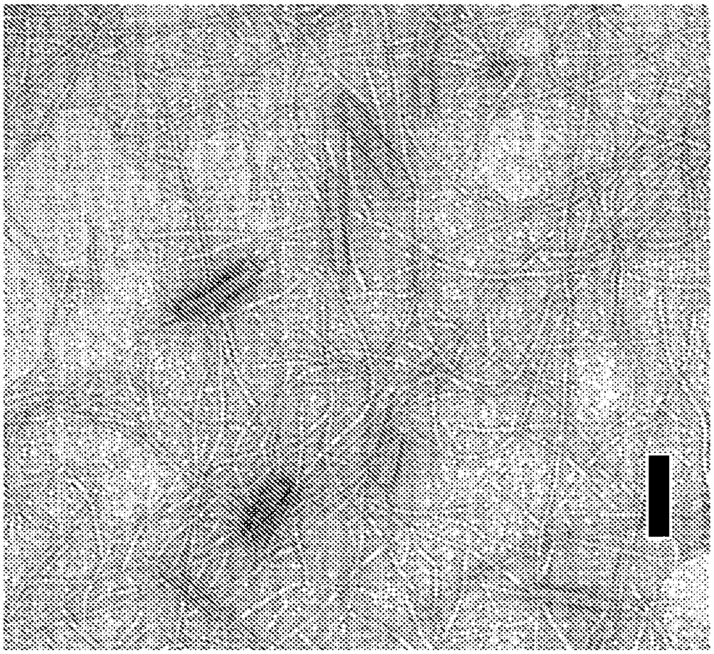
FIG. 3 is a TEM image showing nanopieces formed by Compound A.

The TEM picture of FIG. 3 is an example of nanopieces formed by Compound A (FIG. 3).

The sample of nanomaterial is prepared as below: 200 mesh formvar carbon coated copper grid is floated on 3 μL of 0.5 mg/mL Compound A Nanopieces in water for 1 min, transferred to 3 μL of 2% aqueous uranyl acetate for about Imin, blotted, dried and viewed under Philips® CM10 model TEM with gatan Erlangshen ES1000W lens at 80 kv and 46,000× magnification, the black bar in the picture represent 100 nm. The software used to obtain pictures is Digital Micrograph® (TM) 1.71.38.

Figure 4:
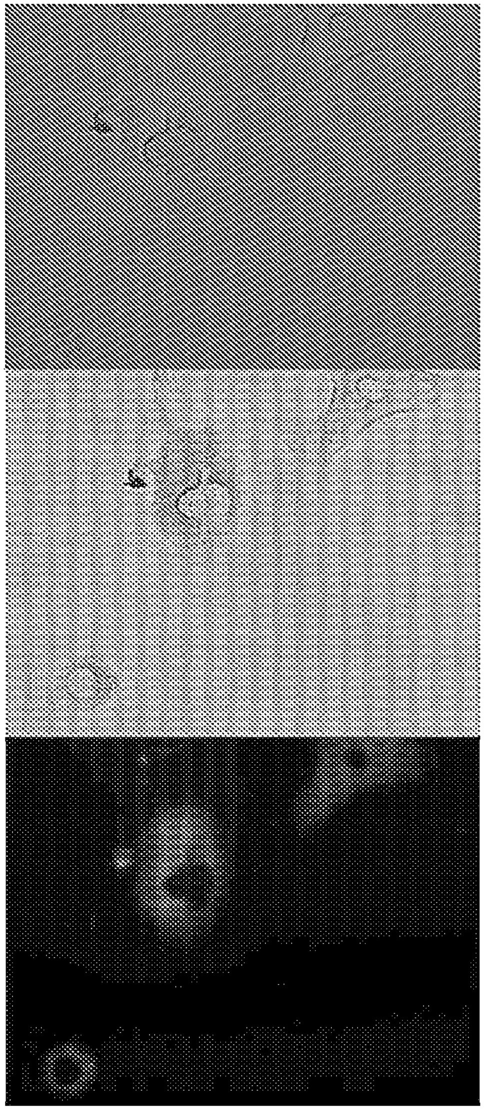
FIG. 4 is a panel of images showing successful and functional delivery of nucleic acids into cells. The left panel shows fluorescence indicating a successful delivery of Compound A and molecular beacons (nucleic acids based molecular probes that only emit fluorescence after being delivered into cells and bind with the target mRNA). The middle panel shows the cells and the right panel is the overlap of the left and the middle panels.

The delivery ability was also tested. Firstly, Compound A and molecular beacons (nucleic acids based molecular probes, only emits fluorescence after being delivered into cells and bind with the target mRNA.) targeting a house keeping gene, GAPDH, were assembled into Nanopieces and cultured with ATDC5 cells under standard cell culture conditions. 24 hours later, cells were rinsed with fresh HBSS to remove Nanopieces in the culture medium and on the cell surface. Cells were then observed under a fluorescence microscope. Red fluorescence was observed inside cells demonstrating successful and functional delivery of nucleic acids into cells (FIG. 4).

Figure 5:
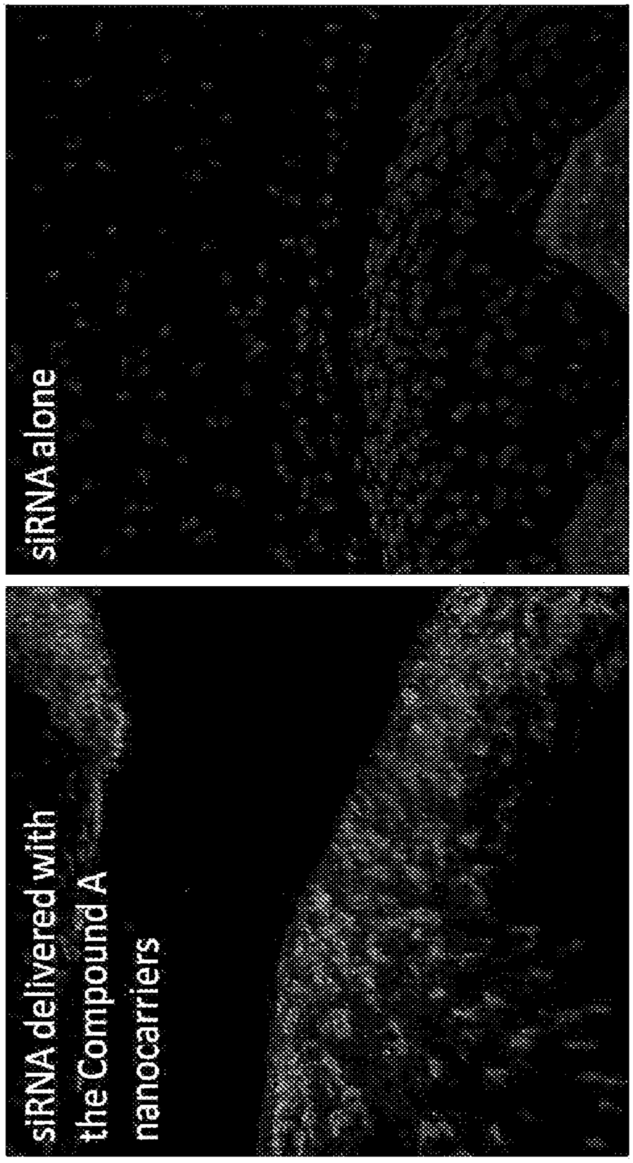
FIG. 5 is a panel of images showing successful delivery of siRNA into cartilage and chondrocytes. Left panel shows nanopieces delivered with fluorescence labeled siRNA and the right panel shows siRNA alone.
Figure 6:
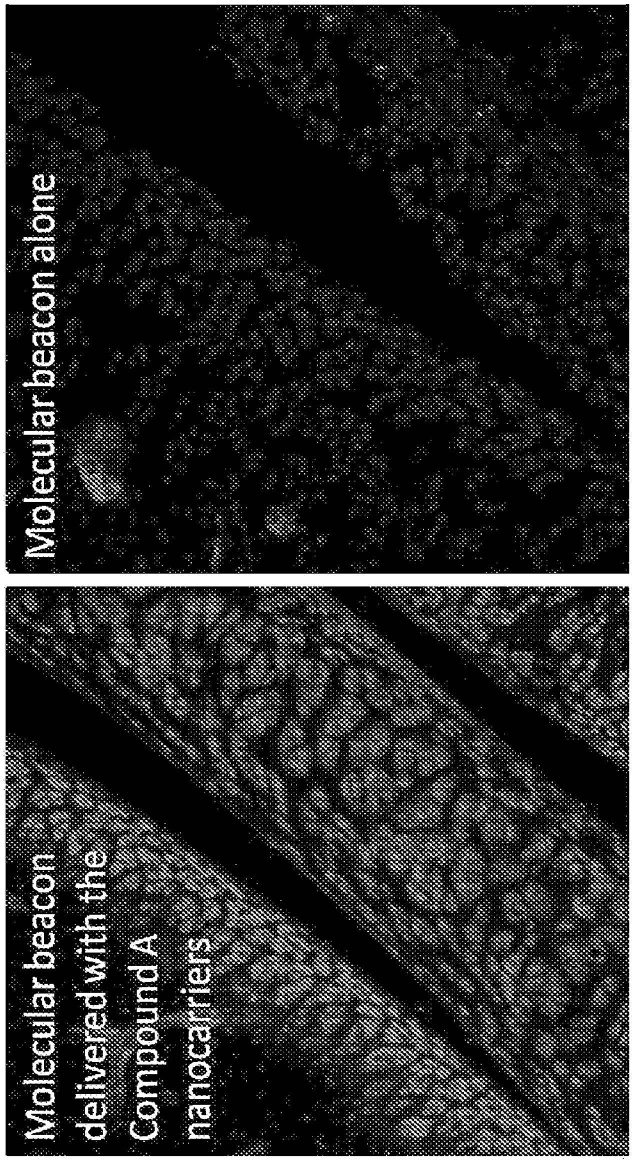
FIG. 6 is a panel of images showing successful and functional delivery of molecular beacons into cartilage and chondrocytes. Left panel shows nanopieces delivered with fluorescence labeled molecular beacons and the right panel shows molecular beacons alone.

Moreover, the forming Nanopieces are capable to penetrate into knee joint cartilage in vivo, and deliver both siRNA (FIG. 5) and molecular beacons (FIG. 6) into chondrocytes in cartilage. Briefly, Nanopieces delivered with fluorescence labeled siRNA or molecular beacons (targeting GAPDH) were injected into the knee space of adult rats. After 24 hours, animals were euthanized and their knee joints were harvested and prepared for histology observation under a fluorescence microscope.

Figure 7:
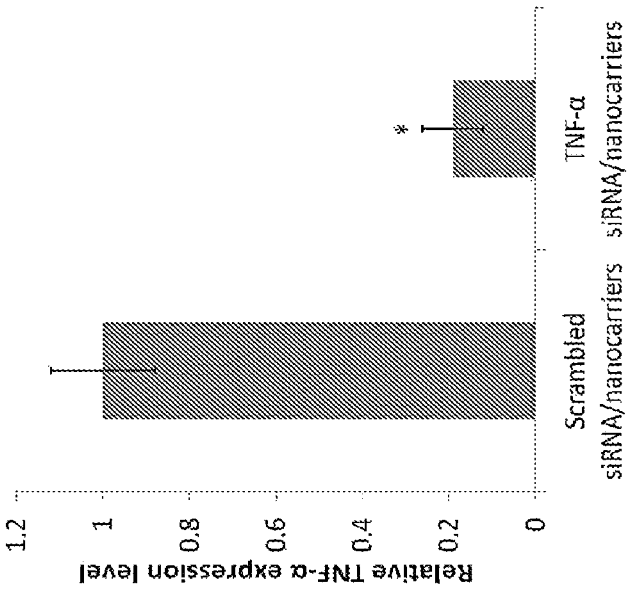
FIG. 7 is a bar graph showing functional knock-down of TNF-α using the siRNA delivered by Compound A nanocarriers.

To test the knock down efficiency of Compound A nanocarriers, scrambled siRNA or TNF-α siRNA were delivered via Compound A nanocarriers into rat macrophages (FIG. 7). Briefly, 0.1 μg/mL LPS was used to induce TNF-α expression and Compound A nanocarriers delivered with scrambled siRNA or TNF-α siRNA were cultured with the cells for 24 hours. Then, the cells were harvested and their gene expression was measured via real time RT-PCR.

The nanomaterial (compound) described herein can also be used for implant, coating an implant/device, tissue engineering, and/or device for tissue healing, regeneration and/or repair.

In some embodiments, the nanomaterial (compound) described herein is used for an implant.

In some embodiments, an implant includes a composition that comprises a nanostructured matrix, where the nanostructured matrix is formed by a compound described herein.

In some embodiments, the implant also comprises matrilin. Typically, the matrilin is Matrilin-3.

In some embodiments, the implant also comprises an orthopedic implant.

In some embodiments, the implant further includes a bioactive agent or an immunosuppressive agent.

Bioactive agents are also known in the art. For example, bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof. Additional, or alternative non-limiting examples of agents include collagen, drugs, antibodies, peptides, peptidomimetics, oligonucleotides, chemical entities, growth factors, and mixtures thereof.

Examples of bone morphogenic proteins (BMP) include: BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18. Vascular endothelial growth factors (VEGF) include VEGF-A, VEGF-B, VEGF-C, VEGF-D and VEGF-E. Connective tissue growth factors (CTGF) include CTGF-1, CTGF-2, and CTGF-4, Growth differentiation factors (GDFs) include GDF-1, GDF-2, GDF-3, GDF-7, GDF-10, GDF-11, and GDF-15. Cartilage-derived morphogenic proteins (CDMPs) include CDMP-1 and CDMP-2. LIM mineralization proteins (LMPs) include LMP-1, LMP-2, and LMP-3. Transforming growth factor beta (TGFβ) include TGFβ-1, TGFβ-2, and TGFβ-3.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FKS06, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

Also provided is a method for making an implant. The method includes preparing a solution including a compound; forming in the solution a matrix suitable for implant, where the matrix includes a nanostructured matrix formed by a compound described herein.

Such implant can be used for healing a tissue, which includes steps of preparing an implant according to the method described above, and administering the implant into a tissue in need of an implant, thereby healing the tissue. Typically, the tissue (e.g., bone, cartilage) has a growth plate fracture or defect. Typically, the implant is placed into the fracture or defect.

In some embodiments, the nanomaterial (compound) described herein is used for coating a device/implant.

In some embodiments, a system for coating a device includes a composition that comprises a solution of a compound described herein.

In some embodiments, a method for coating a device/implant includes steps of applying a composition that comprises a solution of a compound described herein to the device/implant, where the solution includes nanotubes formed by a compound described herein.

In some embodiments, the coating solution further includes an immunosuppressive agent. For example, immunosuppressive agents that can be utilized include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FK506, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

In some embodiments, the nanomaterial (compound) described herein is used for tissue engineering.

In some embodiments, a composition for tissue engineering includes a nanomaterial, where the nanomaterial comprises a compound described herein.

In some embodiments, the composition for tissue engineering further includes a biodegradable polymer. Exemplary biodegradable polymer includes, but is not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), copolymers, and terpolymers.

In some embodiments, the composition for tissue engineering further includes a bioactive agent and/or an inert agent. For example, bioactive agent is bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof. For example, an inert agent is a carrier, an excipient, a sterilizing solution, and/or a labeling solution.

Examples of antibiotics useful with the biocompatible composite material include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™ (cyclosporine), Neoral™ (cyclosporine), Sangdya™ (cyclosporine), Prograf™ (FK506, tacrolimus), Cellcept™ (mycophenolate motefil), of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

As will be appreciated by those in the art, bioactive agents can be polypeptides, including full length polypeptides, biologically active fragments thereof, and fusion proteins, small molecules, and cells expressing such bioactive agents. Furthermore, the concentrations of the bioactive agent can be variable based on the desired length or degree of activity required.

In some embodiments, the composition for tissue engineering further includes a metal or ceramics.

In some embodiments, a method for tissue engineering includes steps of administering the composition for tissue engineering described herein to a tissue, where the nanomaterial is fabricated and solidified with blood of said tissue, thereby facilitating the tissue growth for tissue engineering.

In some embodiments, a method for making a device for tissue repair includes the steps of preparing a composition that comprises a compound of the invention and a peptide, forming a device that includes a structural element and the composition. Typically, the peptide is covalently linked to the compound. Typically, the structural element comprises a polysaccharide polymer material. For example, the polysaccharide polymer material comprises an agarose or a hydrogel. For example, agarose comprises a solution comprising 5% (w/w) agarose. Typically, the device comprises a specific shape that fits into a defect tissue or is malleable to form into a shape of a defect tissue.

Still further exemplary uses of the compounds, compositions, and molecular assemblies described herein include, but are not limited to, the following examples.

Implants:

Compound A is dissolved in saline for 12 hours at 0.1 mg/mL with matrilin-3 to assemble into nano-structured matrix. Then, the matrix is injected into the growth plate fracture site for tissue healing.

Coatings:

Compound B is dissolved in water for 1 min at 1 mg/mL to assemble into nanotubes. Then, a titanium fixation device or other device introduced into a bodily tissue such as bone, cartilage or other tissue is dipped into the solution and air-dried. The Compound A nanotubes are coated on the device and lead to better bio-integration of the device into the tissue.

Tissue Engineering Applications:

A 1 mm articular cartilage defect is created in adult mice. Then, 10 μg Compound C is applied (e.g., injected, infused or packed into) to the defect. For example, the compound is fabricated and solidified with blood or other cells or bodily solutions of the recipient animal such as human or mouse, and it facilitates cartilage regeneration of the animal.

Devices:

Compound D is covalently linked with a cell adhesion molecule such as the peptide (RGD). Then the compound is co-solidified with a polymer, e.g., a hydrogel such as 5% agarose with a specific shape to fit into a cartilage defect for cartilage repair.

Definitions

The term "amino acid" is inclusive of the 20 common amino acids, also called natural amino acids or α-amino acids, as well as "nonstandard amino acids," for example, D-amino acids and chemically (or biologically) produced derivatives of "common" amino acids, including for example, β-amino acids. Accordingly, amino acids according to the present disclosure include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present disclosure include lysine, arginine, serine, glycine, aspartate and the like.

The term "peptide" is inclusive of both straight and branched amino acid chains, as well as cyclic amino acid chains, which comprise at least 2 amino acid residues. The terms "peptide" and "polypeptide" are used interchangeably herein. Accordingly, polypeptides according to the present disclosure include two or more amino acids covalently linked together. According to one aspect, the two or more amino acids are covalently linked together at least in part by one or more peptide bonds.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences. As used herein, one of skill in the art will understand that the term "nucleic acid probe" includes probes known as molecular beacons which include synthetic oligonucleotide hybridization probes that can report the presence of specific nucleic acids in homogenous solutions or in cells. Species of molecular beacons include hairpin shaped molecules with an internally quenched fluorophore whose fluorescence is restored when they bind to a target nucleic acid sequence. Technically, molecular beacons can be designed to target any gene and can be linked with fluorescent molecules of different fluorescence wavelengths.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "subject" as used herein includes all members of the animal kingdom. In some aspects, the subject is a mammal, and in some aspects, the subject is a human of general population. The methods are also applicable to companion animals such as dogs and cats as well as livestock such as cows, horses, sheep, goats, pigs, and other domesticated and wild animals. In some embodiments, the subject is a human with a tissue defect.

The term "aliphatic" is used for non-aromatic compounds and substituents. Non-aromatic compounds may be alkyl, alkenyl, alkynyl, and/or carbocyclic.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amino, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, “lower alkenyl” and “lower alkynyl” have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

“Alkenyl” and “Alkynyl”, as used herein, refer to unsaturated aliphatic groups containing one or more double or triple bonds analogous in length (e.g., $C_2$-$C_{30}$) and possible substitution to the alkyl groups described above.

The term “nanostructure” refers to a chemical structure comprising one or more spatial dimensions on the nanoscale. In embodiments, a spatial dimension in on nanoscale is independently between about 1 to about 500 nm or about 1 to about 100 nm. In embodiments, a nanostructure has one dimension on the nanoscale (e.g., a surface or film where the thickness on in the nanoscale). In embodiments, a nanostructure has two dimensions on the nanoscale (e.g., a nanotube). In embodiments, a nanostructure has three dimensions on the nanoscale (e.g., a spherical nanoparticle). In embodiments, a nanostructure can further assemble into higher-ordered structures, and may have larger size to beyond nanoscale.

The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, π-π interactions or hydrophilic/hydrophobic effects to form relatively stable entities, which are referred to herein as “nanopieces The term “nanosheet” refers to a two-dimensional nanostructure. In embodiments, a nanosheet may have a thickness ranging from 1 to 100 nm.

The term “nanowhisker” refers to a filamentary nanostructure. In embodiments, a nanowhisker has a cross sectional diameter that is about 1 to about 100 nm. In embodiments, a nanowhisker has length to diameter ratio that is greater than about 100:1.

Example 1: A Compound Having the Formula

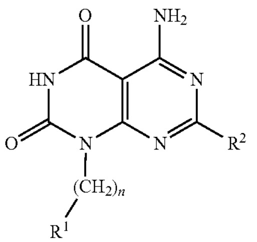

Where n is integer from 1 to 6.

And $R^1$ is α or β-amino acid (amino acid here refer to both D- and L-amino acid) having an α or β-amino group covalently bound to a carbon of the $(CH_2)_n$; or poly-α or β-peptide having a terminal α or β-amino group covalently bound to carbon of the $(CH_2)_n$. n is integers starting from 0. Following structures are some examples of α or β-amino acids:

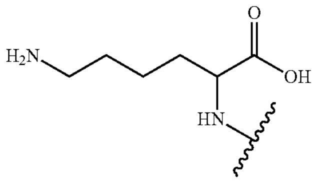

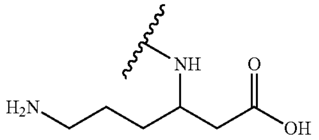

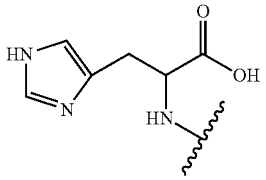

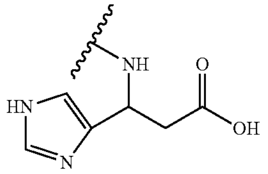

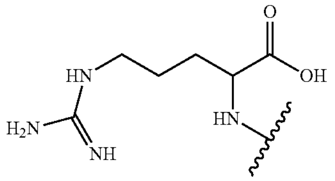

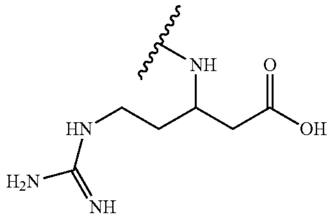

$R^1$ structure should also include structures shown below:

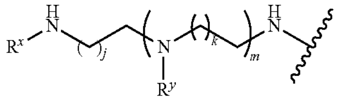 and

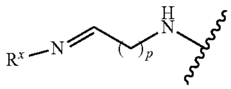

Within the structure above j is integer starting from 0, k is integer starting from 0, m is integer starting from 0, p is integer starting from 0; $R^x$ are aliphatic or hydrogen; $R^y$ is hydrogen or structure shown below:

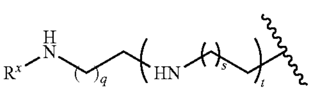

where q, s and t are integers starting from 0.

And $R^2$ is hydrogen, methyl, amino group or structure below:

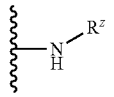

where $R^z$ is aliphatic.

Example 2: A Compound Having the Formula

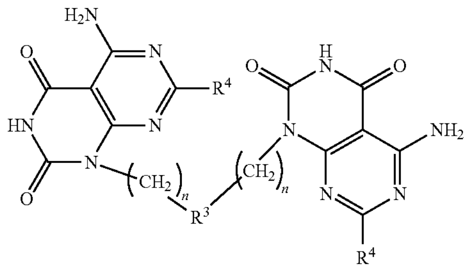

Where n is integer from 1 to 6.

And $R^3$ is α or β-amino acid (amino acid here refer to both D- and L-amino acid) having an α or β-amino group covalently bound to carbon of two $(CH_2)_n$ linkers; or poly-α or β-peptide having a terminal α or β-amino group covalently bound to carbon of two $(CH_2)_n$ linkers. Following structures are some examples of α or β-amino acids:

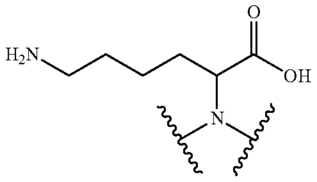

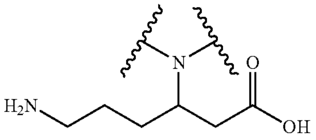

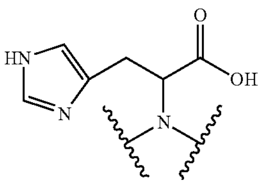

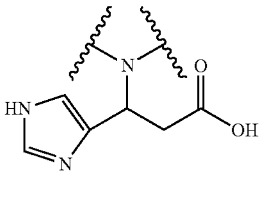

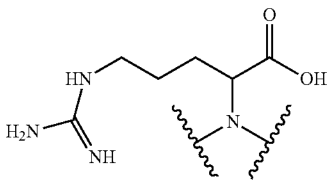

-continued

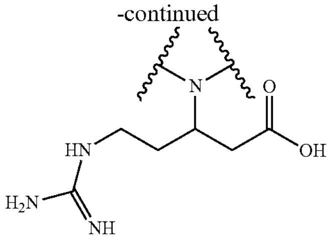

$R^3$ structure should also include structures shown below:

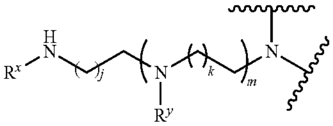

and

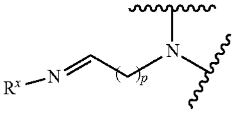

Within the structure above k is integer starting from 0, m is integer starting from 0, p is integer starting from 0; $R^x$ are aliphatic or hydrogen; $R^y$ is hydrogen or structure shown below:

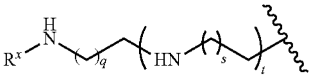

where q, s and/are integers starting from 0.

And $R^4$ is hydrogen, methyl, amino group or structure below:

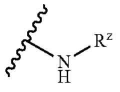

where $R^z$ is aliphatic.

Example 3: A Compound Having the Formula

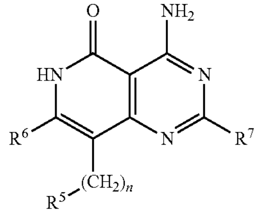

Where n is integer from 1 to 6.

And $R^5$ is α or β-amino acid (amino acid here refer to both D- and L-amino acid) having an α or β-amino group covalently bound to a carbon of the $(CH_2)_n$; or poly-α or β-peptide having a terminal α or β-amino group covalently bound to carbon of the $(CH_2)_n$. Following structures are some examples of α or β-amino acids:

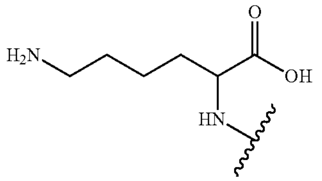

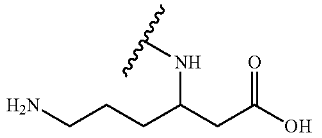

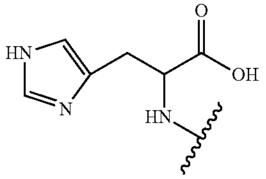

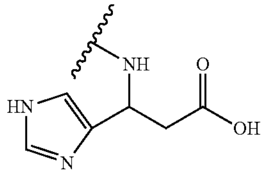

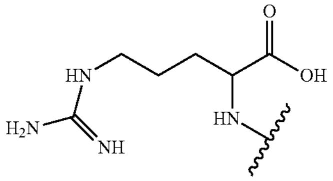

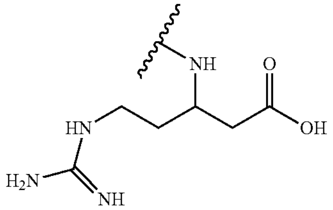

$R^5$ structure should also include structures shown below:

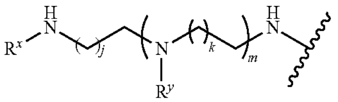

and

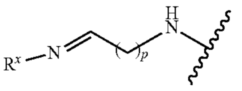

Within the structure above j is integer starting from 0, k is integer starting from 0, m is integer starting from 0, p is integer starting from 0; $R^x$ are aliphatic or hydrogen; $R^y$ is hydrogen or structure shown below:

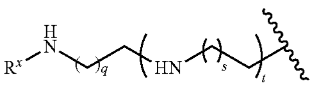

where q, s and/are integers starting from 0.

And $R^6$ and $R^7$ are respectively hydrogen, methyl, amino group or structure below:

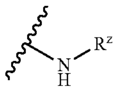

where $R^z$ is aliphatic.

Example 4: A Compound Having the Formula

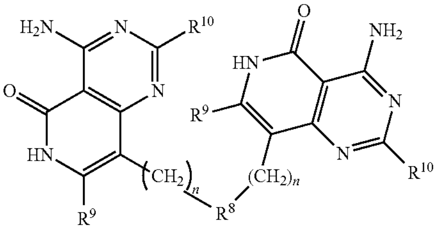

Where n is integer from 1 to 6.

And $R^8$ is α or β-amino acid (amino acid here refer to both D- and L-amino acid) having an α or β-amino group covalently bound to carbon of two $(CH_2)_n$ linkers; or poly-α or β-peptide having a terminal α or β-amino group covalently bound to carbon of two $(CH_2)_n$ linkers. Following structures are some examples of α or β-amino acids:

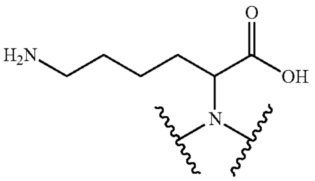

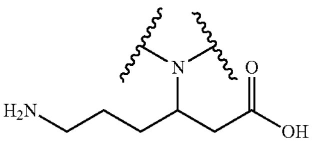

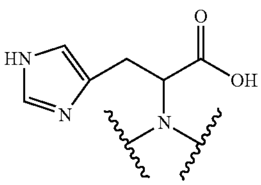

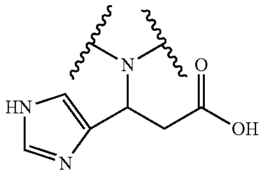

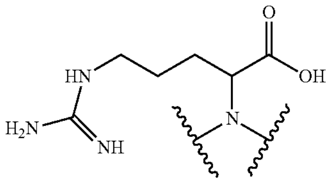

-continued

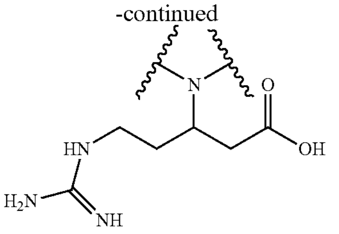

$R^8$ structure should also include structures shown below:

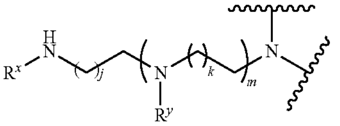

and

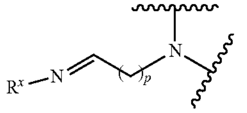

Within the structure above k is integer starting from 0, m is integer starting from 0, p is integer starting from 0; $R^x$ are aliphatic or hydrogen; $R^y$ is hydrogen or structure shown below:

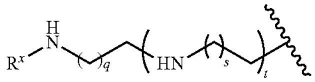

where q, s and/are integers starting from 0.

And $R^9$ and $R^{10}$ are respectively hydrogen, methyl, amino group or structure below:

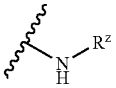

where $R^2$ is aliphatic.

Example 5: A Compound Having the Formula

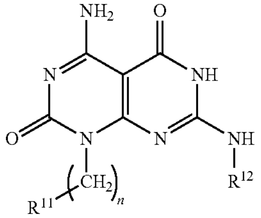

Where n is integer from 1 to 6.

And $R^{11}$ is β-amino acid (amino acid here refer to both D- and L-amino acid) having a β-amino group covalently bound to a carbon of the $(CH_2)_n$; or poly-β-peptide having a terminal β-amino group covalently bound to carbon of the $(CH_2)_n$. Following structures are some examples of β-amino acids:

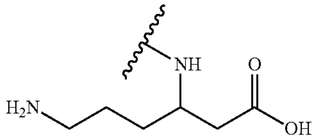

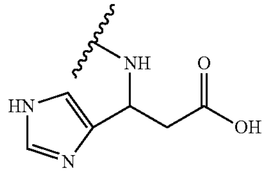

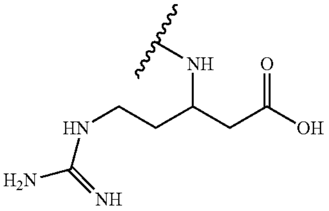

$R^{11}$ structure should also include structures shown below:

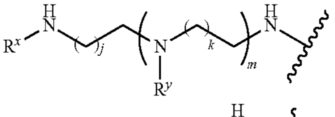

and

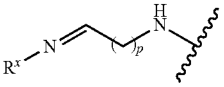

Within the structure above/is integer starting from 0, k is integer starting from 0, m is integer starting from 0, p is integer starting from 0; $R^x$ are aliphatic or hydrogen; $R^y$ is hydrogen or structure shown below:

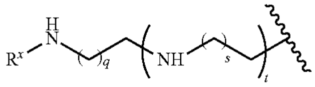

where q, s and t are integers starting from 0.

And $R^{12}$ is hydrogen or aliphatic.

Example 6: A Compound Having the Formula

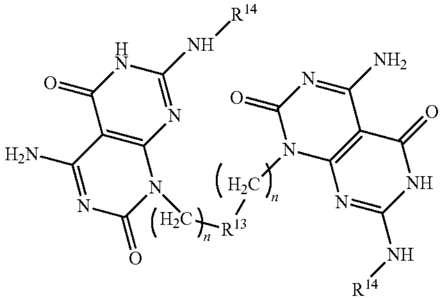

Where n is integer from 1 to 6.

And $R^{13}$ is α or β-amino acid (amino acid here refer to both D- and L-amino acid) having an α or β-amino group covalently bound to carbon of two $(CH_2)_n$ linkers; or poly-α or β-peptide having a terminal α or β-amino group covalently bound to carbon of two $(CH_2)_n$ linkers. Following structures are some examples of α or β-amino acids:

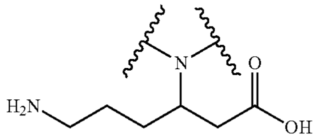

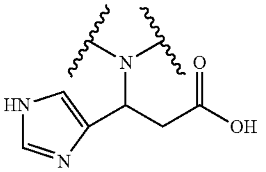

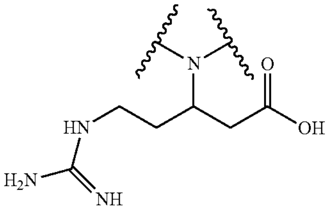

$R^{13}$ structure should also include structures shown below:

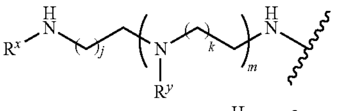

and

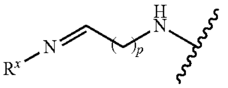

Within the structure above k is integer starting from 0, m is integer starting from 0, p is integer starting from 0; $R^x$ are aliphatic or hydrogen; $R^y$ is hydrogen or structure shown below:

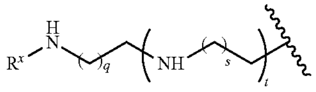

where q, s and t are integers starting from 0.

And $R^{14}$ is hydrogen or aliphatic.

Example 7: A Compound Having the Formula

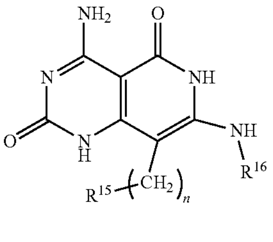

Where n is integer from 1 to 6.

And $R^{15}$ is α or β-amino acid (amino acid here refer to both D- and L-amino acid) having an α or β-amino group covalently bound to a carbon of the $(CH_2)_n$; or poly-α or β-peptide having a terminal α or β-amino group covalently bound to carbon of the $(CH_2)_n$. Following structures are some examples of α or β-amino acids:

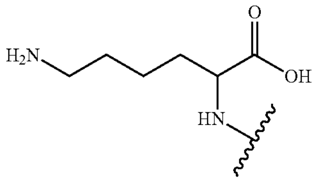

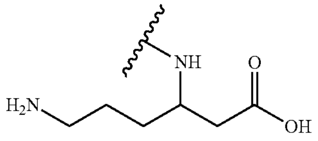

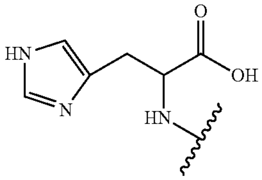

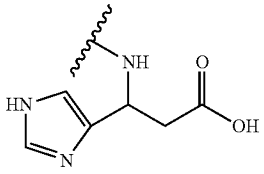

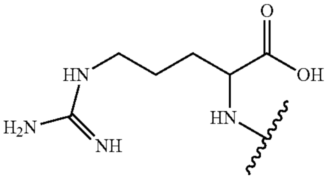

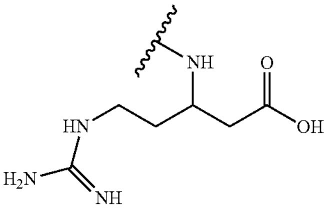

$R^{15}$ structure should also include structures shown below:

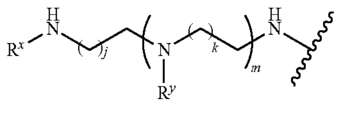

and

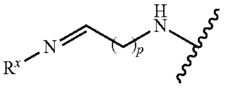

Within the structure above/is integer starting from 0, k is integer starting from 0, m is integer starting from 0, p is integer starting from 0; $R^x$ are aliphatic or hydrogen; $R^y$ is hydrogen or structure shown below:

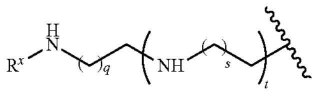

where q, s and t are integers starting from 0.

And $R^{16}$ is hydrogen or aliphatic.

Example 8: A Compound Having the Formula

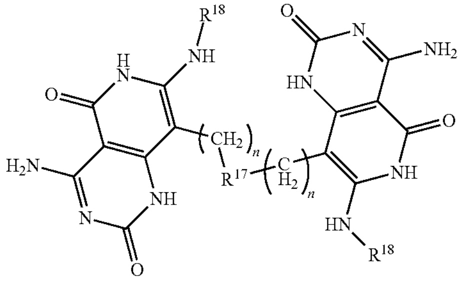

Where n is integer from 1 to 6.

And $R^{17}$ is α or β-amino acid (amino acid here refer to both D- and L-amino acid) having an α or β-amino group covalently bound to carbon of two $(CH_2)_n$ linkers; or poly-α or β-peptide having a terminal α or β-amino group covalently bound to carbon of two $(CH_2)$; linkers. Following structures are some examples of α or β-amino acids:

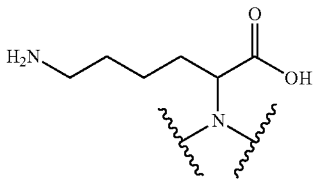

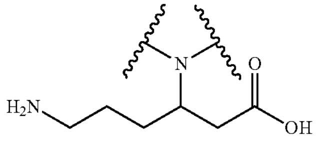

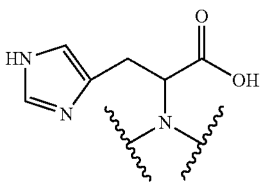

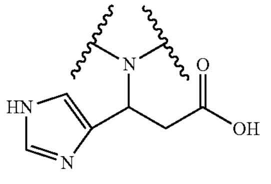

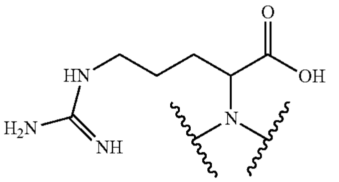

-continued

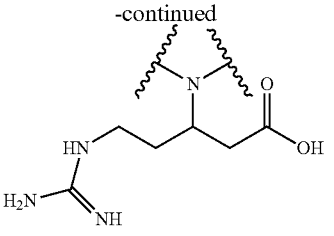

$R^{17}$ structure should also include structures shown below:

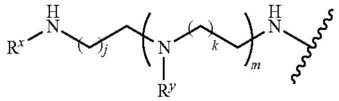

and

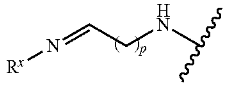

Within the structure above k is integer starting from 0, m is integer starting from 0, p is integer starting from 0; $R^x$ are aliphatic or hydrogen; $R^y$ is hydrogen or structure shown below:

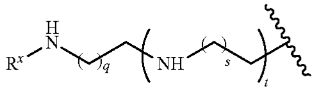

where q, s and t are integers starting from 0.

And $R^{18}$ is hydrogen or aliphatic.

What is claimed:

1. A composition comprising a compound of formula (I):

(I)

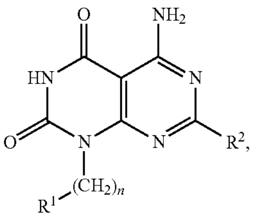

or a pharmaceutically acceptable salt or ester thereof wherein, n is an integer of 0, 1, 2, 3, 4, 5 or 6;

$R^1$ is selected from an α-amino acid, a β-amino acid, an α-polypeptide, a β-polypeptide,

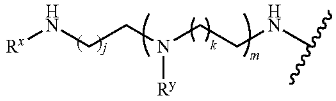

,

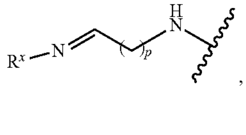

,

-continued

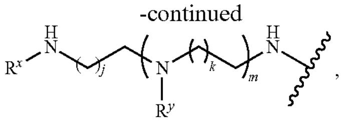

, or

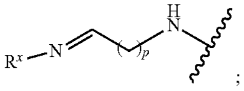

;

j, k, m and p are each independently an integer of 0 to 20;

$R^x$ is aliphatic or H;

$R^y$ is H or

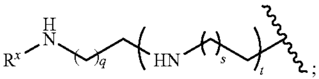

;

q, s and t are each independently an integer of 0 to 20;

$R^2$ is selected from H, $CH_3$, or $NHR^z$;

$R^z$ is selected from H or aliphatic; and wherein the compound is operative to self-assemble to form a nanotube.

2. The composition of claim 1, comprising a compound of formula (I)

(I)

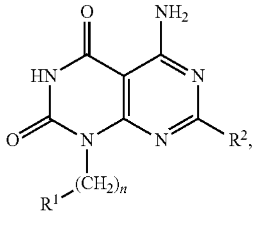

wherein the compound of Formula (I) is Compound A, (Compound A)

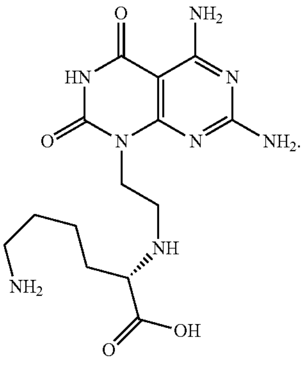

3. The composition of claim 1, wherein n is an integer of 1, 2, 3, 4, 5 or 6;

j, k, m and p are each independently an integer of 1 to 20; and q, s and t are each independently an integer of 1 to 20.

4. The composition of claim 1, wherein $R^1$ is selected from an α-amino acid comprising a covalent bond between an α-amino group and $(CH_2)_n$, a β-amino acid comprising a covalent bond between a β-amino group and $(CH_2)_n$, an α-polypeptide comprising a covalent bond between an α-amino group and $(CH_2)_n$, a β-polypeptide comprising a covalent bond between a β-amino group and $(CH_2)_n$,

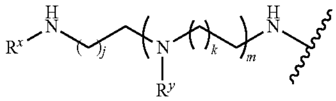

, or

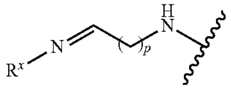

.

5. The composition of claim 2, wherein $R^1$ is an α-amino acid comprising a covalent bond between an α-amino group and $(CH_2)_n$ or a β-amino acid comprising a covalent bond between a β-amino group and $(CH_2)_n$.

6. The composition of claim 5, wherein $R^1$ in Formula (I) is

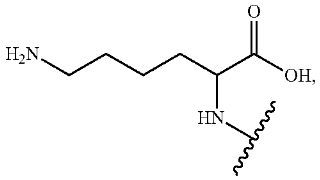

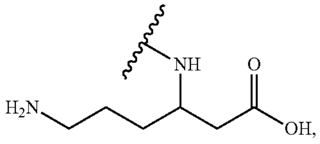

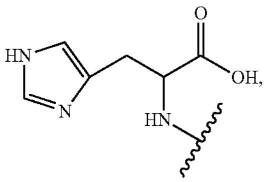

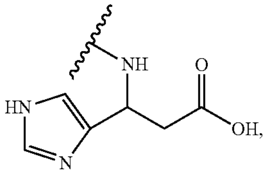

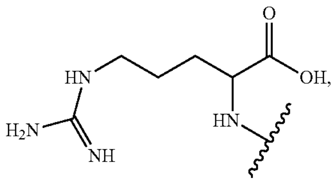

or

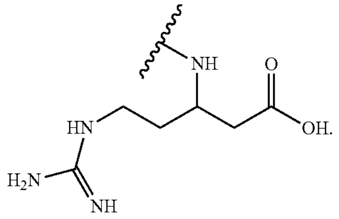

7. The composition of claim 1, wherein the compounds are provided in the form of a nanotube.

8. The composition of claim 7, wherein said nanotube further comprises one or more therapeutic agents.

9. The composition of claim 8, wherein said therapeutic agent comprises a nucleic acid, a peptide or a molecule.

10. The composition of claim 8, further comprising matrilin.

11. The composition of claim 10, wherein said matrilin comprises Matrilin-3.

12. The composition of claim 8, further comprising a bioactive agent.

13. The composition of claim 12, wherein the bioactive agent comprises a bone morphogenetic protein (BMP), vascular endothelial growth factor (VEGF), connective tissue growth factor (CTGF), osteoprotegerin, growth differentiation factor (GDF), cartilage-derived morphogenetic protein (CDMP), LIM mineralization protein (LMP), transforming growth factor beta (TGF-β), antibiotic, immunosuppressive agent, or a combination thereof.

14. The composition of claim 10, further comprising an immunosuppressive agent.

15. The composition of claim 14, wherein the immunosuppressive agent is selected from the group consisting of steroids, cyclosporine, cyclosporine analogs, cyclophosphamide, methylprednisolone, prednisone, azathioprine, FK-506, and er-15-deoxyspergualin.

* * * * *